US011599996B2

(12) United States Patent
Isgum et al.

(10) Patent No.: US 11,599,996 B2
(45) Date of Patent: Mar. 7, 2023

(54) METHOD AND SYSTEM FOR ASSESSING VESSEL OBSTRUCTION BASED ON MACHINE LEARNING

(71) Applicant: Pie Medical Imaging B.V., Maastricht (NL)

(72) Inventors: Ivana Isgum, Nieuwegein (NL); Majd Zreik, Utrecht (NL); Jean-Paul Aben, Limbricht (NL)

(73) Assignee: Pie Medical Imaging B.V., Maastricht (NL)

( * ) Notice: Subject to any disclaimer, the term of this patent is extended or adjusted under 35 U.S.C. 154(b) by 0 days.

(21) Appl. No.: 16/911,323

(22) Filed: Jun. 24, 2020

(65) Prior Publication Data

US 2020/0394795 A1    Dec. 17, 2020

Related U.S. Application Data

(63) Continuation of application No. 16/379,248, filed on Apr. 9, 2019, now Pat. No. 10,699,407.
(Continued)

(51) Int. Cl.
*G06K 9/46* (2006.01)
*G06T 7/00* (2017.01)
(Continued)

(52) U.S. Cl.
CPC ............ *G06T 7/0012* (2013.01); *A61B 6/481* (2013.01); *A61B 6/504* (2013.01); *A61B 6/507* (2013.01);
(Continued)

(58) Field of Classification Search
CPC ... G06T 7/0012; G06T 15/08; G06T 2200/08; G06T 2207/20081; G06T 2207/20084;
(Continued)

(56) References Cited

U.S. PATENT DOCUMENTS 7,369,691 B2    5/2008  Kondo
7,379,062 B2    5/2008  Poole
(Continued)

FOREIGN PATENT DOCUMENTS

WO    2015058044    4/2015

OTHER PUBLICATIONS

A machine-learning approach for computation of fractional flow reserve from coronary computed tomography, Lucian etu et al., J of applied Physics, 2016, pp. 42-52 (Year: 2016).*
(Continued)

*Primary Examiner* — Jayesh A Patel
(74) *Attorney, Agent, or Firm* — Gordon & Jacobson, P.C.

(57) ABSTRACT

Methods and systems are described for assessing a vessel obstruction. The methods and systems obtain a volumetric image dataset of a myocardium and at least one coronary vessel, wherein the myocardium comprises muscular tissue of the heart. A three-dimensional (3D) image corresponding to a coronary vessel of interest is created from the volumetric image dataset. Feature data that represents features of both the myocardium and the coronary vessel of interest is generated. At least some of the feature data is determined by a first machine learning-based model based on the 3D image. A second machine learning-based model is used to determine at least one parameter based on the feature data, wherein the at least one parameter represents functionally significant coronary lesion severity of the coronary vessel of interest.

32 Claims, 29 Drawing Sheets

Related U.S. Application Data

(60) Provisional application No. 62/656,066, filed on Apr. 11, 2018.

(51) Int. Cl.
*G06T 15/08* (2011.01)
*A61B 6/00* (2006.01)
*G06N 20/00* (2019.01)
*G06N 3/08* (2023.01)

(52) U.S. Cl.
CPC ............. *A61B 6/5217* (2013.01); *G06N 3/08* (2013.01); *G06N 20/00* (2019.01); *G06T 15/08* (2013.01); *G06T 2200/04* (2013.01); *G06T 2200/08* (2013.01); *G06T 2207/20081* (2013.01); *G06T 2207/20084* (2013.01); *G06T 2207/30048* (2013.01); *G06T 2207/30101* (2013.01)

(58) Field of Classification Search
CPC . G06T 2207/30101; G06T 2207/30048; G06T 2200/04; A61B 6/507; A61B 6/5217; A61B 6/481; A61B 6/504; G06N 20/00; G06N 3/08; G16H 50/50; G16H 50/20
See application file for complete search history.

(56) References Cited

U.S. PATENT DOCUMENTS

| | | | |
|---|---|---|---|
| 7,822,254 B2 | 10/2010 | Yatziv | |
| 8,073,227 B2 | 12/2011 | Gulsun | |
| 8,315,812 B2 | 11/2012 | Taylor | |
| 8,526,699 B2 * | 9/2013 | Mittal | G06T 7/0016 623/1.36 |
| 9,008,386 B2 | 4/2015 | Verstraeten | |
| 9,747,525 B2 | 8/2017 | Sauer | |
| 10,176,575 B2 | 1/2019 | Isgum | |
| 10,192,352 B2 | 1/2019 | De Vaan | |
| 10,395,366 B2 | 8/2019 | Isgum | |
| 10,699,407 B2 * | 6/2020 | Isgum | A61B 6/5217 |
| 11,004,198 B2 | 5/2021 | Isgum | |
| 2005/0059876 A1 * | 3/2005 | Krishnan | G06T 7/0012 600/407 |
| 2005/0065421 A1 | 3/2005 | Burckhardt | |
| 2005/0207630 A1 | 9/2005 | Chan | |
| 2010/0021025 A1 | 1/2010 | Hof | |
| 2010/0067760 A1 * | 3/2010 | Zhang | G06T 7/143 382/130 |
| 2010/0076296 A1 * | 3/2010 | Mittal | G06T 7/0012 600/408 |
| 2011/0224542 A1 * | 9/2011 | Mittal | G06T 7/143 600/425 |
| 2012/0078097 A1 | 3/2012 | Wang | |
| 2012/0207365 A1 | 8/2012 | Verstraeten | |
| 2014/0073977 A1 | 3/2014 | Grady | |
| 2015/0112182 A1 * | 4/2015 | Sharma | A61B 5/7264 600/408 |
| 2015/0262357 A1 * | 9/2015 | Igarashi | G16H 50/30 382/131 |
| 2016/0085936 A1 * | 3/2016 | Sankaran | A61B 5/02028 703/11 |
| 2017/0046616 A1 * | 2/2017 | Socher | G06F 30/00 |
| 2017/0258433 A1 | 9/2017 | Gulsun | |
| 2017/0262733 A1 | 9/2017 | Gulsun | |
| 2018/0025255 A1 | 1/2018 | Poole | |
| 2018/0032653 A1 * | 2/2018 | Aben | A61B 6/504 |
| 2018/0253531 A1 * | 9/2018 | Sharma | A61B 6/469 |
| 2018/0276817 A1 | 9/2018 | Isgum | |
| 2019/0130578 A1 | 5/2019 | Gulsun | |
| 2019/0139219 A1 | 5/2019 | Isgum | |
| 2019/0318476 A1 | 10/2019 | Isgum | |
| 2019/0380593 A1 | 12/2019 | Bouwman | |

OTHER PUBLICATIONS

Identifying Coronary Stenosis Using an Image-Recognition Neural Network, Lucy S. Goodenday et al., IEEE, 0739.51 75, 1997, pp. 139-144 (Year: 1997).*
Automatic Plaque Detection in IVOCT Pullbacks Using Convolutional Neural Networks, Nils Gessert et al., IEEE, 2018, pp. 426-434 (Year: 2018).*
"A Recurrent CNN for Automatic Detection and Classification of Coronary Artery Plaque and Stenosis in Coronary CT Angiography", Majd Zreik et al., arxiv.org, Cornell University Library, 20182018.
"A Survey on Deep Learning in Medical Image Analysis", Litjens Geert et al, Medical Image Analysis, vol. 24, Jul. 26, 2017, pp. 60-88.
"A survey on the application of recurrent neural networks to statistical language modeling", Mulder et al., Computer Speech & Language, vol. 30, No. 1, pp. 61-98, 2015.
"Attention-based deep multiple instance learning", Ilse et al., Jun. 28, 2018, arXiv preprint arXiv:1802.04712.
"Auto-encoding variational bayes", Kingma et al. May 1, 2014, arXiv preprint arXiv:1312.6114, 2013.
"Batch normalization: Accelerating deep network training by reducing internal covariate shift", Ioffe et al., in Proceedings of the 32nd International Conference on Machine Learning, 2015, pp. 448-456.
'Coronary artery centeriine extraction in cardiac CT angiography using a CNN-based orientation classifier', VVolterink et al., Med Image Anal. Jan. 2019;51:46-60.
"Deep sparse rectifier neural networks", Glorot et al., International Conference on Artificial Intelligence and Statistics, 2011, pp. 315-323.
"Long-term recurrent convolutional networks for visual recognition and description" Donahue et al., in Proceedings of the IEEE Conference on Computer Vision and Pattern Recognition, 2015, pp. 2625-2634.
"Oriented Gaussian Mixture Models for Nonrigid 2D/3D Coronary Artery Registration", Baka et al., IEEE Trans Med Imaging. May 2014; 33(5):1023-34.
"Recurrent Fully Convolutional Neural Networks for Multi-slice MRI Cardiac Segmentation", Poudel Rudra P. et al, International Conference on Computer Analysis of Images and patterns, 2017.
"Semi-automatic coronary artery centerline extraction in computed tomography angiography data", Metz et al., proceedings / IEEE International Symposium on Biomedical Imaging: from nano to macro, May 2007.
"Semi-supervised learning with deep generative models", Kingma et al., Advances in neural information processing systems, 2014, pp. 3581-3589.
"Standardized evaluation framework for evaluating coronary artery stenosis detection, stenosis quantification and lumen segmentation algorithms in computed tomography angiography", Kiris et al., Medical Image Analysis, vol. 17, No. 8, pp. 859-876,2013.
"3D Active Shape Model Matching for Left Ventricle Segmentation in Cardiac CT," Van Assen et al., Phytochemistry Jan. 2003, 5032.
"Adenosine Stress 64-and 256-Row Detector Computed Tomography Angiography and Perfusion Imaging a Pilot Study Evaluating the Transmural Extent of Perfusion Abnormalities to Predict Atherosclerosis Causing Myocardial Ischemia," George et al., Circulation: Cardiovascular Imaging 2 (3) (2009) 174-182.
"Aligning Coronary Anatomy and Mycoardial Perfusion Territories: An Algorithm for the CORE320 Multicenter Study," Cerci et al., Circ Cardiovasc Imaging. 2012, 5:587-595.
"Automated 3-Dimensional Quantification of Noncalcified and Calcified Coronary Plaque from Coronary CT Angiography," Dey et al., Cardiovascular Computed Tomography 2009, 3(6):372-382.
"Automatic Coronary Artery Calcium Scoring in Cardiac CT Angiography Using Paired Convolutional Neural Networks," Wolterink et al., Medical Image Analysis, 2016.
"Automatic Segmentation of the Left Ventricle in Cardiac CT Angiography Using Convolutional Neural Networks," Zreik et al., 2016 IEEE 13th International Symposium on Biomedical Imaging (ISBI), 2016, pp. 40-43.

(56) References Cited

OTHER PUBLICATIONS

"Bringing It All Together: Integration of Physiology With Anatomy During Cardiac Catheterization," Neil S. Kleiman, MD., Journal of the American College of Cardiology, 2011; vol. 58, No. 12:1219-1221.
"Comprehensive Assessment of Coronary Artery Stenoses: Computed Tomography Coronary Angiography Versus Conventional Coronary Angiography and Correlation with Fractional Flow Reserve in Patients with Stable Angina," Meijboom et al., Journal of the American College of Cardiology, 2008; vol. 52, No. 8:636-643.
"Computational Fluid Dynamics Applied to Cardiac Computed Tomography for Noninvasive Quantification of Fractional Flow Reserve," Charles A. Taylor, PhD et al., Journal of the American College of Cardiology, vol. 61, No. 22, 2013.
"Convolutional Deep Belief Networks for Scalable Unsupervised Learning of Hierarchical Representations," Lee et al., Proceedings of the 26th Annual International Conference on Machine Learning, 2009, pp. 609-616.
"Coronary centerline extraction from CT coronary angiographic images using a minimum cost path approach," Metz et al., Med Phys. Dec. 2009;36(12):5568-79.
"Deep Learning (Adaptive Computation and Machine Learning series)," Goodfellow et al., Nov. 18, 2016, ISBN 10: 0262035618.
"Fast and Accurate Deep Network Learning by Exponential Linear Units (ELUs)," Clevert et al., International Conference on Learning Representations, 2016.
"Gradient Methods for Minimizing Composite Objective Function," Nesterov et al., Tech. rep., UCL (2007).
"Learning Patient-Specific Lumped Models for Interactive Coronary Blood Flow Simulations", Nickisch et al., International Conference on Medical Image Computing and Computer-Assisted Intervention, Springer, 2015, pp. 433-441.
"Left Ventricular Shape Variation in Asymptomatic Populations: the Multi-Ethnic Study of Atherosclerosis," Medrano-Gracia et al., Journal of Cardiovascular Magnetic Resonance Jul. 30, 2014;16:56.
"Measurement of Fractional Flow Reserve to Assess the Functional Severity of Coronary-Artery Stenoses," Nico H.J. Pijls, MD et al., New England Journal of Medicine 1996, vol. 334, No. 26:1703-1708.
"Model Prediction of Subendocardial Perfusion of the Coronary Circulation in the Presence of an Epicardial Coronary Artery Stenosis," Med Biol Eng Comput 2008, 46:421-432.
"Myocardial Perfusion: Near-Automated Evaluation from Contrast Enhanced MR Images Obtained at Rest and During Vasodilator Stress", Tarroni, Radiology 2012 (Year 2012).
"Myocardial Strain Estimation from CT: Towards Computeraided Diagnosis on Infarction Identification," Wong et al., SPIE Medical Imaging Conference, Mar. 2015, DOI 10.1117/12.2081464.
"Patient-Specific Coronary Blood Supply Territories for Quantitative Perfusion Analysis," Zakkaroff et al., Computer Methods in Biomechanics and Biomedical Engineering: Imaging & Visualization 2016.
"Patient-Specific Mappings Between Myocardial and Coronary Anatomy," Termeer et al., Scientific Visualization: Advanced Concepts, 2010, p. 196-209.
"Patient-Specific Modeling of Blood Flow and Pressure in Human Coronary Arteries," Kim et al., Annals of Biomedical Engineering, vol. 38, No. 10, pp. 3195-3209, 2010.
"Perfusion Territories Subtended by Penetrating Coronary Arteries Increase in Size and Decrease in Number Toward the Subendocardium," Am J Physiol Heart Circ Physiol 2014, 306: H496-H504.
"Principal Component Analysis Used to Derive Patient-Specific Load-Free Geometry and Estimate Myocardial Stiffness in the Heart," Wang et al., 5th International Conference on Computational and Mathematical Biomedical Engineering—CMBE2017.
"Representation Learning: A Review and New Perspectives," Bengio et al., IEEE Trans. Pattern Anal. Mach. Intell. 35 (8), 2013, 1798-1828.
"SCCT Guidelines for the Performance and Acquisition of Coronary Computed Tomographic Angiography: A Report of the Society of Cardiovascular Computed Tomography Guidelines Committee Endorsed by the North American Society for Cardiovascular Imaging (NASCI)," Abbara et al., Journal of Cardiovascular Computed Tomography, Nov.-Dec. 2016;10(6):435-449.
"Segmentation of the Left and Right Cardiac Ventricle Using a Combined Bi-Temporal Statistical Model," Fritz et al., Proceedings of SPIE—The International Society for Optical Engineering, Mar. 2006, 6141, DOI10.1117/12.652991.
"Standardized Myocardial Segmentation and Nomenclature for Tomographic Imaging of the Heart. A Statement for Healthcare Professionals from the Cardiac Imaging Committee of the Council on Clinical Cardiology of the American Heart Association," Cerquiera et al., Circulation Jan. 29, 2002;105:539-542.
"Supervised Machine Learning: A Review of Classification Techniques," Kotsiantis et al., Informatica 31, 2007, 249-268.
"Textural Features for Image Classification," Haralick et al., IEEE Transactions on Systems, Man, and Cybernetics, Haralick et al., 1973, SMC-3 (6): 610-621.
"The Synthesized Vectorcardiogram Resembles the Measured Vectorcardiogram in Patients with Dyssynchronous Heart Failure," Engels et al., J Electrocardiol;48(4):586-592.
"Vectorcardiogram Synthesized From a 12-Lead ECG: Superiority of the Inverse Dower Matrix," Journal of Electrocardiology, Dec. 1988, 21(4):361-7.
"Web-Scale K-Means Clustering," D. Sculley, Proceedings of the 19th international conference on World wide web, ACM, 2010, pp. 1177-1178.
International Search Report and Written Opinion dated Aug. 16, 2019 of International Application No. PCT/EP2019/059051.
International Search Report and Written Opinion dated Jul. 25, 2018 for Application No. PCT/IB2018/051985.
Limitations of Noninvasive Measurement of Fractional Flow Reserve from Coronary Computed Tomography Angiography, De Caterina et al., Journal of the American College of Cardiology, vol. 59, Issue 15, Apr. 2012.
Validation of 3-Dimensional Quantitative Coronary Angiography based software to calculate vessel-FFR (the FAST study), Masdhedu et al., EuroPCR 2018.
"Assessment of coronary stenoses by myocardial perfusion imaging during pharmacologic coronary vasodilation. VII. Validation of coronary flow reserve as a single integrated functional measure of stenosis severity reflecting all its geometric dimensions", Kirkeeide et al., J Am Coll Cardiol. Jan. 1986;7(1):103-13.
"Graph attention networks for segment labeling in coronary artery trees", Nils Hampe et al., Proc. SPIE 11596, Medical Imaging 2021: Image Processing, 115961I (Feb. 15, 2021); doi: 10.1117/12.2581219.
"Graph convolutional networks for coronary artery segmentation in cardiac CT angiography", Wolterink et al., International Workshop on Graph Learning in Medical Imaging. Springer, Cham, 2019.
"Physiologic basis for assessing critical coronary stenosis. Instantaneous flow response and regional distribution during coronary hyperemia as measures of coronary flow reserve", Gould et al., Am J Cardiol. Jan. 1974;33(1):87-94.

\* cited by examiner

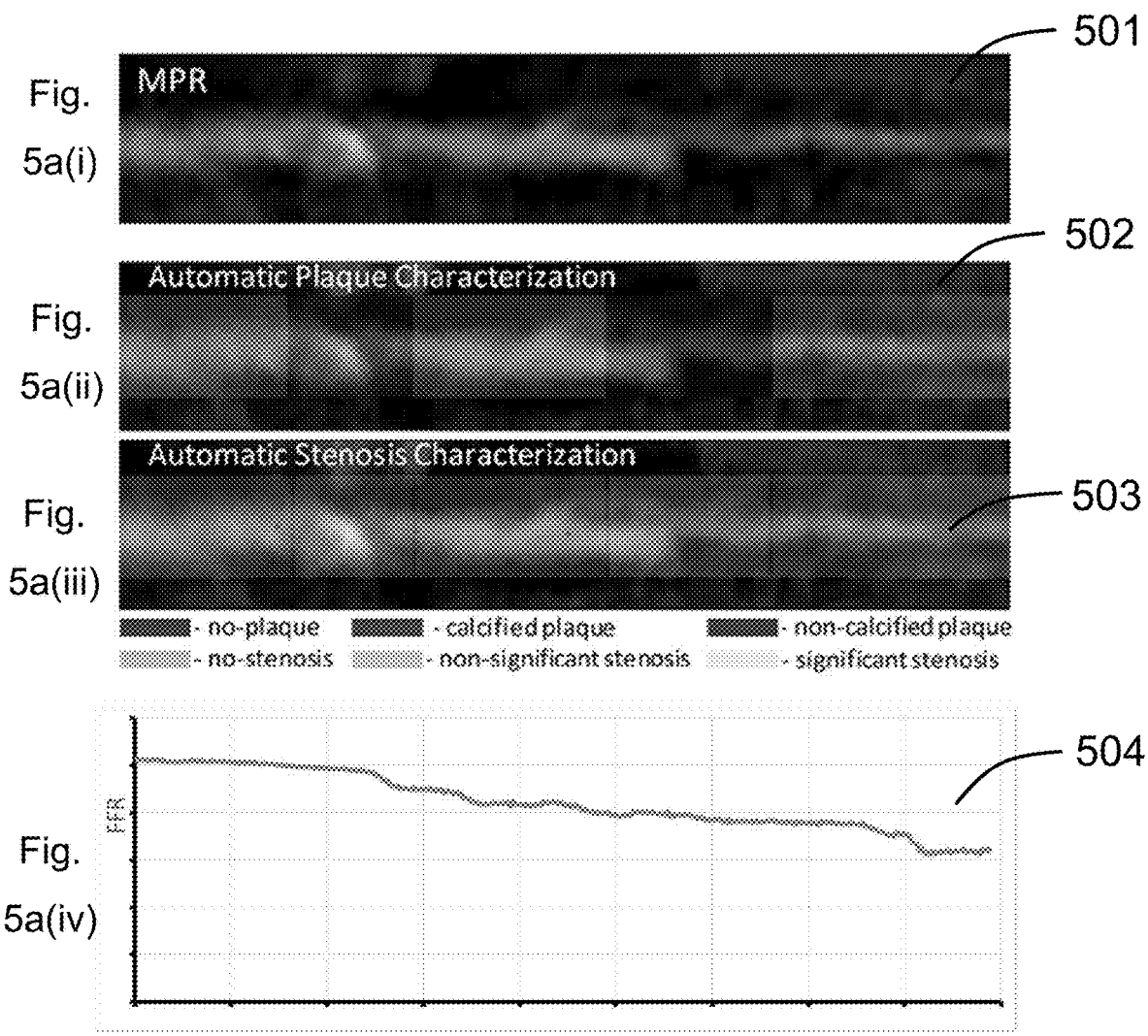
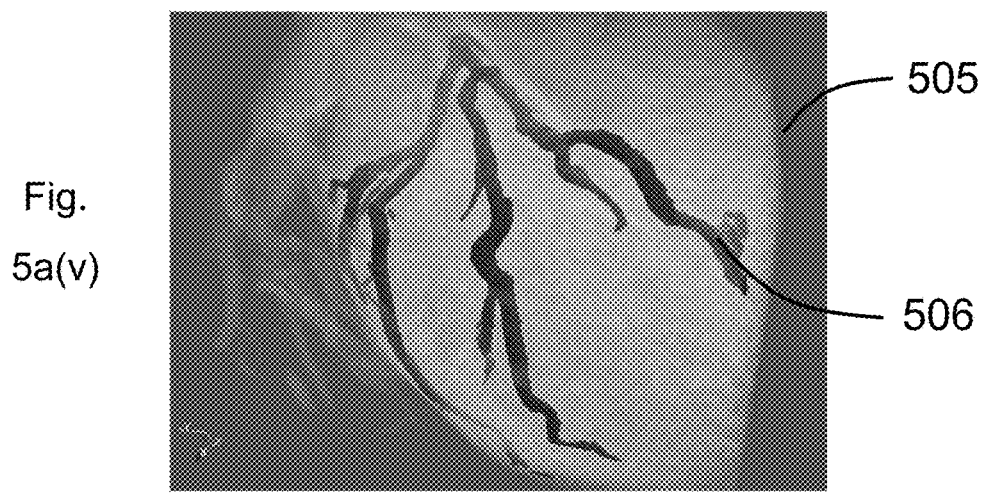

804  805

METHOD AND SYSTEM FOR ASSESSING VESSEL OBSTRUCTION BASED ON MACHINE LEARNING

CROSS-REFERENCE TO RELATED APPLICATION(S)

The present application is a continuation of U.S. application Ser. No. 16/379,248, filed on Apr. 9, 2019, which claims priority from U.S. Provisional App. No. 62/656,066, filed on Apr. 11, 2018, both of which are herein incorporated by reference in their entireties.

BACKGROUND OF THE INVENTION

1. Field

The present application generally relates to methods and systems to assess coronary parameters related to coronary atherosclerosis lesion severity in one or more coronary arteries.

2. State of the Art

Coronary artery disease (CAD) is one of the leading causes of death worldwide. CAD generally refers to conditions that involve narrowed or blocked blood vessels that can lead to reduced or absent blood supply to the sections distal to the stenosis resulting in reduced oxygen supply to the myocardium, resulting in, for instance, ischemia and chest pain (angina). Narrowing of a blood vessel is called stenosis and is caused by atherosclerosis which refers to the buildup of fats, cholesterol, and other substances in and on vessel walls (plaque), see FIG. 1. Atherosclerotic plaque can be classified according to its components, such as calcified plaque, soft plaque, and mixed plaque, i.e. plaque containing calcified and non-calcified components. Such non-calcified components include extracellular matrix, smooth muscle cells, macrophages, foam cells, lipid, and fibrous tissue. Calcified plaque is considered stable and its amount in the coronary artery is a strong predictor of cardiovascular events. Unlike calcified plaque, non-calcified plaque and mixed plaque are consider unstable and more prone to rupture. A plaque rupture may lead to acute major events such as a stroke, or a heart attached in case the rupture occurs in the coronary artery. A heart attack can result in a myocardium infarction resulting in irreversible damage to the myocardium. As different types of plaque and varying grades of stenosis lead to different patient management strategies, it is important to detect and characterize coronary artery plaque and stenosis grade.

Besides the grade of stenosis (anatomical stenosis), another very important aspect in the prevention and treatment of CAD is the functional assessment of such narrowed anatomical stenosis or blocked blood vessels.

Presently, X-ray angiography is the imaging modality used during treatment of stenotic (narrowed) coronary arteries by means of a minimally invasive procedure also known as percutaneous coronary intervention (PCI) within the catheterization laboratory. During PCI, a (interventional) cardiologist feeds a deflated balloon or other device on a catheter from the inguinal femoral artery or radial artery up through blood vessels until they reach the site of blockage in the artery. X-ray imaging is used to guide the catheter threading. PCI usually involves inflating a balloon to open the artery with the aim to restore unimpeded blood flow. Stents or scaffolds may be placed at the site of the blockage to hold the artery open. For intermediate coronary anatomical lesions (defined as luminal narrowing of 30-70%), for instance, it is not always obvious if the stenosis is a risk for the patient and if it is desired to take action. Overestimation of the severity of the stenosis can cause a treatment which in hindsight would not have been necessary and therefore exposing the patient to risks that are not necessary. Underestimation of the severity of the stenosis, however, could induce risks because the patient is left untreated while the stenosis is in reality severe and actually impedes flow to the myocardium. Especially for these situations it is desired to have an additional functional assessment to aid in a good decision making.

Fractional Flow Reserve (FFR) has been used increasingly over the last 10-15 years as a method to identify and effectively target the coronary lesion most likely to benefit from PCI. FFR is a technique used to measure pressure differences across a coronary artery stenosis to determine the likelihood that the stenosis impedes oxygen delivery to the heart muscle. The technique involves percutaneously inserting a pressure-transducing wire inside the coronary artery and measuring the pressure behind (distal to) and before (proximal to) the lesion and is performed in the catheterization laboratory. This is best done in a hyperemic state because in the case of maximum hyperemia, blood flow to the myocardium is proportional to the myocardium perfusion pressure. FFR therefore provides a quantitative assessment of the functional severity of the coronary lesion as described in Pijls et al. in, "Measurement of Fractional Flow Reserve to Assess the Functional Severity of Coronary-Artery Stenoses", N Engl J Med 1996, 334:1703-1708. Although the European Society of Cardiology (ESC) and the American College of Cardiology/American Heart Association (ACC/AHA) guidelines recommend the use of FFR in patients with intermediate coronary stenosis (30-70%), visual assessment, whether or not supported by QCA, of X-ray coronary angiograms alone is still used in over 90% of procedures to select patients for percutaneous coronary intervention (Kleiman et al, "Bringing it all together: integration of physiology with anatomy during cardiac catheterization", J Am Coll Cardiol. 2011; 58:1219-1221). FFR, however, has some disadvantages. The technique is associated with the additional cost of a pressure wire which can only be used once. Furthermore, measuring FFR requires invasive catheterization with the associated cost and procedure time. Also, in order to induce (maximum) hyperemia, additional drug infusion (adenosine or papaverine) is required, which is an extra burden for the patient.

Coronary CT angiography (CCTA) is a well-established modality for identification, as well as for exclusion, of patients with suspected CAD. It allows for noninvasive detection and characterization of coronary artery plaque and grading of coronary artery stenosis. Today, these tasks are typically performed in the clinic by visual assessment, or semi-automatically by first utilizing lumen and arterial wall segmentation and thereafter, defining the presence of plaque or stenosis. However, the former suffers from substantial interobserver variability, even when performed by experienced experts, while the latter is dependent on coronary artery lumen and wall segmentation which is typically time-consuming and cumbersome, especially in images with extensive atherosclerotic plaque or imaging artefacts.

Although CCTA can reliably exclude the presence of significant coronary artery disease, many high-grade stenosis seen on CCTA are not flow limiting. This potential for false positive results has raised concerns that widespread use of CCTA may lead to clinically unnecessary coronary revascularization procedures. This lack of specificity of CCTA is one of the main limitations of CCTA in determining the hemodynamic significance of CAD (Meijboom et al, "Comprehensive assessment of coronary artery stenoses: computed tomography coronary angiography versus conventional coronary angiography and correlation with fractional reserve in patients with stable angina", Journal of the American College of Cardiology 52 (8) (2008) 636-643). As a result, CCTA may lead to unnecessary interventions on the patient, which may pose added risks to patients and may result in unnecessary health care costs.

To reduce the number of unnecessary catheterization procedures, obtaining coronary artery lesion parameters (such as plaque type, anatomical lesion severity and functional coronary lesion severity) upfront to a catheterization procedures and with a noninvasively imaging modality such as CCTA is being intensively investigated. Currently several (semi-)automatic methods for determination of either anatomical stenosis severity, or the plaque type, or the functional significance of coronary artery stenosis in CCTA have been proposed. These methods heavily rely on the segmentation of the coronary lumen and coronary vessel wall in case of plaque type detection as for instance described by Kiris et al. "Standardized evaluation framework for evaluating coronary artery stenosis detection, stenosis quantification and lumen segmentation algorithms in computed tomography angiography", Medical Image Analysis, vol. 17, no. 8, pp. 859-876, 2013.

Since there are numerous artifacts on CCTA, such as blooming artefacts caused by large arterial calcifications and presents of stents, segmentation inaccuracies are a known problem resulting in accuracy in the extracted coronary parameters. In addition, motion, lower SNR, and mis-registration reduces its accuracy even more. Therefore, CCTA data with good image quality is essential for the accuracy of the extracted coronary parameters such as coronary plaque type, anatomical and functional coronary lesion severity.

In Taylor et al "Computational Fluid Dynamics Applied to Cardiac Computed Tomography for Noninvasive Quantification of Fractional Flow Reserve", Journal of the American College of Cardiology, Vol. 61, No. 22, 2013, and U.S. Pat. No. 8,315,812, a noninvasive method for quantifying FFR from CCTA is described (FFRCT). This technology uses computational fluid dynamics (CFD) applied to CCTA after semi-automated segmentation of the coronary tree including a part of the ascending aorta covering the region in which both the left coronary artery as well as the right coronary artery emanate. Three-dimensional (3D) blood flow and pressure of the coronary arteries are simulated, with blood modeled as an incompressible Newtonian fluid with Navier-Stokes equations and solved subject to appropriate initial and boundary conditions with a finite element method on parallel supercomputer. The FFRCT is modeled for conditions of adenosine-induced hyperemia without adenosine infusion. This process is computationally complex and time-consuming and may require several hours and heavily relies in the 3D anatomical coronary model as a result of the segmentation which suffers amongst others from the same limitation as described above.

Thus, there is a need for obtaining coronary artery lesion parameters (such as plaque type, anatomical lesion severity and functional coronary lesion severity) without relying on the detailed morphology of the coronary arterial system.

SUMMARY

In accordance with aspects herein, method and systems are provided for assessing a vessel obstruction that involve a) obtaining a volumetric image dataset of a myocardium and at least one coronary vessel, wherein the myocardium comprises muscular tissue of the heart;

b) creating a three-dimensional (3D) image corresponding to a coronary vessel of interest based on the volumetric image dataset of a);

c) generating feature data that represents features of both the myocardium and the coronary vessel of interest, wherein at least some of the feature data is determined by a first machine learning-based model based on the 3D image of b); and d) employing a second machine learning-based model to determine at least one parameter based on the feature data of c), wherein the at least one parameter represents functionally significant coronary lesion severity of the coronary vessel of interest.

In embodiments, the at least one parameter that represents functionally significant coronary lesion severity can be selected from the group consisting of: a fractional flow reserve (FFR) value, coronary flow reserve value, instantaneous wave-free ratio, hyperemic myocardium perfusion value, index of microcirculatory resistance, pressure drop along a coronary artery, FFR along a coronary artery, and combinations thereof.

In embodiments, the creation of the 3D image can be based on axial trajectory of the coronary vessel of interest that is extracted from the volumetric image dataset of a).

In embodiments, the feature data of c) can be generated by:
using the axial trajectory of the coronary vessel of interest to sample image data that corresponds to both the myocardium and the coronary vessel of interest; and
using the sampled image data as input to the first machine learning-based model, wherein the first machine learning-based model is configured to automatically generate the feature data of c).

In other embodiments, the feature data of c) can be generated by:
using the axial trajectory of the coronary vessel of interest to sample image data that corresponds to the coronary vessel of interest;
using the image data as input to the first machine learning-based model, wherein the first machine learning-based model is configured to automatically generate first feature data, wherein the first feature data represents features of the coronary vessel of interest;
generating second feature data from additional myocardium analysis of the volumetric image dataset, wherein the second feature data represents features of the myocardium; and
combining the first feature data and the second feature data to generate the feature data of c).

In embodiments, the second feature data can be determined using at least one of: a convolutional auto-encoder, Gaussian filters, transmural perfusion ratio, Haralick features, myocardium thickness, and heart shape.

In embodiments, the second feature data can be determined using an unsupervised machine learning which employs a convolution auto-encoder.

In embodiments, the operations of c) and d) can be repeated using image data corresponding to the axial trajectory of the coronary vessel of interest to determine values of the at least one parameter representing functionally significant coronary lesion severity along the length of the coronary vessel of interest.

In embodiments, the 3D image can be a multi-planer reformatted (MPR) image that is constructed from samples of the volumetric image dataset along an axial trajectory of the coronary vessel of interest.

In embodiments, multiple 3D images can be created from the volumetric dataset, wherein the multiple 3D images correspond to a plurality of coronary vessels of interest and are based on extraction of axial trajectories for the plurality of coronary vessels of interest.

In embodiments, the axial trajectories for the plurality of coronary vessels of interest corresponds to centerlines for plurality of coronary vessels of interest.

In embodiments, sampled image data from the multiple 3D images can be used as input to the first machine learning-based model to generate data representing features of the plurality of coronary vessels of interest, wherein such data is included in the feature data of c).

In embodiments, the first machine learning-based model can employ a recurrent convolutional neural network or at least one convolutional autoencoder.

In embodiments, the second machine learning-based model can employ a supervised machine learning classifier.

In embodiments, the second machine learning-based model can employ a neural network, at least one SoftMax classifier, or a support vector machine.

In embodiments, the second machine learning-based model can be trained using reference values derived from invasive measurements involving pullback of a guidewire located in a target coronary vessel, measured coronary flow reserve, index of microcirculatory resistance, major adverse cardiac events or revascularization after acquisition of the volume image data set, results of cardiac stress test, and results of myocardial imaging by magnetic resonance imaging (MM), SPECT, PET, CT perfusion, or ultrasound.

In embodiments, the training of the second machine learning-based model can involve aligning the reference values to spatial coordinates of a 3D image corresponding to the target coronary vessel.

In other embodiments, the methods and systems can involve obtaining a volumetric image dataset for a target organ that includes a vessel of interest; extracting an axial trajectory extending along of a vessel of interest (VOI) within the volumetric image dataset; creating a three-dimensional (3D) multi-planer reformatted (MPR) image based on the volumetric image dataset and the axial trajectory of the VOI; and extracting a VOI parameter from the MPR utilizing a machine learning-based vessel obstruction assessment (VOA) model.

Optionally, the methods and systems can implement a prediction phase to at least one of i) detect plaque type, ii) classify anatomical severity of vessel blockage, and/or iii) classify a hemodynamic severity of vessel obstructions within an unseen portion of the volumetric image data set. Optionally, the machine learning-based VOA model generates a sequence of cubes from the MPR image, each of the cubes including a group of voxel from the MPR image, the sequence of cubes created within sections of the VOI resulting in a sequence of cubes for corresponding sections. Optionally, the machine learning-based VOA model extracts image features associated with cubes from the sequence of cubes independently. Optionally, the machine learning analyzes the image features in sequential dependence. Optionally, a size of the cube is defined to contain a whole lumen for the VOI and a portion of tissue outside of the lumen to facilitate extracting the VOI parameter in connection with positive remodeling, wherein positive remodeling refers to a direction of atherosclerotic plaque growth. Optionally, the axial trajectory may correspond to a coronary centerline of the VOI, the coronary centerline representing a center of a coronary lumen along a coronary section of interest, the axial trajectory corresponds to a single coronary artery, a coronary bifurcation or a full coronary tree, wherein, when the coronary section of interest includes one or more bifurcation(s), the coronary centerline includes the one or more bifurcations.

The machine learning-based VOA model may be based on a recurrent convolutional neural network (RCNN) which is employed to analyze a vicinity along the axial trajectory of the VOI in the MPR image, the RCNN connects a convolutional neural network (CNN) with a recurrent neural network (RNN) connected in series to analyze the portion of the MPR along the axial trajectory as a sequential input. The machine learning-based VOA model may apply at least one convolution layer followed by a max pooling layer to extract an image feature of interest from the MPR image and utilizes classifiers for at least one of characterizing plaque type, classify anatomical significance of a stenosis or determining the functional significance of a stenosis. The machine learning-based VOA model may include a feature extraction for creating a feature vector based on the MPR image, the feature vector comprises a series of factors that are measured or extracted from a reference database of images, the series of factors describing or characterizing the nature of a corresponding wall region of the vessel of interest, the machine learning-based VOA model further including a classifier to classify the feature vector extracted from the MPR image. The VOI parameter may include at least one of coronary plaque type, anatomical coronary lesion severity or functionally significant coronary lesion severity, and wherein the machine learning-based VOA model assesses at least one of i) functionally significant coronary lesion severity, ii) plaque type or iii) anatomical coronary lesion severity.

In accordance with aspects herein, methods and systems are provided to train a vessel obstruction assessment (VOA) model involving: obtaining a training database that includes volumetric imaging datasets for multiple patients and corresponding coronary artery disease (CAD) related reference values, the volumetric image data sets being for a target organ that includes a vessel of interest, the CAD related reference values corresponding to one or more points along a vessel of interest within the corresponding imaging data set; for at least a portion of the volumetric image data sets and corresponding CAD related reference values, extracting an axial trajectory extending along of a vessel of interest (VOI) within the corresponding volumetric image dataset; creating a three-dimensional (3D) multi-planer reformatted (MPR) image based on the corresponding volumetric image dataset and the axial trajectory of the VOI, the MPR image extending along the axial trajectory of the VOI; and training a machine learning-based vessel obstruction assessment (VOA) model based on the MPR images, the training further comprising extracting, from the MPR images, features characterizing a CAD related parameter along the axial trajectory within the VOI.

Optionally, the methods and system can align the CAD related reference values to spatial coordinates of the corresponding MPR images. Optionally, the methods and systems can generate a sequence of cubes from the corresponding MPR images, each of the cubes including a group of voxel from the corresponding MPR image, the sequence of cubes created within sections of the VOI resulting in a sequence of cubes for corresponding sections. Optionally, the training further comprises applying a convolutional neural network to a sequence of cubes alone the MPR image to build the machine learning-based VOA model. Optionally, the applying further comprises generating a set of encodings at points along the axial trajectory to form a set of one-dimensional (1D) sequences, each of the 1D sequences representing a specific encoding along the VOI, the training further comprising applying a supervised classifier to learn a fractional flow reserve (FFR) classifier based on the 1D sequences.

In accordance with aspects herein, a system is provided for assessing a vessel obstruction. The system comprises memory configured to store a volumetric image dataset for a target organ that includes a vessel of interest; one or more processors that, when executing program instructions stored in the memory, are configured to: extract an axial trajectory extending along of a vessel of interest (VOI) within the volumetric image dataset; create a three-dimensional (3D) multi-planer reformatted (MPR) image based on the volumetric image dataset and the axial trajectory of the VOI; and extract a VOI parameter from the MPR utilizing a machine learning-based vessel obstruction assessment (VOA) model.

Optionally, the one or more processors are configured to implement a prediction phase to at least one of i) detect plaque type, ii) classify anatomical severity of vessel blockage, and/or iii) classify a hemodynamic severity of vessel obstructions within an unseen portion of the volumetric image data set. Optionally, the machine learning-based VOA model generates a sequence of cubes from the MPR image, each of the cubes including a group of voxel from the MPR image, the sequence of cubes created within sections of the VOI resulting in a sequence of cubes for corresponding sections. Optionally, the machine learning-based VOA model extracts image features associated with cubes from the sequence of cubes independently. Optionally, the machine learning analyzes the image features in sequential dependence. A size of the cube may be defined to contain a whole lumen for the VOI and a portion of tissue outside of the lumen to facilitate extracting the VOI parameter in connection with positive remodeling, wherein positive remodeling refers to a direction of atherosclerotic plaque growth. The axial trajectory may correspond to a coronary centerline of the VOI, the coronary centerline representing a center of a coronary lumen along a coronary section of interest, the axial trajectory may correspond to a single coronary artery, a coronary bifurcation or a full coronary tree, wherein, when the coronary section of interest includes one or more bifurcation(s), the coronary centerline includes the one or more bifurcations. The machine learning-based VOA model may be based on a recurrent convolutional neural network (RCNN) which is employed to analyze a vicinity along the axial trajectory of the VOI in the MPR image, the RCNN connects a convolutional neural network (CNN) with a recurrent neural network (RNN) connected in series to analyze the portion of the MPR along the axial trajectory as a sequential input. The machine learning-based VOA model may apply at least one convolution layer followed by a max pooling layer to extract an image feature of interest from the MPR image and utilizes classifiers for at least one of detecting plaque type, characterizing plaque type, detecting stenosis or determining an anatomical significance of a stenosis. The machine learning-based VOA model may include a feature extraction for creating a feature vector based on the MPR image, the feature vector comprises a series of factors that are measured or extracted from a reference database of images, the series of factors describing or characterizing the nature of a corresponding wall region of the vessel of interest, the machine learning-based VOA model further including a classifier to classify the feature vector extracted from the MPR image. The VOI parameter may include at least one of coronary plaque type, anatomical coronary lesion severity or functionally significant coronary lesion severity, and wherein the machine learning-based VOA model assesses at least one of i) functionally significant coronary lesion severity, ii) plaque type or iii) anatomical coronary lesion severity.

In accordance with embodiments herein, a system is provided to train a vessel obstruction assessment (VOA) model. The system comprises: memory configured to store a training database that includes volumetric imaging datasets for multiple patients and corresponding coronary artery disease (CAD) related reference values, the volumetric image data sets being for a target organ that includes a vessel of interest, the CAD related reference values corresponding to one or more points along a vessel of interest within the corresponding imaging data set; one or more processors that, when executing program instructions stored in the memory, are configured to: for at least a portion of the volumetric image data sets and corresponding CAD related reference values, extract an axial trajectory extending along of a vessel of interest (VOI) within the corresponding volumetric image dataset; create a three-dimensional (3D) multi-planer reformatted (MPR) image based on the corresponding volumetric image dataset and the axial trajectory of the VOI, the MPR image extending along the axial trajectory of the VOI; and training a machine learning-based vessel obstruction assessment (VOA) model based on the MPR images, the training further comprising extracting, from the MPR images, features characterizing a CAD related parameter along the axial trajectory within the VOI.

Optionally, the processors are further configured to align the CAD related reference values to spatial coordinates of the corresponding MPR images. Optionally, the processors are further configured to generate a sequence of cubes from the corresponding MPR images, each of the cubes including a group of voxel from the corresponding MPR image, the sequence of cubes created within sections of the VOI resulting in a sequence of cubes for corresponding sections. Optionally, the processors are further configured to apply a convolutional neural network to a sequence of cubes alone the MPR image to build the machine learning-based VOA model. Optionally, the one or more processor are further configured to generate a set of encodings at points along the axial trajectory to form a set of one-dimensional (1D) sequences, each of the 1D sequences representing a specific encoding along the VOI, the one or more processors to perform the training by applying a supervised classifier to learn a fractional flow reserve (FFR) classifier based on the 1D sequences.

BRIEF DESCRIPTION OF THE DRAWINGS

The characteristics of the present application and the advantages derived therefrom will be more apparent from the following description of non-limiting embodiments, illustrated in the annexed drawings.

FIGS. 5a(i)-5a(v) show an example on how the results obtained by an embodiment of present application can be presented.

DETAILED DESCRIPTION OF EMBODIMENTS

Figure 1:
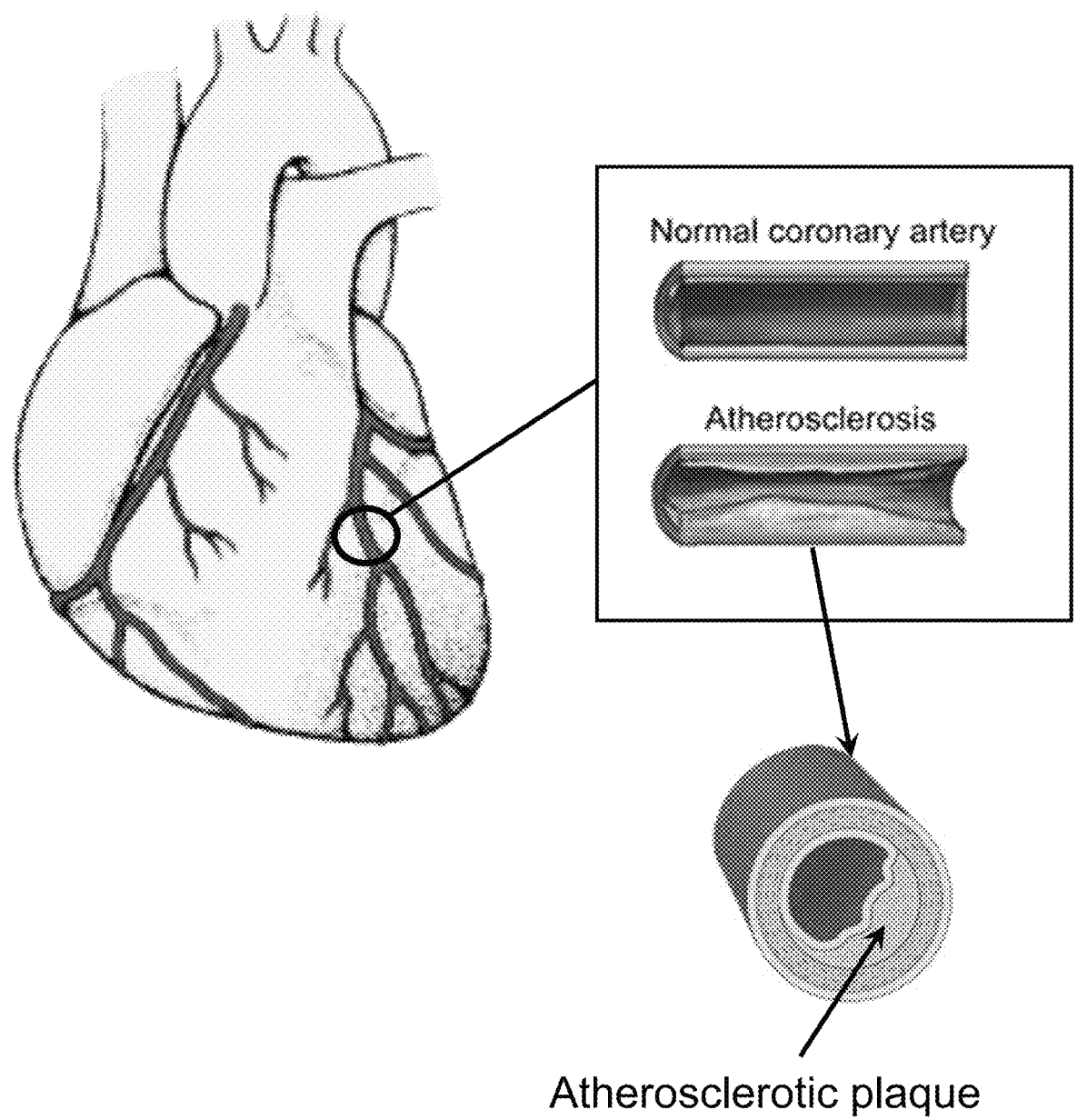
FIG. 1 shows an example of coronary atherosclerosis.

The term "unseen", as used throughout, refers to items which has not been used during the training phase. Item in this context means, a volumetric image, a reference value, features, and/or other things used during the training phase to train the machine learning based VOA model. Instead, the unseen features, images, geometries, and other unseen items refer to aspects of a patient or object of interest that is being analyzed during the prediction phase of operation.

The term "section", when used in connection with describing cubes of voxels, shall refer to substantially continuous geometric regions along a vessel of interest.

Throughout the present specification, terms which are common in the field of machine learning/deep learning are used. For detailed explanation of these terms a reference is made to Litjens et al, "A survey on deep learning in medical image analysis", Med Image Anal. 2017 December; 42:60-88.

Throughout the present specification the term "cubes" and "cuboid" are used. Both terms describe a volumetric shape, in which a "cube" means a volumetric cube with equal size of width, height and depth. A "cuboid" is similar to a "cube" but a cuboid may have different sizes of width, height and/or depth.

The present application relates to methods and systems for machine learning to assess coronary parameters related to CAD such as plaque type, anatomical severity, and functional severity of one or more vessel obstructions of a target organ based on contrast enhanced volumetric image dataset. In a preferred embodiment the target organ represent the heart and the vessels the coronary arteries. A functionally significant stenosis is a hemodynamically significant obstruction of a vessel, and with respect to coronary arteries it defines the likelihood that coronary artery obstruction(s) impedes oxygen delivery to the heart muscle and causes anginal symptoms. Fractional flow reserve is a hemodynamic index for assessment of functionally significant coronary artery obstruction(s). In addition to fractional flow reserve, other hemodynamic indices can be used to assess functionally significant coronary artery obstruction(s), such as coronary flow reserve, instantaneous wave-free ratio, hyperemic myocardium perfusion, index of microcirculatory resistance and pressure drop along a coronary artery.

Embodiments of the present application utilize machine learning to determine coronary parameters related to CAD such as plaque type, anatomical severity, and functional severity of one or more vessel obstructions from a CCTA dataset. Machine learning is a subfield of computer science that "gives computers the ability to learn without being explicitly programmed". Evolved from the study of pattern recognition and computational learning theory in artificial intelligence, machine-learning explores the study and construction of algorithms that can learn from and make predictions on data—such algorithms overcome following strictly static program instructions by making data driven predictions or decisions, through building a model from sample inputs. Machine-learning is employed in a range of computing tasks where designing and programming explicit algorithms is infeasible.

Given a dataset of images with known class labels, machine-learning systems can predict the class labels of new images. There are at least two parts to any such system. The first part of the machine learning-based Vessel Obstruction Assessment (VOA) model is a feature extraction (extractor), being an algorithm for creating a feature vector given an image. A feature vector comprises a series of factors (e.g. multiple numbers) that are measured or extracted from the image dataset(s), which describe or characterize the nature of the corresponding wall region of the image. These features are then used by the second part of the VOA model, a classifier, to classify unseen feature vectors extracted from the unseen image. Given a (large) database of images and extracted feature vectors whose labels are known and were used beforehand to train the machine learning-based VOA model, classifying unseen images based on the features extracted the same way as in images with (known) labels (training images) is possible.

Figure 2:
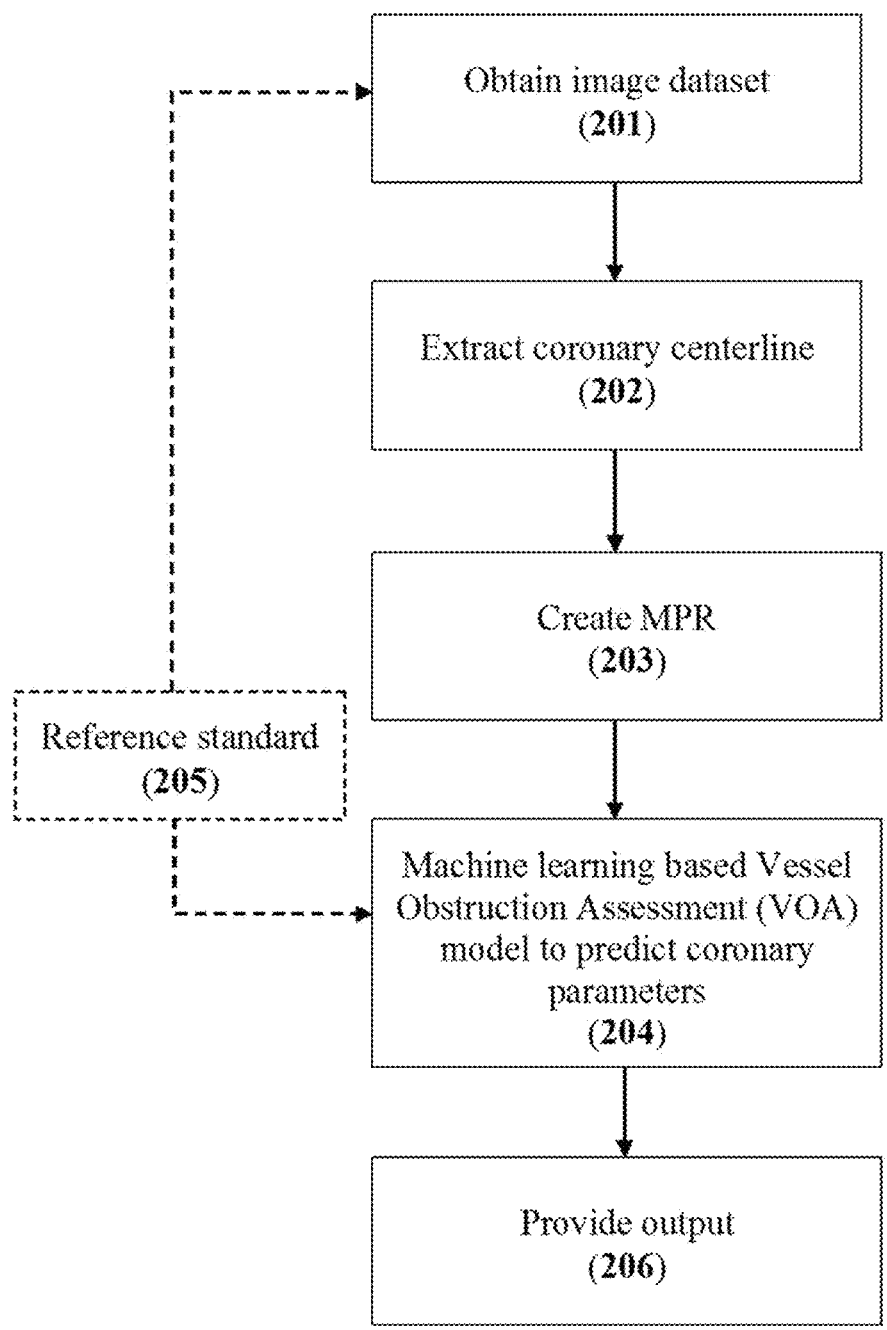
FIG. 2 illustrates a flowchart of a machine learning based method for determining coronary parameters related to coronary atherosclerosis lesion severity in one or more coronary arteries to an embodiment of the present application.

FIG. 2 shows a flow chart illustrating the operations according to an embodiment of the present application. The operations employ an imaging system capable of acquiring and processing a CCTA dataset of an organ (or portion thereof) or other object of interest. The operations of FIG. 2 (as well as the operations of any other methods, algorithms and processes described herein) are implemented by one or more processors, while executing program instructions. The one or more processors may be implemented on various computing devices, such as a smart phone, tablet device, laptop computer, desktop computer, workstation, remote server, medical network, and the like. Alternatively, the one or more processors may be distributed between one or more separate computing devices, such that a portion of the operations are performed by one computing device, while the remainder of the operations are performed by one or more other computing devices.

Figure 3:
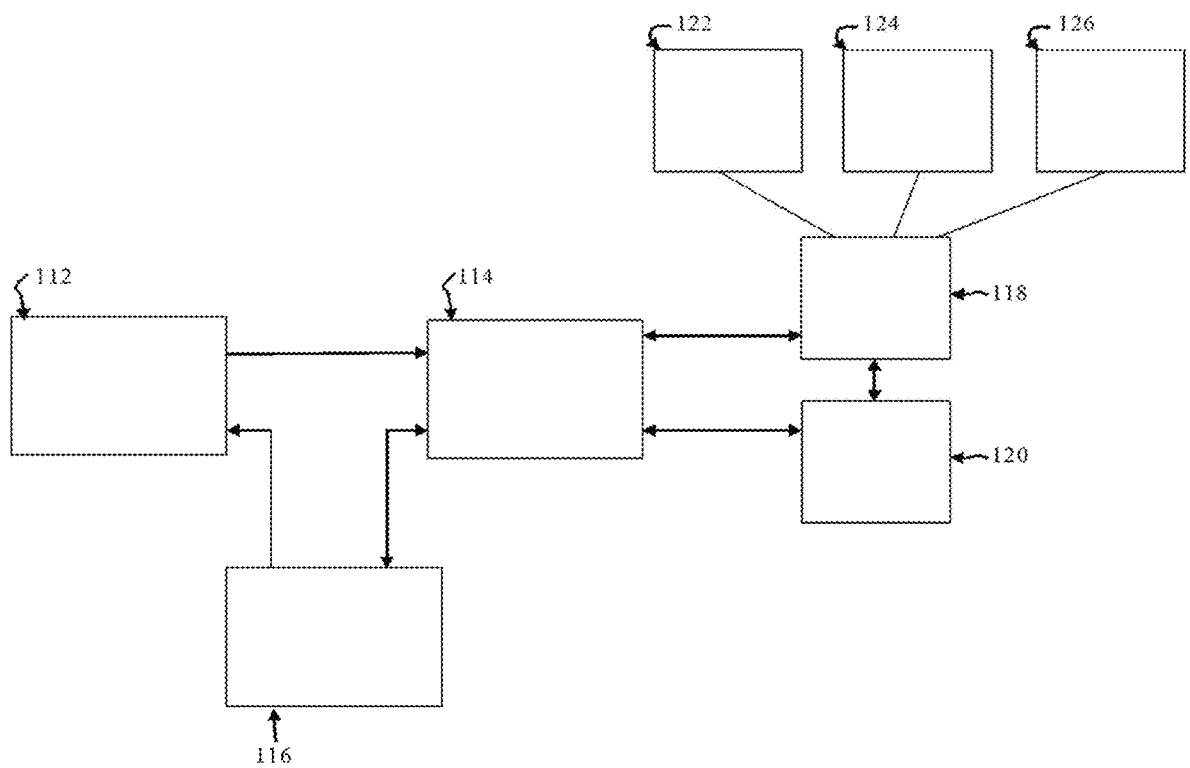
FIG. 3 shows a functional block diagram of an exemplary CT system.

FIG. 3 is a functional block diagram of an exemplary CT system, which includes a CT imaging apparatus 112 that operates under commands from user interface module 116 and will provide data to data processing module 114.

The CT imaging apparatus 112 captures a CT scan of the organ of interest. The CT imaging apparatus 112 typically includes an X-ray source and detector mounted in a rotatable gantry. The gantry provides for rotating the X-ray source and detector at a continuous speed during the scan around the patient who is supported on a table between the X-ray source and detector.

The data processing module 114 may be realized by a personal computer, workstation, or other computer processing system. The data processing module 114 processes the CT scan captured by the CT imaging apparatus 112 to generate data as described herein.

The user interface module 116 interacts with the user and communicates with the data processing module 114. The user interface module 116 can include different kinds of input and output devices, such as a display screen for visual output, a touch screen for touch input, a mouse pointer or other pointing device for input, a microphone for speech input, a speaker for audio output, a keyboard and/or keypad for input, etc. The data processing module 114 and the user interface module 116 cooperate to carry out the operations of the processes described herein.

The data processing module 114 includes one or more memory 118 and one or more processors 120. The memory 118 stores, among other things, the contrast enhanced volume dataset for the target organ, data segments, features extracted from analysis of the data segments, one or more VOA models. The memory 118 may also store one or more contrast enhanced volume datasets for the training organs, CAD related reference values, one or more VOA models, and the like. The memory 118 also stores software code that directs the one or more processors 120 to carry out the operations of the processes described herein. For example, the memory 118 may include an optical disc or other form of persistent memory such as a USB drive or a network server. The software code can be directly loadable into the memory of a data processing module 114 for carrying out the operations described herein.

In accordance with aspects herein, the imaging system has previously acquired and stored at least one CCTA dataset of an object of interest. Any imaging device capable of providing a CT scan can be used for this purpose. In accordance with aspects herein, the one or more processors 120 of the data processing module 114 implement a method for assessing a vessel obstruction, the method comprising: obtaining a volumetric image dataset for a target organ that includes a vessel of interest; extracting an axial trajectory extending along of a vessel of interest (VOI) within the volumetric image dataset; creating a three-dimensional (3D) multi-planer reformatted (MPR) image based on the volumetric image dataset and the axial trajectory of the VOI; and extracting a VOI parameter from the MPR utilizing a machine learning-based vessel obstruction assessment (VOA) model. In accordance with aspects herein, the one or more processors 120 of the data processing module 114 implement A method to train a vessel obstruction assessment (VOA) model, comprising: obtaining a training database that includes volumetric imaging datasets for multiple patients and corresponding coronary artery disease (CAD) related reference values, the volumetric image data sets being for a target organ that includes a vessel of interest, the CAD related reference values corresponding to one or more points along a vessel of interest within the corresponding imaging data set; for at least a portion of the volumetric image data sets and corresponding CAD related reference values, extracting an axial trajectory extending along of a vessel of interest (VOI) within the corresponding volumetric image dataset; creating a three-dimensional (3D) multi-planer reformatted (MPR) image based on the corresponding volumetric image dataset and the axial trajectory of the VOI, the MPR image extending along the axial trajectory of the VOI; and training a machine learning-based vessel obstruction assessment (VOA) model based on the MPR images, the training further comprising extracting, from the MPR images, features characterizing a CAD related parameter along the axial trajectory within the VOI.

The memory 118 may store memory configured to store a volumetric image dataset for a target organ that includes a vessel of interest. Optionally, the memory 118 may store a training database that includes volumetric imaging datasets for multiple patients and corresponding coronary artery disease (CAD) related reference values, the volumetric image data sets being for a target organ that includes a vessel of interest, the CAD related reference values corresponding to one or more points along a vessel of interest within the corresponding imaging data set.

The processors 120 performs extracting a CAD related parameter from the MPR image utilizing a machine learning-based vessel obstruction assessment (VOA) model. The processor 120 implement a training phase to train a machine learning-based vessel obstruction assessment (VOA) model based on the MPR images, the training further comprising extracting, from the MPR images, features characterizing a CAD related parameter along the axial trajectory within the VOI.

The operations of FIG. 2 can also be carried out by software code that is embodied in a computer product (for example, an optical disc or other form of persistent memory such as a USB drive or a network server). The software code can be directly loadable into the memory of a data processing system for carrying out the operations of FIG. 2.

In this example it is assumed that the imaging system has acquired and stored at least one CCTA dataset of an object of interest. Any imaging device capable of providing a CT scan can be used for this purpose.

The present application is particularly advantageous in coronary artery lesion parameters analysis based on CCTA dataset and it will mainly be disclosed with reference to this field, particularly for patient classification.

An embodiment of the present application is now disclosed with reference to FIG. 2. The therein-depicted steps can, obviously, be performed in any logical sequence and can be omitted in parts.

As described in step 201 of FIG. 2, an image dataset is obtained. Such an image dataset represents a volumetric image dataset for instance a single contrast enhanced CCTA dataset. This CCTA dataset can be obtained from a digital storage database, such as an image archiving and communication system (PACS) or a VNA (vendor neutral archive), a local digital storage database, a cloud database, or acquired directly from a CT imaging modality. During the CCTA imaging, a contrast agent was induced in the patient. Furthermore, the CCTA imaging can be ECG triggered.

Within step 202 of FIG. 2, the processors extract an axial trajectory extending along the vessel of interest. For example, the axial trajectory may correspond to a centerline extending along the vessel of interest. When the vessel of interest represents the coronary artery, the axial trajectory may correspond to the coronary centerline, in which case the processors extract the coronary centerline. The coronary centerline represents the center of the coronary lumen along the coronary section of interest. This can be a single coronary artery, a coronary bifurcation, or the full coronary tree. In case when the coronary section of interest includes one or more bifurcation(s), the coronary centerline will include bifurcation(s) as well but not its side branch. As described further by step 203, the centerline is used to create the MPR image. In case bifurcation and/or the coronary tree is analyzed, multiple centerline are extracted, as for example two coronary centerlines are extracted when analyzing one bifurcation; one coronary centerline identified by a proximal location to a distal location within the main branch of bifurcation, and one centerline identified by a proximal location to a distal location within the side branch of bifurcation. For the purpose of current application, it is not required that the extracted coronary centerline represents the center of the coronary lumen accurately. A rough estimation of the coronary centerline is sufficient, although the coronary centerline should not exceed the coronary lumen. The extraction of the coronary centerline can be performed manually or (semi)automatically. An example of a semiautomatic approach is described by Metz et al., "Semi-automatic coronary artery centerline extraction in computed tomography angiography data", proceedings/IEEE International Symposium on Biomedical Imaging: from nano to macro, May 2007. An example of an automatic coronary centerline extraction method is described by Wolterink et al. in which machine learning is utilized to automatically extract the coronary centerline in "Coronary artery centerline extraction in cardiac CT angiography using a CNN-based orientation classifier", Med Image Anal. 2019 January; 51:46-60. The method extracts, after placement of a single seed point in the artery of interest, the coronary centerline between the ostium and the most distal point as visualized in the CCTA image dataset.

Figure 4A:
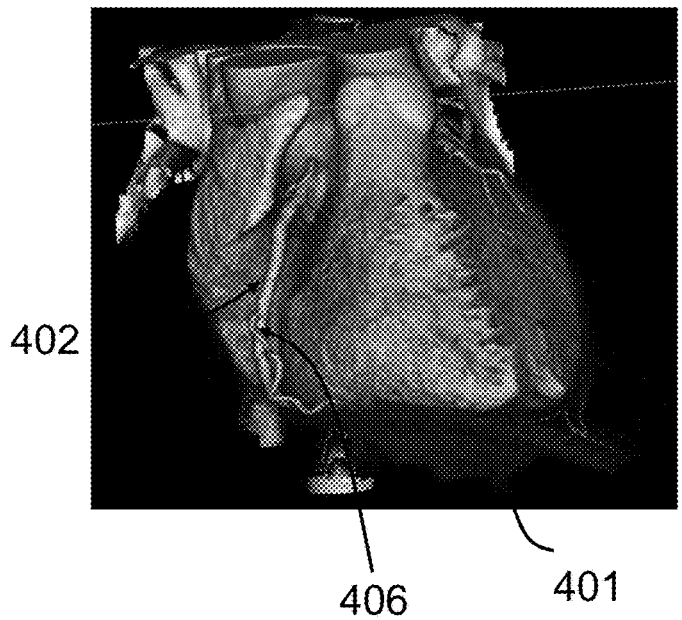
FIGS. 4a-4e illustrate the creation of a volumetric MPR image.

Within step 203 of FIG. 2, a three-dimensional (3D) multi-planar reformatted (MPR) image is created of the coronary artery of interest. FIGS. 4a-4d provide an illustration of the creation of a volumetric (3D) MPR image, further called an MPR image. Image 401 of FIG. 4a shows a volumetric rendering of a CCTA dataset (FIG. 2, 201), in which the right coronary artery 402 is selected as an example to create an MPR image. With respect to MPR, there is a distinction between straight MPR and curved MPR. Both for the straight MPR as well for the curved MPR the extracted axial trajectory (e.g. centerline) is used to create isotropic MPR image from the obtained image dataset 201. The resolution of the MPR image is predefined and is for example 0.3 mm. The MPR image can also be created in a non-isotropic way.

Figure 4D:
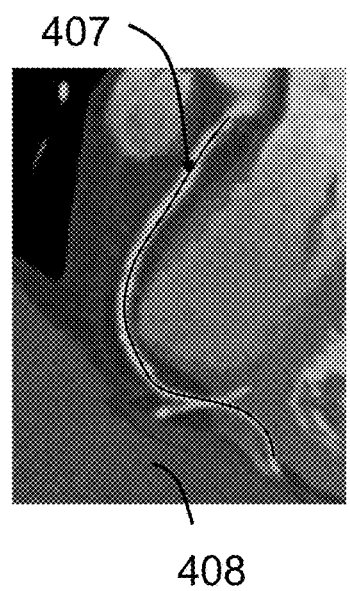
Figure 4B:
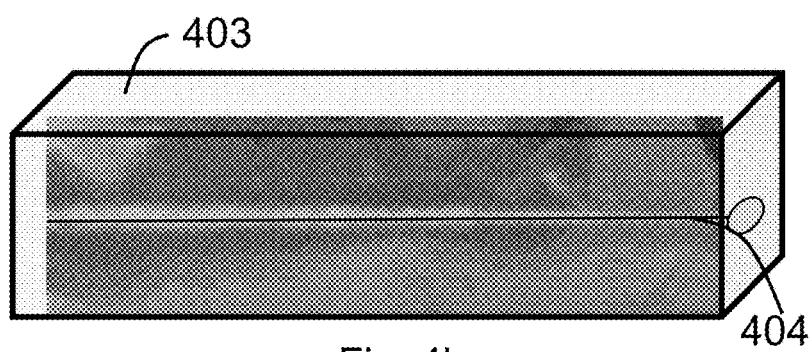
Figure 4C:
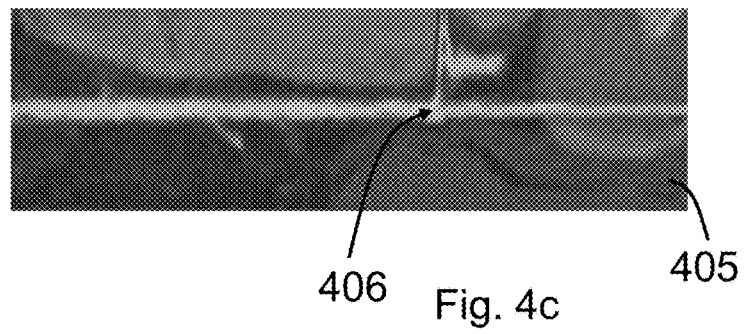
Figure 4E:
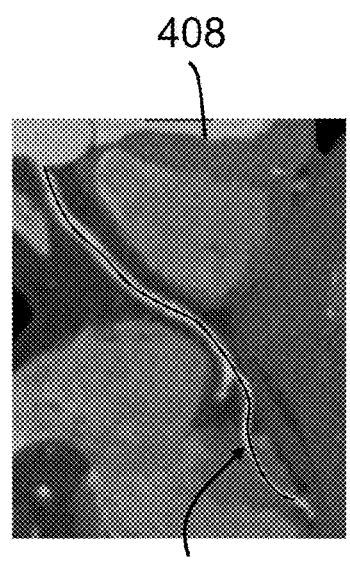

A straight MPR reformats the image towards a cuboid image 403 along the extracted axial trajectory (e.g. coronary centerline) 402 in such a way that the coronary centerline is in the center of the cuboid 404. Image 403 of FIG. 4b illustrates the cuboid resampled image (straight MPR) and one 'slice' is visualized within the cuboid resampled image for easy interpretation. Image 405 of FIG. 4c shows a one 'slice' of the same resampled image, but the visualization plane is rotated around the centerline 404, to illustrate the visualization of the coronary bifurcation (406) within the extracted right coronary artery. A curved MPR image is reconstructed along the curved course of the coronary centerline. Images 408a and 408b of FIGS. 4d and 4e shows two examples of a curved MPR image and visualized as a single 'slice', in which the slice orientation refers to a curved plane which can be rotated along the curved coronary artery. Again, this is just for visualization purpose, the application will use the full 3D straight or curved MPR image. The advantage of a curved MPR image is that the curvature or tortuosity of the extracted centerline can be taken into account within the described machine learning network architectures within this application.

Within step 204 of FIG. 2, the coronary parameters are extracted by utilizing a machine learning based Vessel Obstruction Assessment (VOA) model. Within current application, coronary plaque type, anatomical coronary lesion severity and functionally significant coronary lesion severity are assessed by utilizing machine learning based VOA models on the MPR image as a result of step 203 of FIG. 2. The machine learning approach for the assessment of functionally significant coronary lesion severity is slightly different as compared to the machine learning method for the detection of plaque type and anatomical coronary lesion severity and is further described by the corresponding flow charts within current application. Moreover, a distinction is made between the learning phase and the prediction phase within current application and is described in more detail in the description of the different machine learning methods. Within the learning phase (or training phase), the machine learning model is trained. This involves training the parameters of the selected model, or also called the network architecture, by using reference standard (205 of FIG. 2). The reference standard is a database which contains data of multiple patients. Each set within the database contains for each patient a) contrast enhanced CT image datasets (201 represents reference image sets during the training phase) and corresponding b) CAD related reference values. For example, the CAD related reference values may represent at least one of the plaque type, anatomical stenosis severity, invasively measured fractional flow reserve, and/or other hemodynamic indices. As a further example, the hemodynamic indices can represent indices used to assess functionally significant coronary artery obstruction(s) such as coronary flow reserve, instantaneous wave-free ratio, hyperemic myocardium perfusion, index of microcirculatory resistance and pressure drop along a coronary artery.

After training the machine learning model, step 204 of FIG. 2 is configured to predict the coronary plaque type, and/or anatomical stenosis severity and/or the functional significance of the coronary of interest based on analysis of the MPR image as a result of step 204. Within the prediction phase, unseen image data is used (201) and step 205 of FIG. 2 is detached.

Figure 5B:
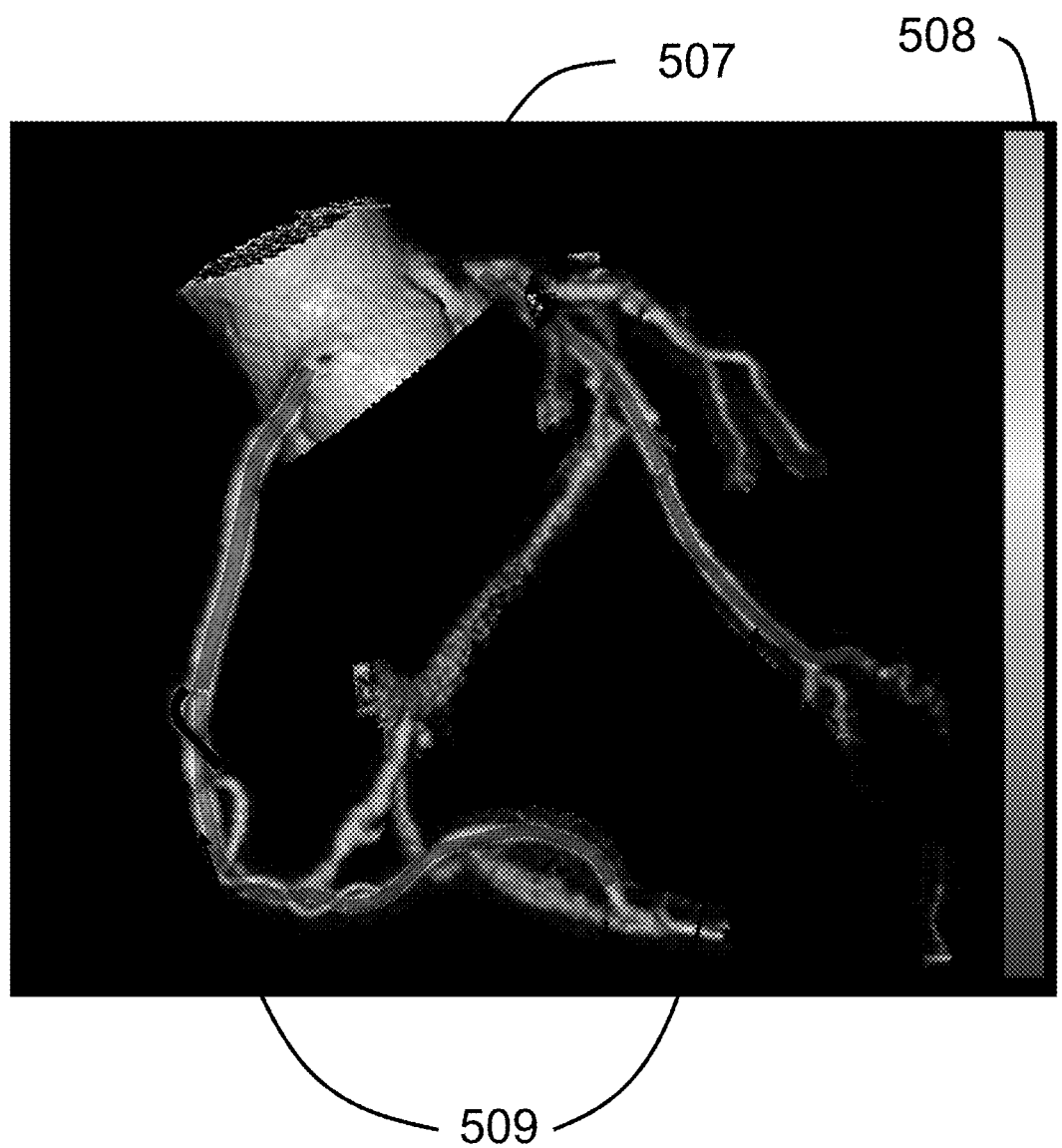
FIG. 5b shows an alternative example on how the results obtained by an embodiment of present application can be presented within a 3D rendered image.
Figure 6:
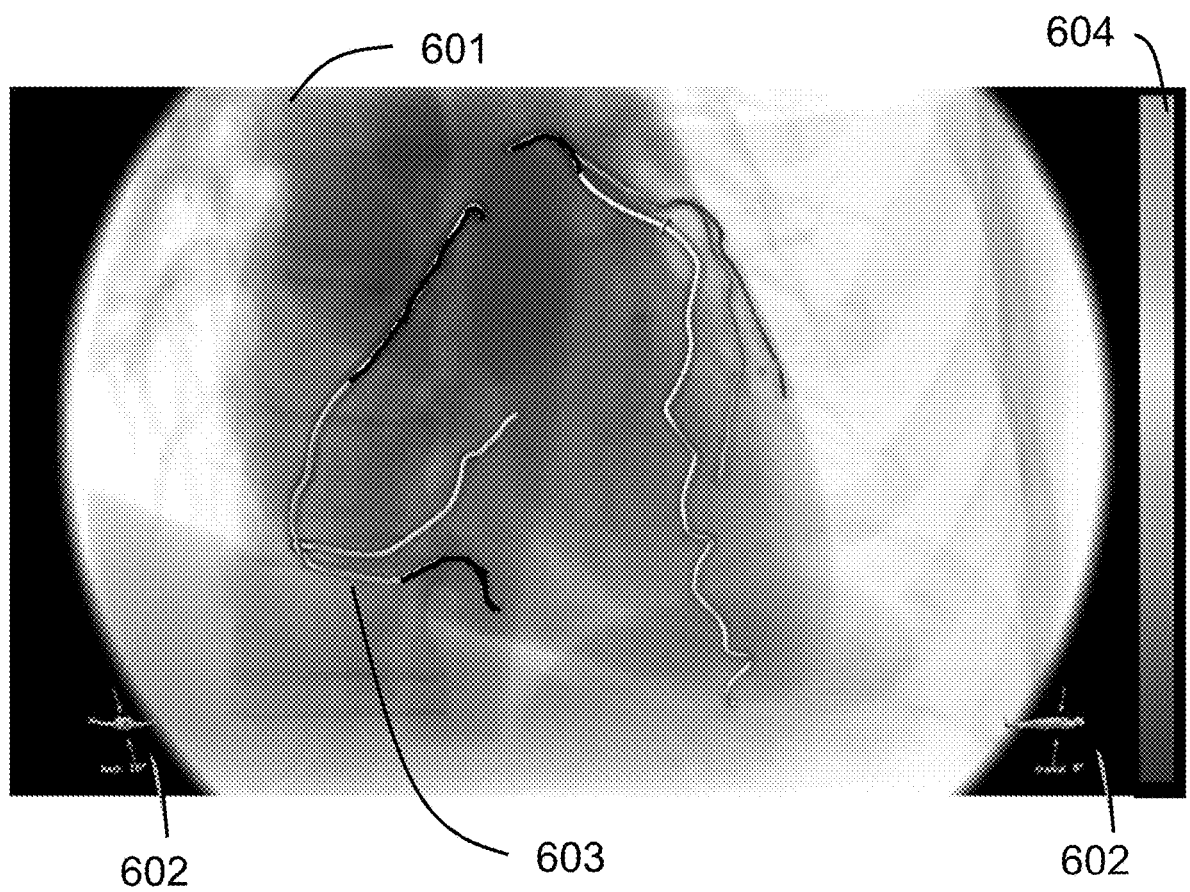
FIG. 6 shows an example on how the results obtained by an embodiment of present application can be presented in a way that mimics an x-ray angiographic image familiar as being created during a catheterization procedure.

The output (step 206 of FIG. 2) is a prediction of the coronary plaque type, and/or anatomical stenosis severity and/or the functional significance of lesion(s) within the coronary of interest. This result can be presented to the user in various ways. FIGS. 5a(i)-5a(v) and FIG. 5b shows some examples of the presentation of the results to the user. Image 501 of FIG. 5a(i) represents the MPR image as a result of step 203 of FIG. 2. Image 502 of FIG. 5a(ii) shows the plaque type classification as a color or grey value superimposed on the MPR image, in which the colors represent different plaque types (e.g. no-plaque, calcified plaque, non-calcified plaque or mixed plaque). Image 503 of FIG. 5a(iii) shows the anatomical stenosis severity superimposed as a color or grey value on the MPR image, in which the colors represent different labels of anatomical stenosis severity. Within Image 503, three anatomical stenosis severity classes are visualized, no-stenosis, non-anatomical significant stenosis (with <50% luminal narrowing) or anatomical significant stenosis (with >50% luminal narrowing). Image 504 of FIG. 5a(iv) shows the FFR value along the MPR image, in which the y-axis represents the estimated FFR value and the x-axis the location along the length of the coronary of interest which corresponds to the x-axis of the MPR image 501. Various other ways of visualization can be used, for instance the results can be superimposed on the curved MPR, on the orthogonal views or the results can be visualized on the volumetric rendering of the image dataset (201 of FIG. 2) as shown by image 505 of FIG. 5a(v) in which 506 illustrates a color-coded result of for instance the FFR value along the coronary centerline. Note that in Image 505, the coronary centerlines 506 are visualized to appeal the coronary lumen by using volume rendering techniques. FIG. 5b shows another example of visualization the results. Image 507 is a volumetric rendering of only the coronary arteries including a small part the ascending aorta in which the left and right coronary artery emanate from the aorta. Superimposed on the rendered coronary arteries within 507, a color or grey value is visualized (509) which represents for instance the numerical FFR value and 508 provides the color legend to map the color or grey value to a (numerical) value. Another visualization approach is presented by FIG. 6. In this figure the results are shown within a simulated angio view. A simulated angio view is an image which mimics an x-ray angiographic image of the coronaries as view by a particular angulation of the c-arm, as for instance disclosed by U.S. Pat. No. 9,008,386B2 and U.S. Ser. No. 10/192, 352B2. Image 601 of FIG. 6 shows such a simulated angio view in which the angulation (602, rotation angle of the c-arm and angulation rotation angle of the c-arm) can be controlled by the user. 603 shows the extracted centerline as a result of step 202 of FIG. 2, on which the color or grey value represent for instance the FFR value and 604 provides the color legend to map the color or grey value to a (numerical) value.

Figure 7:
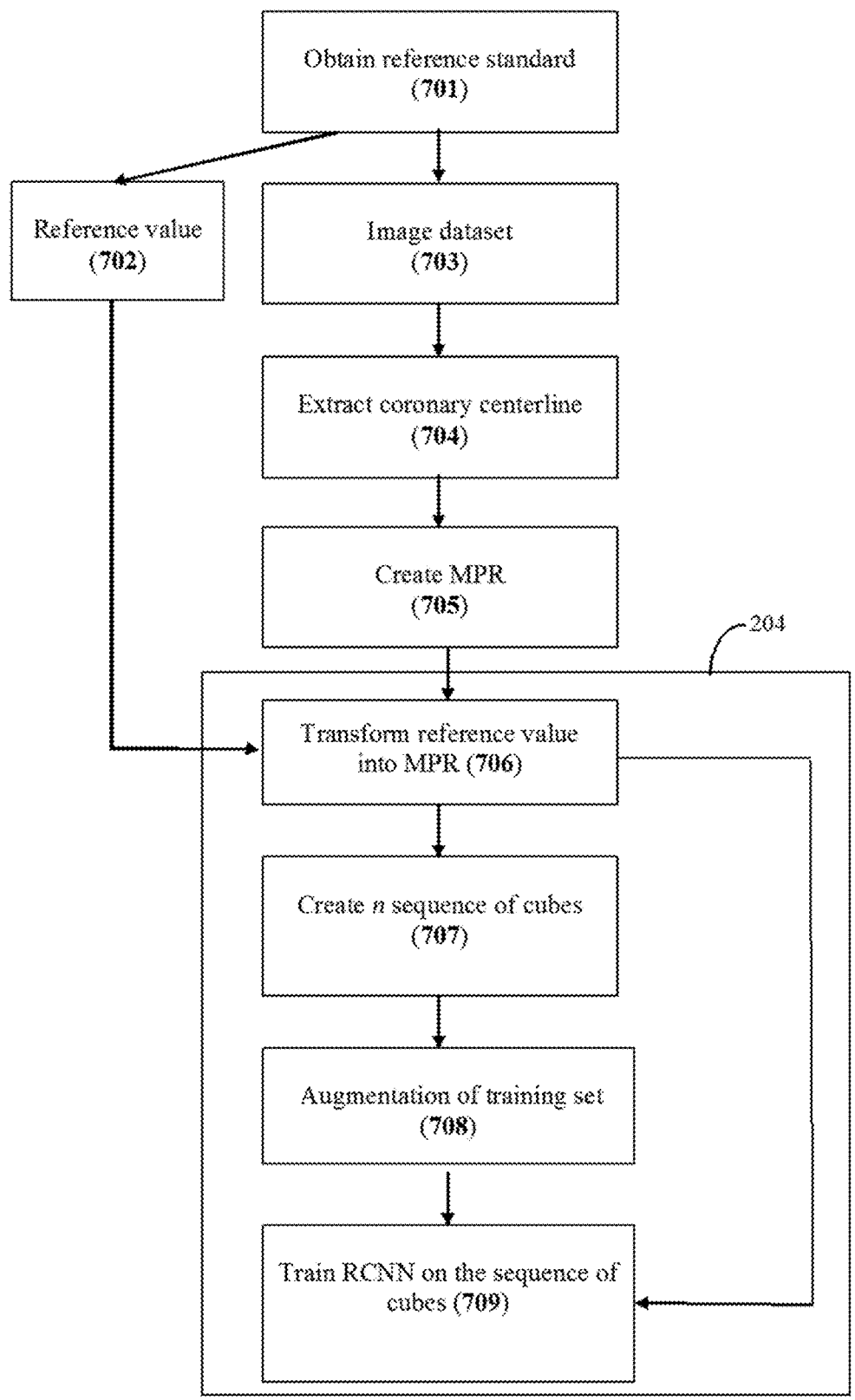
FIG. 7 shows a flowchart of the generation of the machine learning RCNN classification model as performed by the training phase.

FIG. 7 illustrates a framework for training the machine learning model to extract coronary parameters within the MPR image as described by step 204 of FIG. 2. FIG. 7 illustrates the training phase of the system to detect coronary plaque type, anatomical stenosis severity and functionally significant coronary stenosis severity. In step 701 of FIG. 7 the reference standard is obtained as used to train the machine learning model. For example, the processor may obtain a training database that includes volumetric imaging datasets for multiple patients and corresponding coronary artery disease (CAD) related reference values. The volumetric image data sets may be for a target organ that includes a vessel of interest. The CAD related reference values corresponding to one or more points along a vessel of interest within the corresponding imaging data set. The reference standard is a database which contains data of multiple patients. Each set within this database contains for each patent a) contrast enhanced CT datasets step 703 and corresponding b) CAD related reference values. For example, the CAD related reference values may represent at least one of the plaque type, anatomical stenosis severity, invasively measured fractional flow reserve, and/or other hemodynamic indices. As a further example, the hemodynamic indices can represent indices used to assess functionally significant coronary artery obstruction(s) such as coronary flow reserve, instantaneous wave-free ratio, hyperemic myocardium perfusion, index of microcirculatory resistance and pressure drop along a coronary artery.

The reference plaque type contains annotation of different types of coronary plaque such as no-plaque, calcified plaque, non-calcified plaque, or mixed plaque.

The reference of anatomical stenosis severity contains different stenosis grades, for example grade 0 (no luminal narrowing), grade 1 (0-25% luminal narrowing), grade 2 (25-50% luminal narrowing), grade 3 (50-75% luminal narrowing) grade 4 (75-100% luminal narrowing).

Within current application the invasively measured fractional flow reserve is preferably measured along the coronary of interest, resulting in an invasively measured fractional flow reserve value at each position along the coronary centerline. This can be obtained by performing a pullback during the measurement of the fractional flow reserve. In the catheterization laboratory, the interventional cardiologist or physician places the FFR wire at the distal location within the coronary of interest. During automatic or manual pullback, the FFR value is continuously measured until the FFR wire reaches the coronary ostium.

In step 704 of FIG. 7, the processor extracts an axial trajectory extending along of a vessel of interest (VOI) within the corresponding volumetric image dataset. For example, the coronary centerline may be extracted which represent the center of the coronary lumen along the coronary section of interest. This step may be implemented in a manner substantially similar to step 202 of FIG. 2.

In step 705 of FIG. 7, the processor creates a three-dimensional (3D) multi-planer reformatted (MPR) image based on the corresponding volumetric image dataset and the axial trajectory of the VOL The MPR image extends along the axial trajectory of the VOL For example, a multi-planer reformatted (MPR) image may be created along the extracted coronary section as a result from step 704. Step 705 of FIG. 7 may be implemented in a manner substantially similar to step 203 of FIG. 2.

In step 706 of FIG. 7, the operations ensure that the CAD-related reference values 702 are aligned to the spatial coordinates of the MPR image. In case the CAD-related reference values (e.g. manual annotation of plaque type, anatomical lesion severity, functional lesion severity such as for instance FFR) are obtained by using the MPR image as a result from step 705, this step may be skipped. When the CAD-related reference values are obtained, for instance by annotation using orthogonal views of the contrast enhanced CT datasets (step 703), this step transforms the annotation into the MPR view. Such a transformation is performed by using the extracted centerline as a result of step 704.

To ensure that the fractional flow reserve values along the coronary artery as measured in the catheterization laboratory (e.g., pullback FFR reference values) are aligned to the spatial coordinates of the MPR image, a co-registration is performed between the image dataset 703 and the invasively measured pullback FFR. To allow co-registration of the pullback FFR measurement with the CT dataset, pullback motion information is obtained indicative of the pullback rate or speed during withdrawal of the FFR wire from an FFR wire start location (e.g., distal position in the coronary artery) to an FFR wire end location (e.g., proximal position in the coronary artery or the ostium of the coronary artery). The pullback motion information can be obtained by measuring the longitudinal motion of the FFR wire during pullback. The measurement may be obtained in various manners, such as by means of a motion measurement system, or for instance by utilizing a motorized pullback device that maintains a constant pullback speed. The one or more processors of the system utilize the time required to pullback the FFR wire and the pullback speed to calculate a length of a pullback distance. In order to align the pullback FFR reference values into the MPR image, the one or more processors transform the length of the pullback distance to the image dataset used in 703.

Figure 8A:
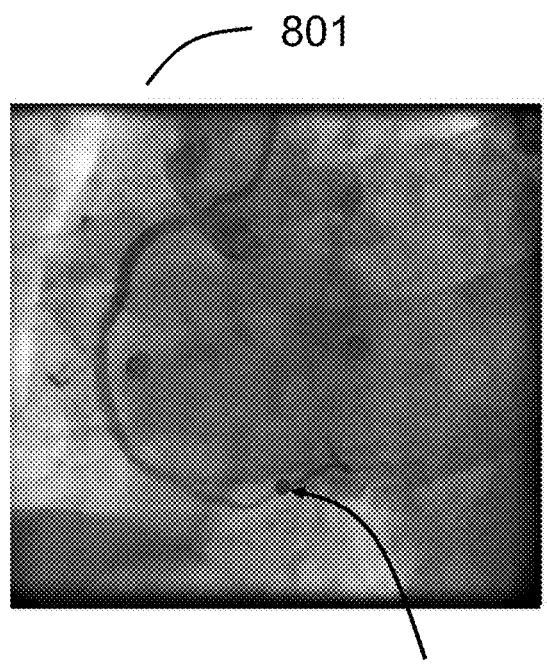
FIGS. 8a-8c show a schematic illustration of a co-registration method of pullback FFR reference values with the CCTA image dataset.
Figure 8B:
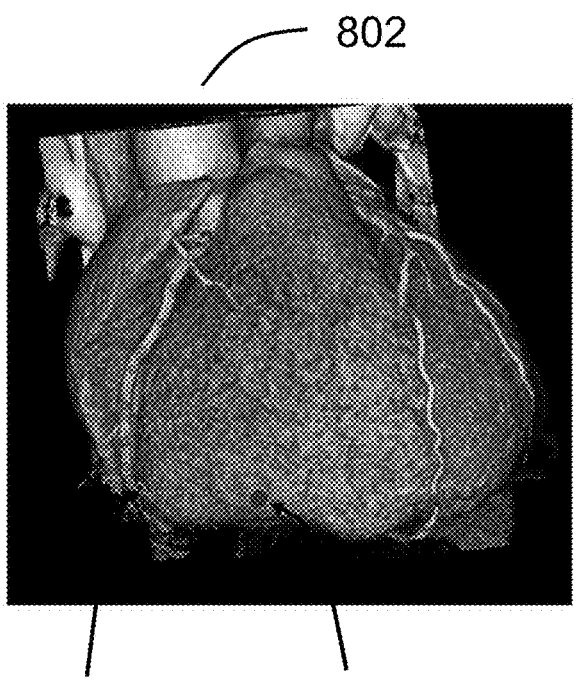
Figure 8C:
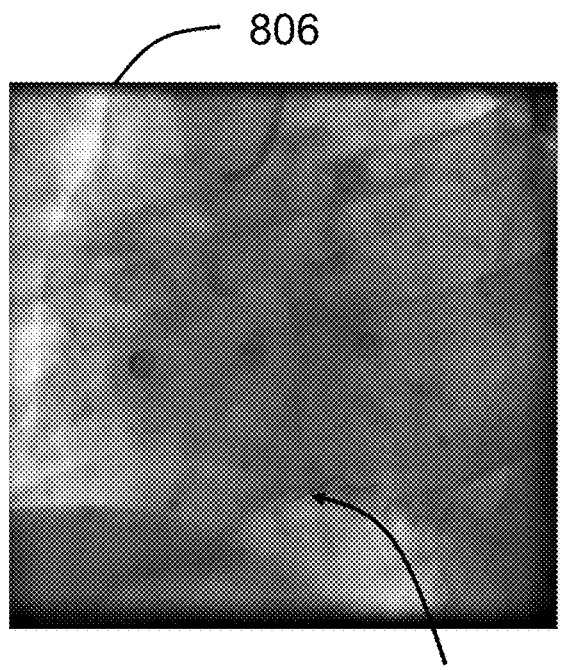

FIGS. 8a-8c, collectively, provide a schematic illustration of a co-registration method of a pullback FFR reference value (e.g., pullback distance) with the CCTA image dataset. Image 801 of FIG. 8a shows an x-ray coronary angiographic image as acquired within the catheterization laboratory. Image 802 of FIG. 8b shows a volume rendered CCTA image belonging to the same patient. Image 806 of FIG. 8c shows an x-ray fluoroscopic image without contrast liquid present.

The x-ray coronary angiographic image 801 of FIG. 8a illustrates the right coronary artery with an FFR pressure wire inserted therein to a desired distal position at which a pressure sensor may obtain first/distal pressure measurements of interest. The dot 803 indicates a location of the pressure sensor on the FFR pressure wire when located at the distal position within the coronary artery before pullback on the x-ray angiographic image. The position denoted by dot 803 may also be referred to as a distal pressure sensor position. The distal position of the pressure sensor (and the entire FFR pressure wire) is easily identifiable on x-ray fluoroscopic image (without contrast liquid present, 806) due to the radiopaque marker on the FFR wire 807 (as shown in the image 806 of FIG. 8c) enabling to localize the pressure sensor on the FFR wire.

Image 802 of FIG. 8b shows a volume rendered CCTA image (belonging to the same patient in which the pullback FFR reference values are obtained). In the image 802, the right coronary artery 804 is identified for instance as a result from step 704 of FIG. 7. Co-registration of the pullback FFR reference values is performed by identifying the location of the FFR pressure wire before pullback within the CCTA dataset (805), for instance manually identifying supported by anatomical landmarks such as bifurcation location, and align the FFR values by matching the lengths (length of the 3D extracted centerline with the length of the FFR pullback). The identification of the location of the FFR pressure wire before pullback within the CCTA dataset can also be performed by registration of the x-ray angiographic image with the CCTA dataset, as for instance by using the method of Baka et al. "Oriented Gaussian Mixture Models for Nonrigid 2D/3D Coronary Artery Registration", IEEE Trans Med Imaging. 2014 May; 33(5):1023-34. Baka et al describes a method to register a 2D x-ray angiographic image to a 3D volumetric image dataset (CCTA) by using a Gaussian mixture model (GMM) based point-set registration technique. Since the location of the pressure sensor (807) on the FFR wire can be easily performed using x-ray fluoroscopic image (806) by means of image processing techniques, the transformation of this location into the CCTA image data (805) is straightforward using the deformation field resulting from the 2D/3D registration as described by Baka et al.

Returning to FIG. 7, in step 707, the processors train a machine learning-based vessel obstruction assessment (VOA) model based on the MPR images. Among other things, the training comprises extracting, from the MPR images, features characterizing a CAD related parameter along the axial trajectory within the VOI. For example, the CAD related parameter values may represent at least one of the plaque type, anatomical stenosis severity, invasively measured fractional flow reserve, and/or other hemodynamic indices. As a further example, the hemodynamic indices can represent indices used to assess functionally significant coronary artery obstruction(s) such as coronary flow reserve, instantaneous wave-free ratio, hyperemic myocardium perfusion, index of microcirculatory resistance and pressure drop along a coronary artery.

For example, in connection with the training, the processors generate a sequence of cubes from the MPR image which are used to train the network as described further in step 709. A sequence of cubes is created within sections were the CAD-related reference value is available as a result from step 706, resulting in a sequence of n cubes for each section. The term section in this context refers to a continuous part within the MPR image in which the CAD-related reference value is available and not a specific anatomical segment of the coronary artery. This allows that the CAD-related reference value do not need to cover the full length of the MPR image. For instance, the annotation of plaque types or grade of coronary luminal narrowing needs only to be present in coronary regions in which there truly is a coronary plaque. In regions were no annotation of plaque type or lesion obstruction is available, the system can either automatically mark these regions as 'no coronary plaque' or 'no anatomical coronary obstruction present' or ignore them in the training phase.

Figure 9A:
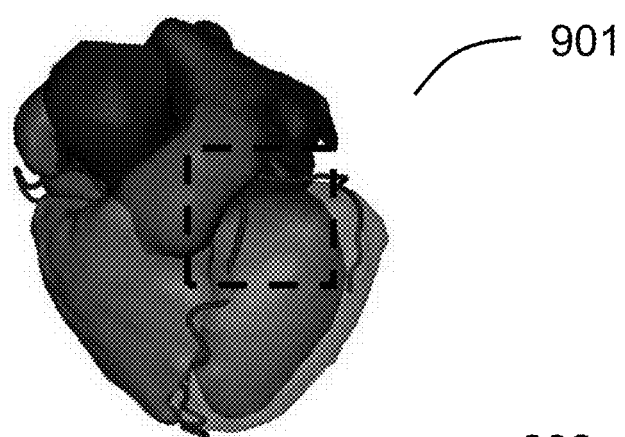
FIGS. 9a-9d show a schematic illustration for the generation of a sequence of cubes within an MPR image.
Figure 9B:
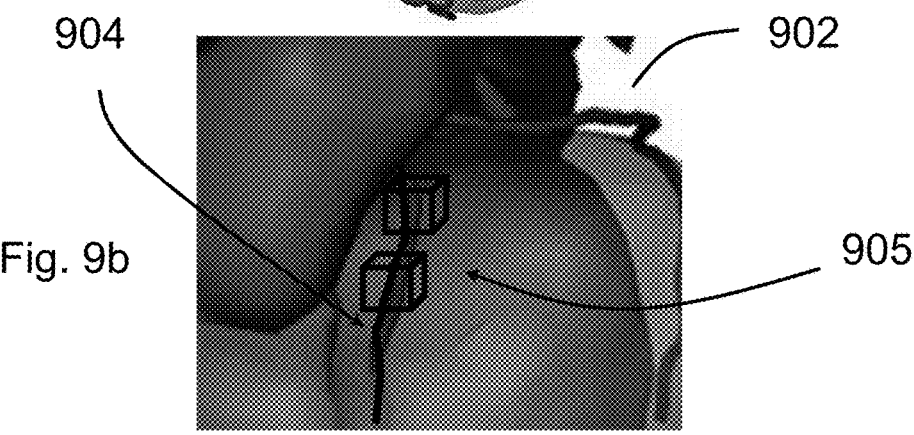
Figure 9C:
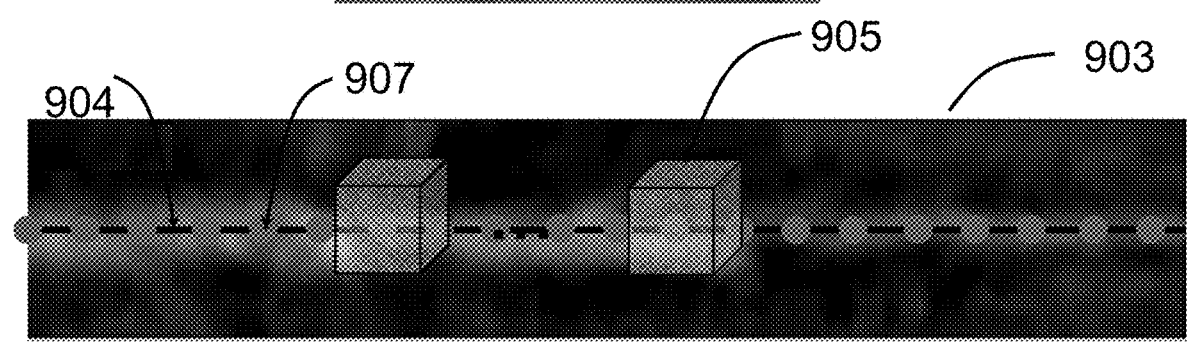
Figure 9D:
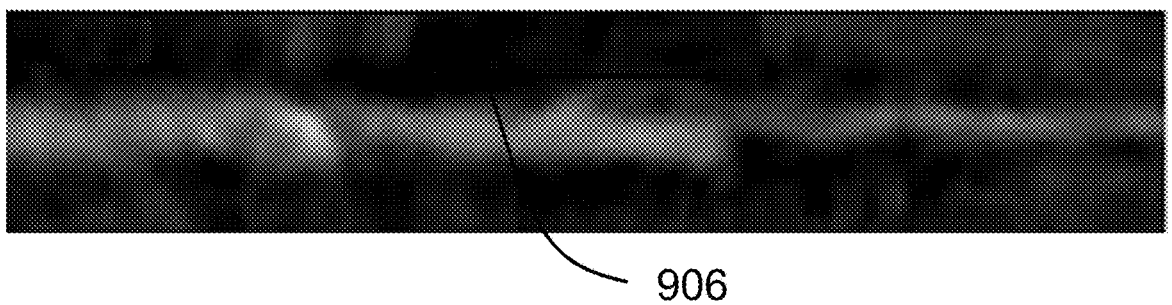

FIGS. 9a-9d, collectively, provide a schematic illustration of a process to generate the sequence of cubes within a section. Image 901 of FIG. 9a shows a 3D view of the heart. Image 902 of FIG. 9b is a zoomed-in view of the rectangle within image 901. Within image 902, the extracted axial trajectory (in the example a coronary centerline tree) is shown (904). The coronary centerline exists of a number of points (907). Image 903 of FIG. 9c shows the straight MPR image (as a result of step 704 of FIG. 7) created using the centerline 904. FIG. 9d shows a section (906) of image 903 where a sequence of cubes is created which covers a small part of the MPR image. The size of the cubes is defined so that it contains the whole arterial lumen and the vicinity of the artery that may be needed in case of positive remodeling. Positive remodeling refers to the outwards direction of atherosclerotic plaque growth. CAD is currently defined as clinically significant when luminal narrowing is present, typically at the 50% diameter reduction threshold. However, in early atherosclerosis the first arterial changes include of compensatory enlargement of both the outer wall of the vessel as well as the lumen, termed compensatory enlargement or positive remodeling. Each cube is for instance 25×25×25 voxels, but other cube sizes are possible. The distance between the cubes (stride) is m centerline points (m is for instance 5 centerline points in case the distance between the centerline points is maximum 1 voxel, but other stride values are possible). The maximum number of cubes is defined by the amount of centerline points, or length, of the MPR image. In a preferred embodiment the maximum number of cubes is limited to the longest annotated plaque type section, which is for instance 25. In case multiple sections are present in the MPR image, also multiple (n) sequence of cubes are generated.

Returning to FIG. 7, in step 708, the training data is augmented. Prior to training several data augmentation techniques are utilized to increase the training set.

Figure 10:
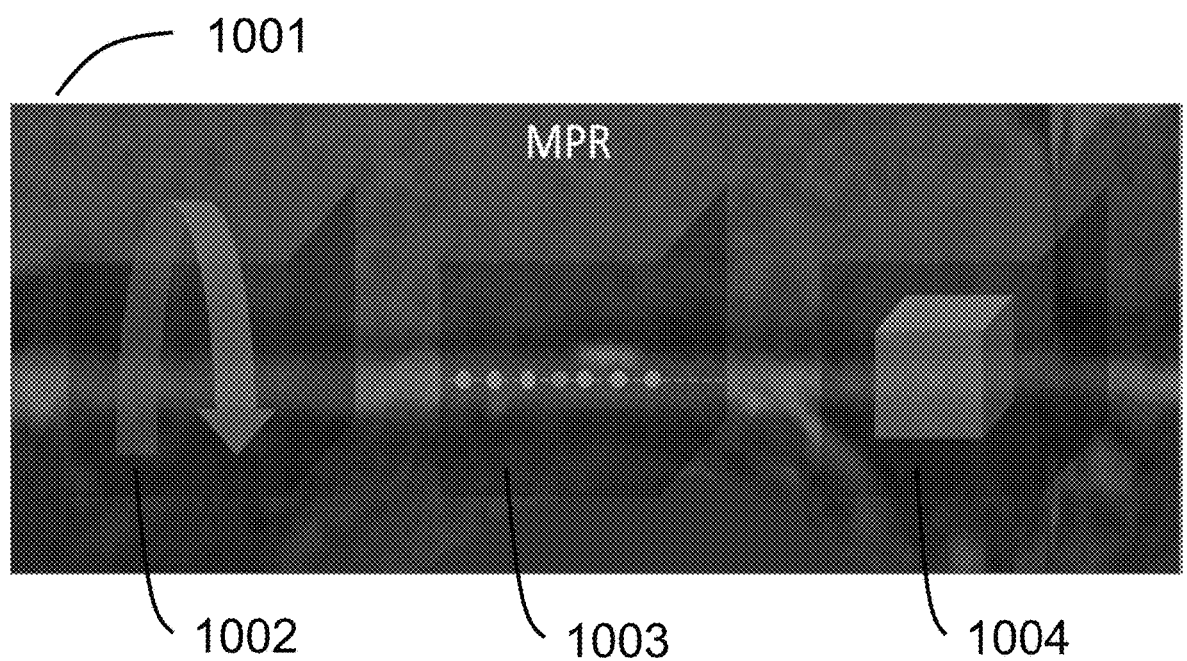
FIG. 10 shows three augmentation methods used for augmentation.

FIG. 10 shows three example augmentation methods used; however different augmentation methods can be performed. Referring to FIG. 10, 1002 represents rotation of the cubes within the MPR image, rotation takes place around the MPR centerline (see 904 of FIG. 9b). Such a rotation makes the network invariant to rotations around the coronary centerline, random rotations between 0 and 360 degrees around the coronary centerline are applied to the cubes of the sequences. The second augmentation method (1003) makes the network invariant to slight inaccuracies in the CAD-related reference values (e.g. annotations of the points defining the plaque type within the section, annotation of the anatomical lesion severity, small errors in registration of the pullback FFR). A sequence of a section is varied by randomly choosing centers of cubes with a stride between for instance 5±3 voxels along the MPR centerline. The third augmentation method (1004), makes the network robust to possible inaccuracies in the extraction of the coronary artery centerline, the center of each cube is randomly shifted around its origin by for instance±2 voxels, in any direction (inside cube 1004). The result of step 708 significantly increases the number of sequences as a result of step 707, which are used for training the network as described below by step 709.

In step 709 of FIG. 7, the one or more processors implement the machine learning network architecture and training of the network. The network architecture is based on recurrent convolutional neural network (RCNN) which is employed to analyze a sequence of cubes (step 707), representing the vicinity along the extracted centerline in an MPR image. RCNN is typically, but not limited to, built from a convolutional neural network (CNN) with a recurrent neural network (RNN) connected in series to analyze a sequential input.

RCNN's have been successfully used for video sequence recognition as for instance described by Donahue et al., "Long-term recurrent convolutional networks for visual recognition and description" in Proceedings of the IEEE Conference on Computer Vision and Pattern Recognition, 2015, pp. 2625-2634. RCNN's are a very important variant of neural networks heavily used in language processing (Mulder et al, "A survey on the application of recurrent neural networks to statistical language modeling", Computer Speech & Language, vol. 30, no. 1, pp. 61-98, 2015). In a general neural network, an input is processed through a number of layers and an output is produced, with an assumption that two successive inputs are independent of each other. This assumption is however not true in a number of real-life scenarios. For instance, if one wants to predict the next word in a sequence or to predict the next frame within a video sequence, it is imperative that dependence on previous observations is considered. RCNNs are called recurrent because they perform the same task for every element of a sequence, with the output being depended on the previous computations and then the recurrent part mutually processes the previous output. Another way to think about RCNNs is that they have a "memory" which captures information about what has been calculated so far. Though the input is static, the activities of RCNN units evolve over time so that the activity of each unit is modulated by the activities of its neighboring units. This property enhances the ability of the model to integrate the context information, which is important for analyzing a sequential input.

In accordance with embodiments herein, the employed RCNNs connect a CNN with an RNN in series to analyze a sequential input. The CNN extracts image features for each cube (or at least a portion of the cubes) of the sequence of cubes independently, and these extracted image features are then fed to the RNN that analyzes the relevant sequential dependencies in the whole sequence.

Figure 11:
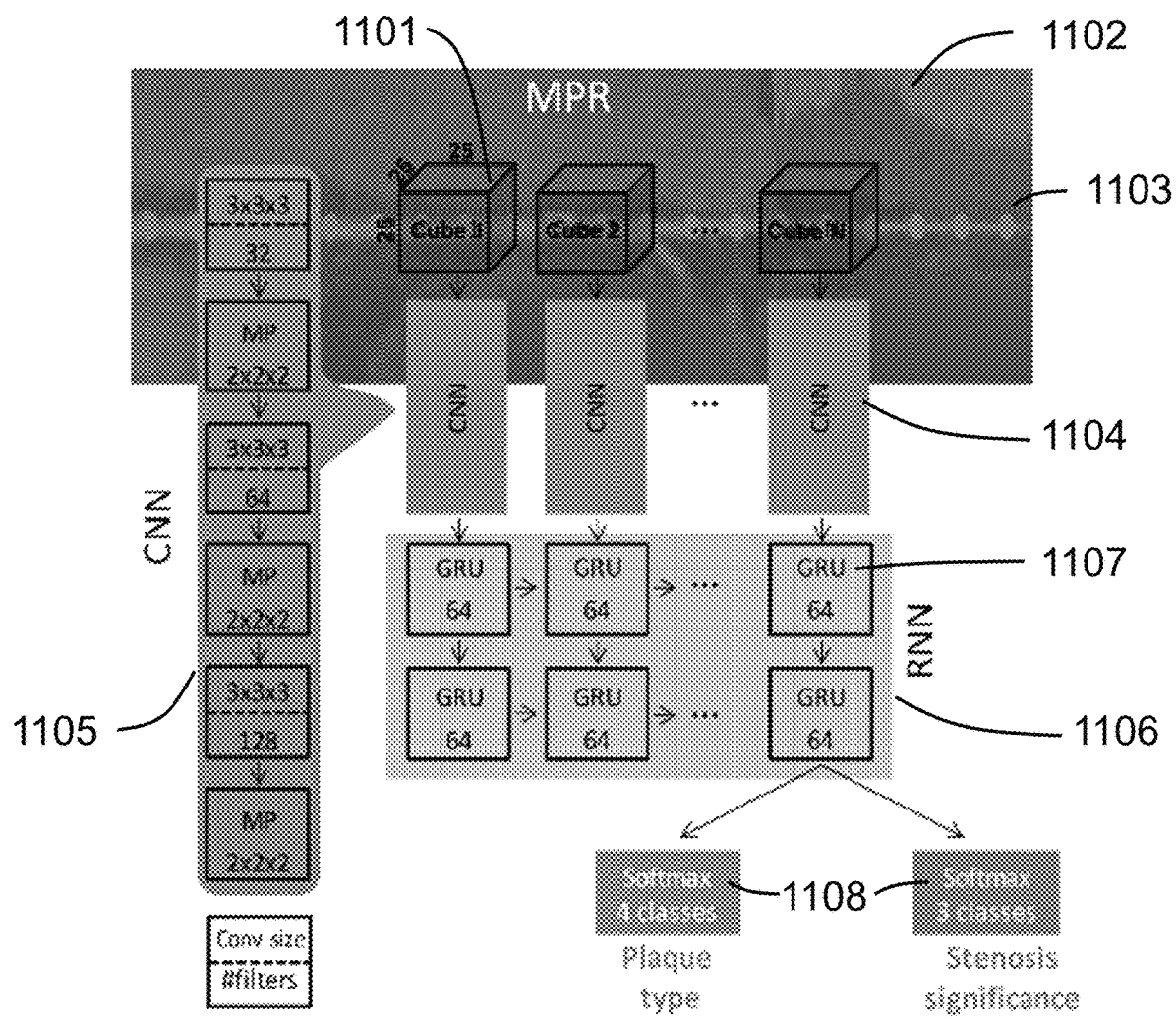
FIG. 11 shows an example of a RCNN architecture to detect coronary plaque type and anatomical lesion severity along a coronary artery of interest.

FIG. 11 provides an example of a RCNN network to detect coronary plaque type and anatomical stenosis severity. The RCNN network architecture presented in FIG. 11 should be considered as an example, and other RCNN network architectures or variants can be deployed. The input of the network is a sequence of cubes (1101) extracted from the MPR image (1102), along the vessel (e.g., artery) centerline (1103). Each cube is analyzed by a three dimensional (3D) CNN (1104). The CNN includes three convolutional layers with kernels of 3×3×3 elements, with 32, 64, 128 filters, respectively as shown by 1105. Each convolutional layer is followed by a 2×2×2 max-pooling (MP) layer and batch normalization which accelerates the training (Loffe et al, "Batch normalization: Accelerating deep network training by reducing internal covariate shift", in Proceedings of the 32nd International Conference on Machine Learning, 2015, pp. 448-456). The features extracted by the CNN are fed to the RNN (1106). The RNN includes 2 layers of 64 Gated Recurrent Units (GRUs) each (1107). Rectified linear units (ReLU) (Glorot et al, "Deep sparse rectifier neural networks", International Conference on Artificial Intelligence and Statistics, 2011, pp. 315-323) are used in both CNN and RNN layers as activation functions, except for the output layer of the RNN. Other parameters can be used, for instance, but not limited to, different kernel sizes and numbers, different convolutions, different dilations, different pooling, different type of recurrent units as well as other RCNN architectures and activation functions. Furthermore, the input size of the CNN can be different as well of the use of a 4D input voxel data for instance to support multiphase CCTA datasets. The input image can be even a higher dimensional image, for instance n-dimensional to support multi-energy and/or multiphase CCTA dataset. To perform both classification tasks simultaneously (plaque type classification and anatomical lesions severity classification), for instance but not limited to, the output of the last layer of the RNN is fed into two separate multi-class softmax classifiers (1108). Also the output of other RNN layers or GRU units can be used. The first classifier has four output units for detection of plaque type and characterization of its type (no-plaque, non-calcified, mixed, calcified). The second classifier has three output units for detection of stenosis and determination of its anatomical significance (no-stenosis, non-significant stenosis, significant stenosis). The amount of output units of the softmax classifiers can be different as well, and will depend on the amount of classes within the CAD-related reference values. For instance, the anatomical lesion severity can be classified by x-grades, then the corresponding softmax classifier equals the same number (x) of output units. For example, five grades; grade 0 (no luminal narrowing), grade 1 (0-25% luminal narrowing), grade 2 (25-50% luminal narrowing), grade 3 (50-75% luminal narrowing) grade 4 (75-100% luminal narrowing).

The RCNN network of FIG. 11 is trained in a supervised manner with mini-batches and the categorical cross-entropy was used as loss function of each softmax classifier and a L2 regularization was used for all layers in the network. An L2 regularization is also known as least squares error regularization. It is basically minimizing the sum of the square of the differences between the target values and the estimated values. The loss of the RCNN was defined as the average of the two individual losses (cross-entropy and L2). The described loss function is an example, other loss functions can be used as for instance mean square error, L1 regularization, mean bias error, mean percentage error. Each mini-batch include of p amount of sequences of cubes (as a result from step 708). Typically p is around 36 sequences of cubes, but lower or higher number of p can be used. To avoid potential bias towards the most common type of plaque and stenosis in the augmented data, a stratified random data sampling was performed during the training as an optional step. This optional step ensures that each training iteration includes two distinct but balanced mini-batches. One mini-batch contained sections balanced with respect to their plaque classes regardless of the stenosis significance. A second mini-batch containing sections balanced with respect to the stenosis classes regardless of the plaque type. In case the MPR image is constructed as a curved MPR instead of a straight MPR, as described by step 203 of FIG. 2, the RCNN network will also take the curvature or tortuosity of the extracted centerline into account.

Figure 12:
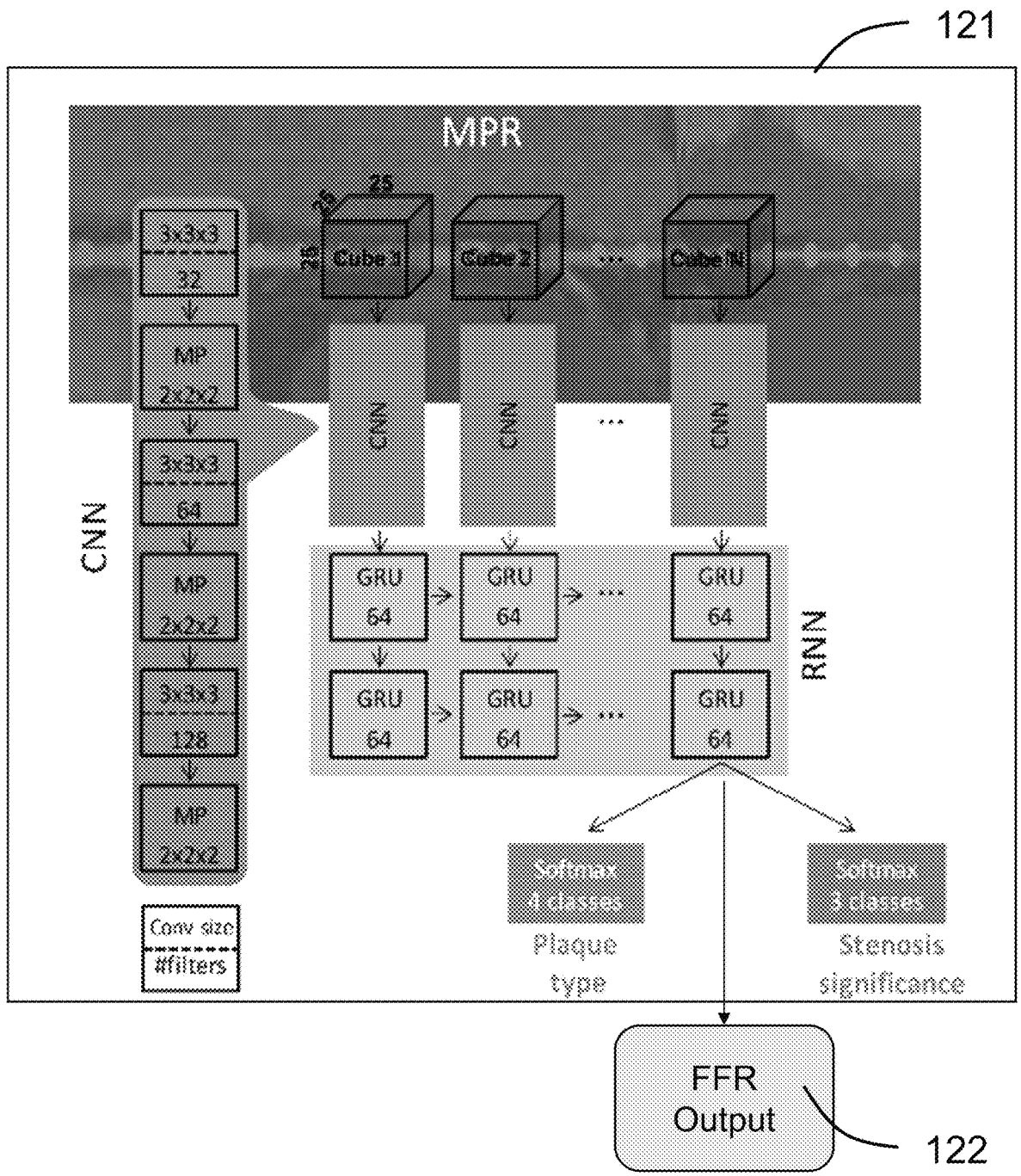
FIG. 12 shows an example of a RCNN architecture to detect coronary plaque type, anatomical lesion severity and functionally significant FFR along a coronary artery of interest.

The network architecture described by FIG. 11 is focused on detection of plaque type and anatomical stenosis severity. This network could also be restricted to one output, for instance only plaque type detection or only anatomical stenosis severity classification or to multiple outputs (>2), for instance but not limited to, plaque type classification, stenosis anatomical severity classification and functionally coronary lesion severity classification or FFR value prediction. An example of a network architecture, which is able to classify plaque type, classify anatomical stenosis severity and detect functionally coronary lesion severity/predict FFR values is illustrated by FIG. 12. Within this network architecture, the same RCNN is employed as described by FIG. 11 and illustrated by 121 within FIG. 12, with the addition of one output component 'FFR Output' (122) after the last GRU within 121. This block (122) represents the output to facilitate estimation/classification of FFR. For estimation, of FFR values, regression could be used to estimate continuous FFR values between 0 and 1, this output could be, but not limited to, the output of a linear activation function or a sigmoid activation. For classification (discreet class assignment of FFR severity or ranges, for instance FFR<0.7, 0.7<FFR<0.9, FFR>0.9), this output could be, but not limited to, the output of a multi-sigmoid function (with the same as number of classes) or a softmax function (with the same number of classes).

As FFR is defined as the pressure of a distal position within a coronary artery divided by the pressure at the proximal part of that coronary artery, the FFR pullback will only decrease along the length of the coronary artery, as visualized by image 504 of FIG. 5*a*. This knowledge can be taken into consideration within the loss function to train the classifier as described previously. To incorporate this decreasing behavior of decreasing FFR along the length of the coronary artery, the loss function is adapted to allow only decreasing of FFR from proximal to distal. This can for example be achieved by looking at previous, more proximal FFR prediction, and incorporate this information into the loss function.

Within an alternative embodiment, information within the myocardium is taken into consideration during assessment of the hemodynamic functional severity of a diseased coronary artery. As functionally significant coronary artery stenosis causes ischemia in the myocardium (FIG. 13), which impacts the texture characteristics of the myocardium wall within a CCTA dataset, such information will enhance the assessment prediction of functionally significant coronary artery stenosis, and the prediction of the FFR along the coronary artery of interest. By way of example, embodiments may implement the method as described by Isgum et al. in U.S. Ser. No. 10/765,575B2 (Method and system for assessing vessel obstruction based on machine learning) is integrated within the RCNN network architecture and illustrated by FIG. 14. Isgum et al described a method to detect the presence of functional significant stenosis in one or more coronary arteries based on machine learning using features of the myocardium, which can cope with the status of the myocardial microvasculature and collateral flow, without relying on the detailed morphology of the coronary arterial system. The network as shown in FIG. 14 combines the RCNN from FIG. 11 with the feature vector as described by Isgum et al. in U.S. Ser. No. 10/765,575B2 into one new network architecture. Within FIG. 14, 1401 represents the RCNN as described by FIG. 11, in which the two classifiers (1108) are removed. The feature vector from the RCNN (1401) and the feature vector as obtained from the myocardium analysis (1403) as described by U.S. Ser. No. 10/765,575B2 are concatenated by block 1404. Input for the myocardium feature vector (1403) is a CCTA image dataset (1402), which is the same CCTA image dataset in which the MPR image is created as used in the RCNN of 1401. The concatenation steps is performed by appending one feature vector (1401) to the other feature vector (1403). The results of the concatenation step are fed into a classifier (1405) which results into a prediction of the FFR output. This classifier can be a neural network, or a support vector machine or any other supervised machine learning classifier.

Figure 13:
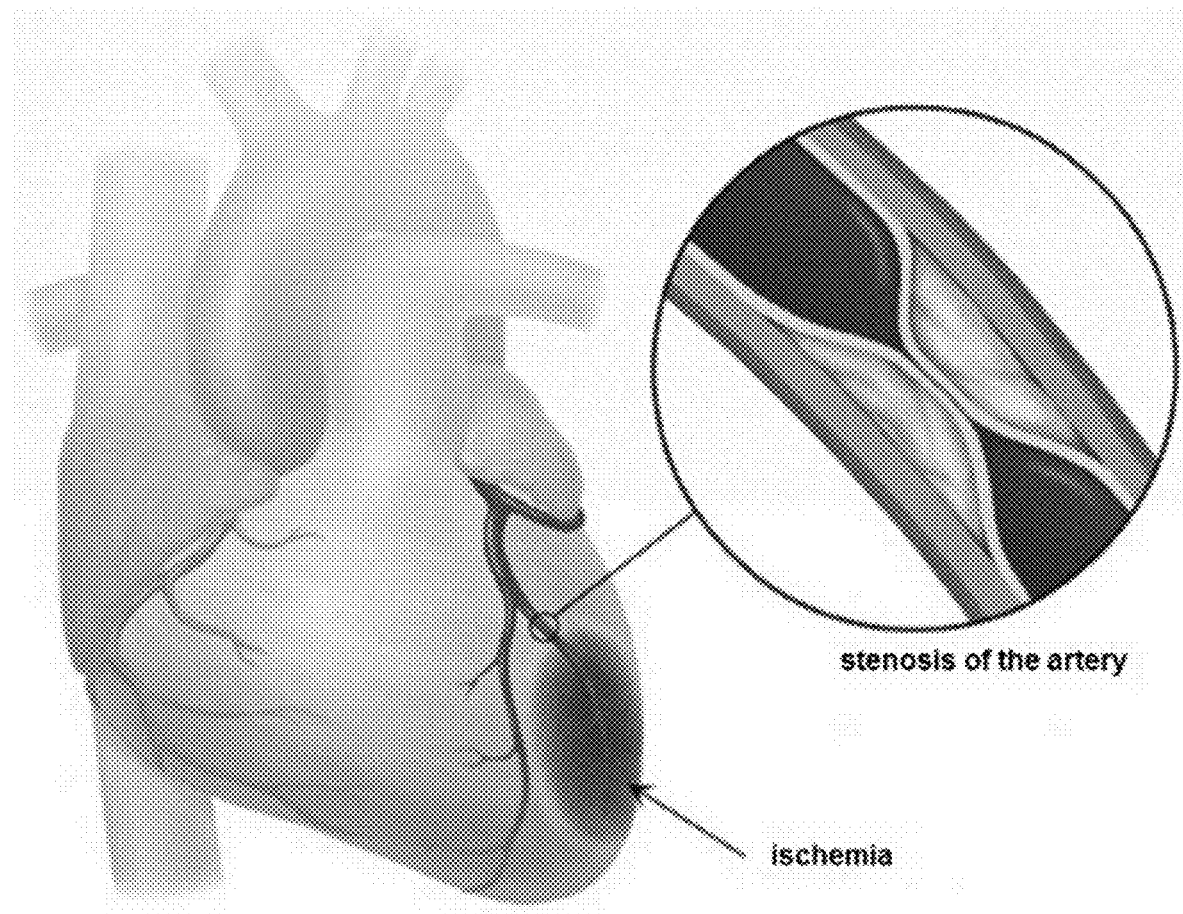
FIG. 13 shows an example of ischemia due to a stenosis of an artery.
Figure 14:
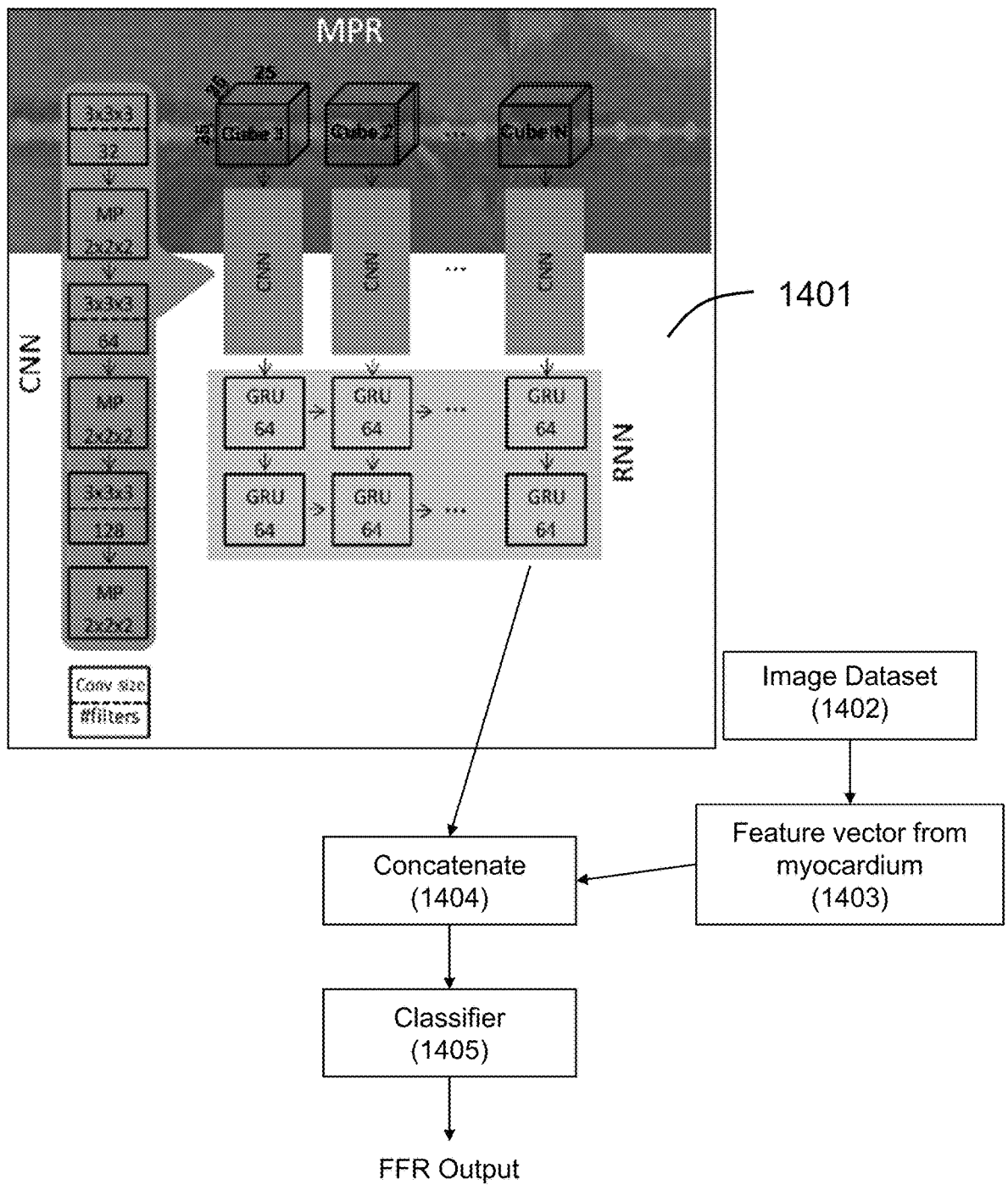
FIG. 14 shows an example of a RCNN architecture combined with a myocardium feature vector to assess functionally significant FFR within a coronary artery.

Functionally significant coronary artery stenosis causes ischemia in the ventricular myocardium distal to the functionally significant coronary stenosis, as illustrated by FIG. 13. This ischemia is caused by impedes oxygen delivery to the heart muscle (myocardium) distal to the lesion, or in other words the blood supply to this myocardium region is reduced and may cause symptoms to the patient such as angina. CCTA is acquired by applying intravenous injection in an antecubital vein, and the contrast medium injection is timed in such a way that the coronary arterial system contains sufficient contrast medium to clearly distinguish the coronary artery lumen from surrounding soft tissues. This means that the injected contrast medium, once it is present in the coronary arteries, will also be delivered to successively smaller generations of coronary arterioles from where it traverses into the coronary microvasculature (myocardium), which will lead to subtle enhancement of the myocardium, or reduced enhancement of the myocardium in case of ischemia. To exploit this CCTA acquisition effect in the prediction of FFR, within an alternative embodiment the generation of sequence of cubes as described by step 707 of FIG. 7 is adjusted to incorporate myocardium information distal to the cube of interest. This is further described with reference to FIG. 15.

Figure 15:
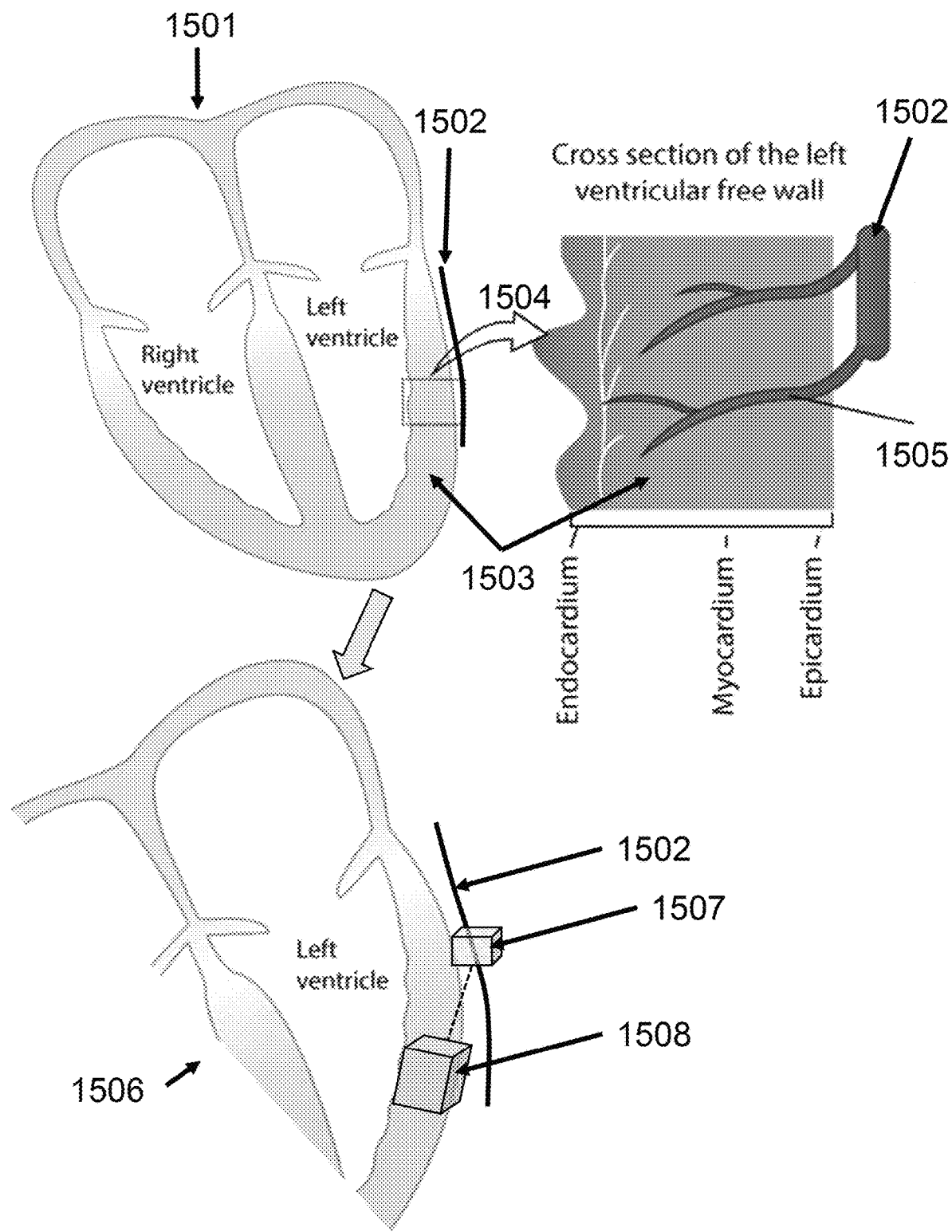
FIG. 15 shows an alternative approach used to create a sequence of cubes which includes myocardium distal to a location of interest.

FIG. 15 includes an image 1501 that shows a schematic view of the heart in a four chamber orientation. A short part of the coronary artery (1502) is identified and the myocardium is visualized by (1503). A small part of the myocardium is enlarged (1504), showing the location of the coronary artery (1502) and the microvasculature, which provide blood towards the myocardium, bifurcating from the coronary artery is visualized (1505) within the enlarged illustration of a small part of the myocardium. As described by step 707 of FIG. 7, the sequence of cubes is extracted from the MPR image around a centerline point of the extracted coronary centerline (result from step 704). Image 1506 illustrated the different resampling scheme. Now for each cube as extracted according to step 707, an additional cube, or cuboid, (1508) is resampled as well within the myocardium at a distance k distal to the centerline point of interest. The size and position of the cubes is managed to avoid including, in the cube 1508, any foxholes within the left or right ventricle. This can be achieved by sectioning of the blood pool, for instance by applying thresholding techniques or other image processing methods or even manually. Or alternative, by segmenting the myocardium. This can be done manually by the user or by (semi)automatic segmentation. One example of an automatic segmentation of the LV myocardium is given by Zreik et al "Automatic segmentation of the left ventricle in cardiac CT angiography using convolution neural networks", 2016 IEEE 13th International Symposium on Biomedical Imaging (ISBI), 2016, pp 40-43. Zreik et al, discloses a method in which the myocardium is automatically segmented using a convolutional neural network (CNN) trained on manually annotated data.

The size of the cube (1508) or cuboid is selected to cover the myocardium, the cube may overlap towards the epicardium into the epicardial fat tissue. The results of this alternative embodiment as illustrated by FIG. 15, is that each cube has a link to another corresponding cube/cuboid which is located distal to the location of interest. This addition cube/cuboid is fed into the CNN, or alternatively new CNN's for the additional cubes/cuboids are used, as shown by the RCNN network by FIG. 12 or FIG. 14.

Figure 16:
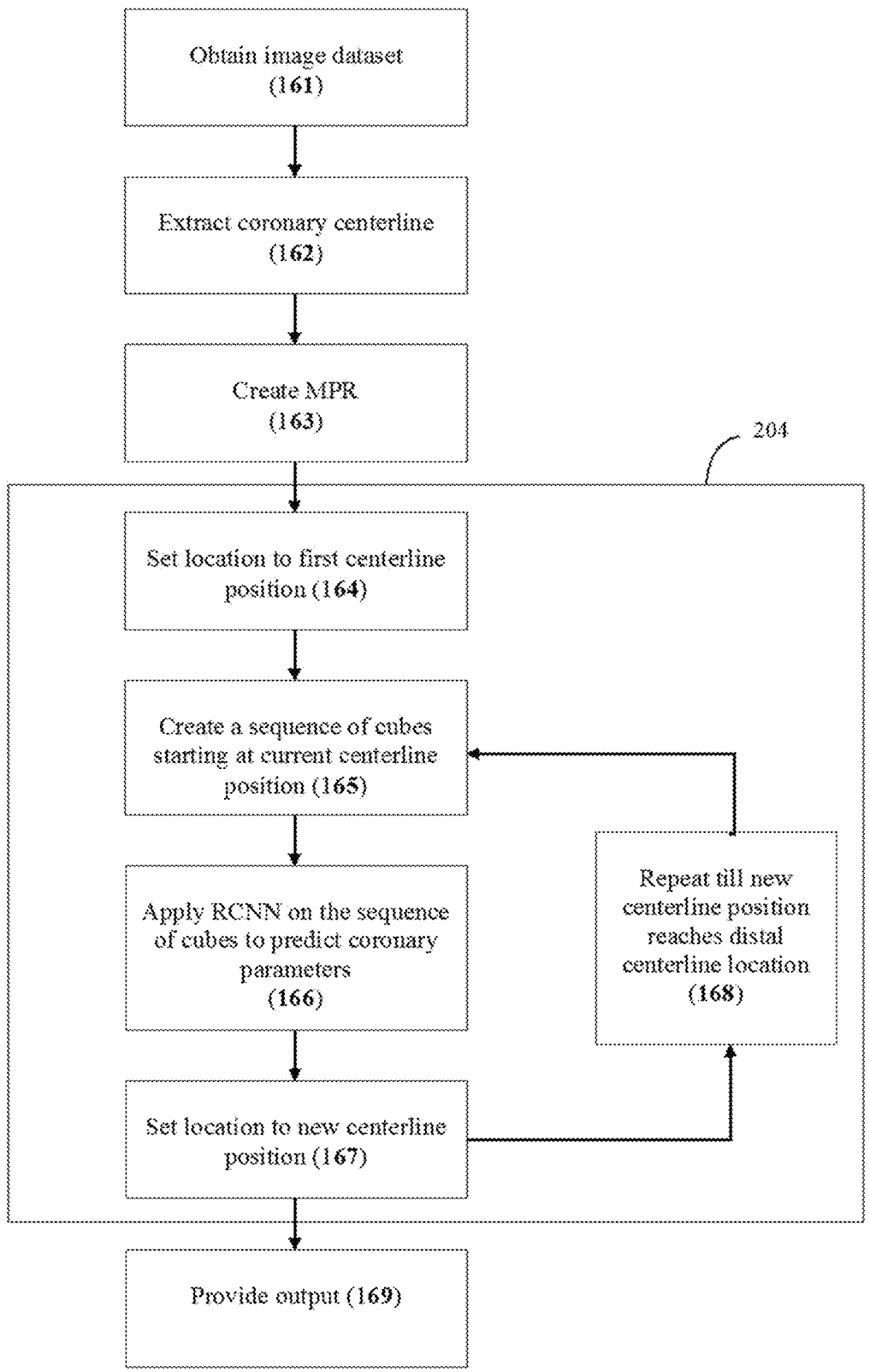
FIG. 16 shows a flowchart of an embodiment of the present application for the prediction phase.

Once the RCNN network is trained (FIG. 11, FIG. 12, or FIG. 14), new unseen CCTA datasets are classified into the classes as defined during the training phase, which is further explained by the flowchart of FIG. 16.

FIG. 16 illustrates a method for implementing a prediction phase, to detect plaque type, classify anatomical severity of vessel obstruction(s) and/or classify the severity of vessel obstruction(s) within unseen CCTA datasets. The unseen CCTA dataset is represented by step 161 of FIG. 16.

Step 162 of FIG. 16 the coronary centerline is extracted which represent the center of the coronary lumen along the coronary section of interest. This step is identical of step 202 of FIG. 2.

Within step 163 of FIG. 16, a multi-planer reformatted (MPR) image is created along the extracted coronary section from step 162. Step 163 of FIG. 16 is identical to step 203 of FIG. 2.

Step 164 up to and including step 168 of FIG. 16 represents block 204 of FIG. 2 during the prediction phase; classify coronary parameters such as plaque type, anatomical coronary lesion severity and/or functionally coronary lesion severity and/or FFR values of unseen CCTA image dataset. Prediction of the coronary parameters is performed on each centerline point within the MPR image. Step 164 of FIG. 16 set the start position to the first centerline point in the MPR image; the first position with respect to the x-axis of the MPR image (the length of the MPR image).

Within step 165 of FIG. 16 a sequence of cubes is constructed around the centerline position under examination. The sequence of cubes is created in a similar matter as described by step 707 of FIG. 7 and illustrated by FIGS. 9a-9c. In step 165, a single sequence of cubes is created around the centerline position under examination. The size of the cube is identical to the size as used during the training (step 707 of FIG. 7) but other sizes can be used. The length of the sequence is fixed to 1 cubes, and 1 is for instance 5 cubes. The distance between the cubes is m voxels, m is typically 5. Larger cubes and/or longer sequences and/or different strides could be used. Special care is taken around the start and end of the MPR image, to force valid cube (cubes may partially be outside the MPR image). To make sure that the cube contains valid MPR image data, during resampling for example, the nearest valid voxel within the MPR image can be identified in case a position within the cube is outside the MPR image.

Step 166 of FIG. 16 predicts the desired coronary parameter at a current centerline position within the MPR image based on the sequence of cubes as a result from step 165. Within this step the same RCNN network architecture is selected as used during the training phase as described by the flowchart in FIG. 7. For instance, FIG. 11 provides an example of a RCNN network architecture for prediction of coronary plaque type and anatomical coronary lesion severity. This RCNN is trained using annotated plaque type and annotated anatomical lesion severity (reference value). To predict the coronary plaque type and anatomical coronary lesion severity on unseen image data, step 166 uses the same RCNN network architecture and the trained model of this RCNN architecture is used. FIG. 12 provides a RCNN network architecture to assess plaque type, anatomical lesion severity and the functionally coronary severity and is trained on the annotated plaque type, annotated anatomical lesion severity and the pullback data obtained from invasive FFR measurements. During prediction, the same RCNN architecture is used as illustrated by FIG. 12 and the trained model of this RCNN architecture is selected. The same is true for the RCNN architecture provided by FIG. 14, in which only the functionally lesion severity is trained and predicted by the current step.

Step 167 of FIG. 16 sets the centerline position under examination to a new location. This can be the next centerline position within the extracted coronary centerline tree (i.e. next location within the MPR image along the length of the MPR image), or a centerline position with a predefined distance with respect to current centerline location.

Step 165, 166 and 167 are repeated as illustrated by block 168 until the last centerline position within the extracted coronary centerline is reached.

Finally step 169 provides several methods to present the results and is identical to step 206 of FIG. 2.

Figure 17:
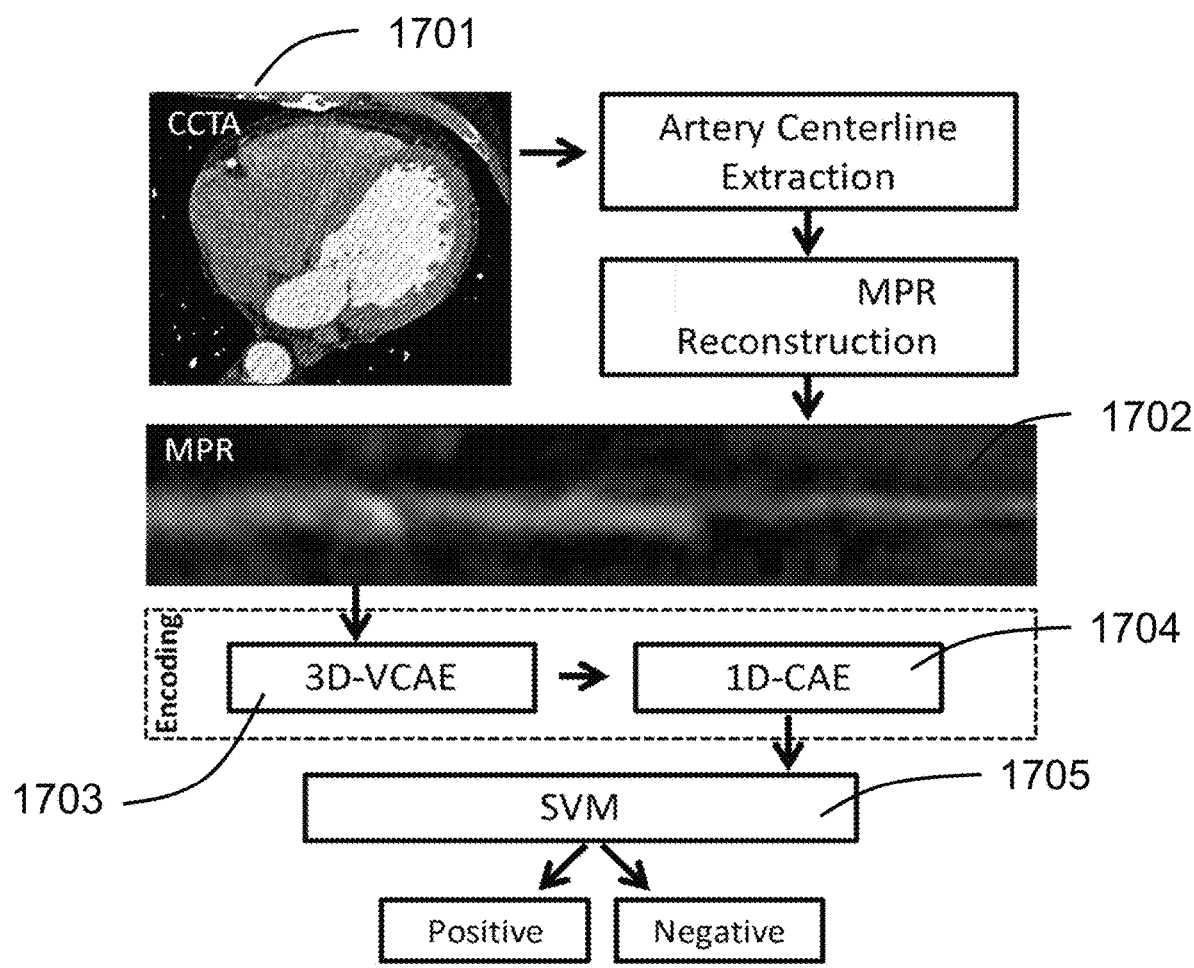
FIG. 17 shows an alternative workflow to assess the hemodynamic functional severity of a coronary artery.

Within an alternative embodiment, the machine learning algorithm deployed to assess the hemodynamic functional severity of a coronary artery within block 204 of FIG. 2 uses a different network architecture, and results in a slightly different flowchart for both the learning phase as well for the prediction phase. FIG. 17 illustrates the overall workflow.

Within a CCTA scan (1701), the centerlines of the coronary arteries are extracted and used to reconstruct multi-planar reformatted images of the coronary arteries (1702). Then, an unsupervised dimensionality reduction step is applied, where the MPR image (volume) of a complete artery is compressed into a fixed number of features (encodings) using two unsupervised autoencoders, applied sequentially: first) a 3D variational convolutional autoencoder 1703 (3D-VCAE), that spatially compresses local sub-volumes (cubes) of the coronary artery, and second) a 1D convolutional autoencoder 1704 (1D-CAE), that sequentially compresses the encodings of the complete coronary artery obtained previously by the 3D-VCAE. Then the final extracted encodings are employed in a supervised fashion with a support vector machine (SVM) classifier or any other supervised classifier 1705, to classify arteries (and patients) according to FFR.

Figure 18:
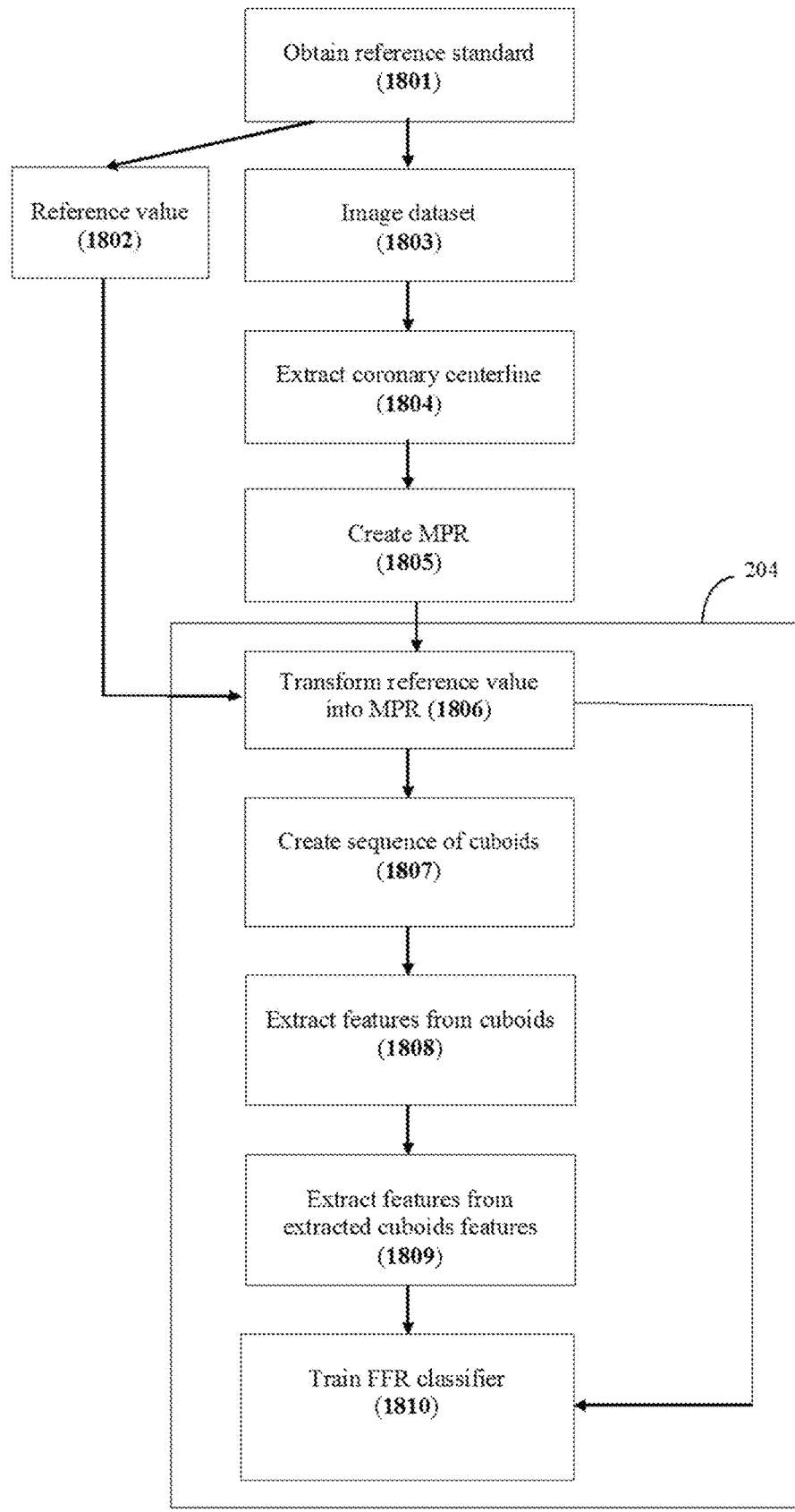
FIG. 18 shows an alternative flowchart of the generation of an FFR classification model as performed by the training phase.

FIG. 18 shows the detailed flowchart to be employed during the training phase to train the vessel obstruction assessment model. In step 1801 of FIG. 18 the reference standard database is obtained and used to train the machine learning network. The reference standard database is a database which contains data of multiple patients. For example, the database contains, for each patent, a) contrast enhanced imaging (e.g. CT) datasets (step 1803) and corresponding b) invasively measured fractional flow reserve reference values (step 1802). The fractional flow reserve reference values correspond to pressure measurements that are invasively measured during a pressure wire pullback operation or at a single point proximate the distal position of the coronary vessel of interest. Other hemodynamic indices can be used to assess functionally significant coronary artery obstruction(s) such as coronary flow reserve, instantaneous wave-free ratio, hyperemic myocardium perfusion, index of microcirculatory resistance and pressure drop along a coronary artery.

In step 1804 of FIG. 18, the processors extract the axial trajectory (e.g., coronary centerline) which represent the center of the vessel of interest (VOI) lumen along the VOI section of interest. This step is substantially similar to step 202 of FIG. 2.

In step 1805 of FIG. 18, the processors create the MPR image along the extracted coronary centerline as a result from step 1804. Step 1805 of FIG. 18 is identical to step 203 of FIG. 2.

In step 1806 of FIG. 18, the processors align the FFR reference value 1802 to the spatial coordinates of the MPR image as a result of step 1805. This step is substantially similar to step 706 of FIG. 7. In case the FFR reference values are obtained by using the MPR image as a results from step 1805, this step is skipped. This step is also skipped in case the FFR reference value consist a single point value.

Figure 19A:
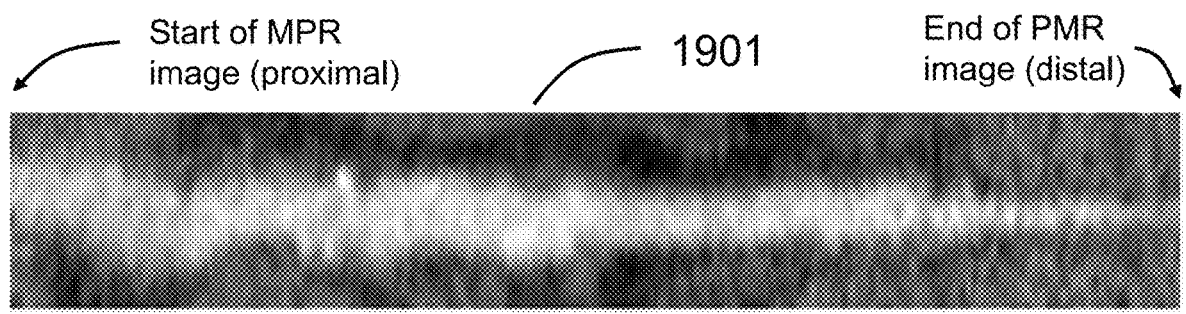
FIGS. 19a-19c show a visual illustration of the encoder/decoder output of a CAE illustrated by using an MPR image.
Figure 19B:
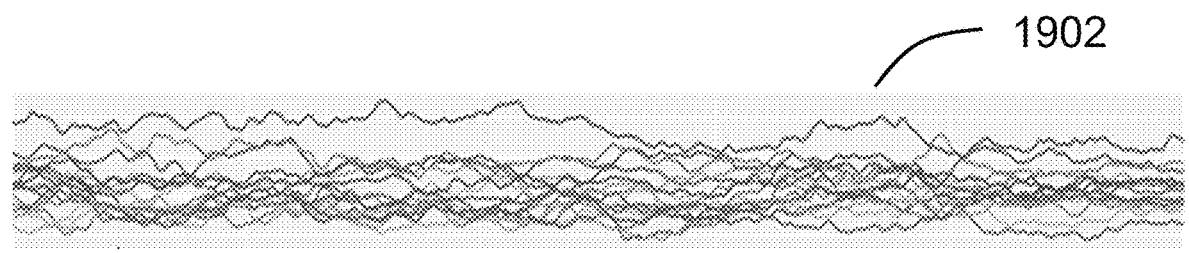
Figure 19C:
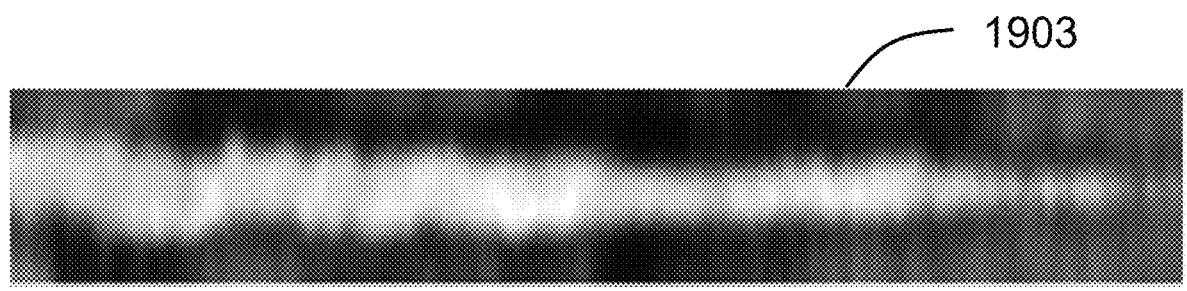

In step 1807 of FIG. 18, the processors generate the sequence of cuboids from the MPR image which are used to train the machine learning based vessel obstruction assessment model as described further within the remaining step of current workflow. The generation of the sequence of cuboids is illustrated by FIGS. 19a-19c. Along the MPR image (1901 of FIG. 19a) a sequence of cuboids (image 1902 of FIG. 19b) is created which resamples the MPR image into smaller volumes. The size of the cuboid is defined that it contains the whole arterial lumen and a part within the vicinity of the artery. Each cuboid is typically 40×40×5 voxels, but other cuboid sizes are possible. The distance between the cuboids is m centerline points (m is typically 1 voxel, but other distances between the cuboids can be possible). In case that the distance between the centerline points is one voxel, the length of the sequence of cuboids is identical to the length of the extracted centerline and to the length of the MPR image.

In step 1808 of FIG. 18, the processors extract features from the cuboids. In step 1809 of FIG. 18 the processors extract features from the extracted cuboid features. For example, the features characterizing the pressure drop within a VOI (e.g. coronary artery of interest) are extracted from the MPR image by analyzing the sequence of cuboids as a result from step 1807. As blood flow and pressure in a coronary artery may be affected by several coronary artery stenoses located along the artery at hand. Different combinations of stenoses locations and grades, i.e. degrees of lumen narrowing, may cause a drop in FFR along the artery. Therefore, to detect drops in FFR within an artery, local analysis around the stenoses may be insufficient, and instead volumetric analysis of the complete artery should be performed. Coronary arteries are complex anatomical 3D structures, with varying lengths and anomalies across patients. The resolution of modern CT scanners is high and a large number of voxels (millions) is contained in a volumetric image data set for a single artery and following the straightforward approach of training a single convolutional autoencoder (CAE), applied directly to the complete (or a substantial majority of) artery volume without a large reconstruction error, is unlikely. To address the foregoing concerns, the CAE network architecture used in accordance with embodiments herein includes a two-stage encoding approach to encode a complete MPR image (volume) of the coronary artery, regardless of its length and anatomy.

A CAE compresses the data from an input image to a small vector that contains enough information to reconstruct the input image by the decoder. By this the autoencoder is forced to learn features about the image being compressed. This is illustrated by FIGS. 19a-19c. Image 1901 of FIG. 19a shows an example of the extracted MPR image as a result from step 203 of FIG. 2 and further illustrated by FIGS. 4a-4e. The proximal part which is at the start of the centerline which identifies the coronary of interest is at the left side of image 1901 and the end of centerline is at the right side of the MPR image. Image 1902 of FIG. 19b illustrates several features (information) along the length of the MPR image extracted by the encoder of a CAE. Image 1903 of FIG. 19c shows the results of the decoder, reconstructing the original image. A typical CAE includes two major parts, an encoder and a decoder. The encoder compresses (encodes) the data to lower dimensional latent space by convolutional operations and down-sampling (max-pooling), and subsequently expands (decodes) the compressed form to reconstruct the input data by deconvolutional operations and upsampling (unpooling). Training the CAE, while minimizing a distance loss between the encoder input and the decoder output, ensures that the abstract encodings, generated from the input, contain sufficient information to reconstruct it with low error. Once the CAE is trained, the decoder is removed, and the encoder is used to generate encodings for unseen data.

Figure 20:
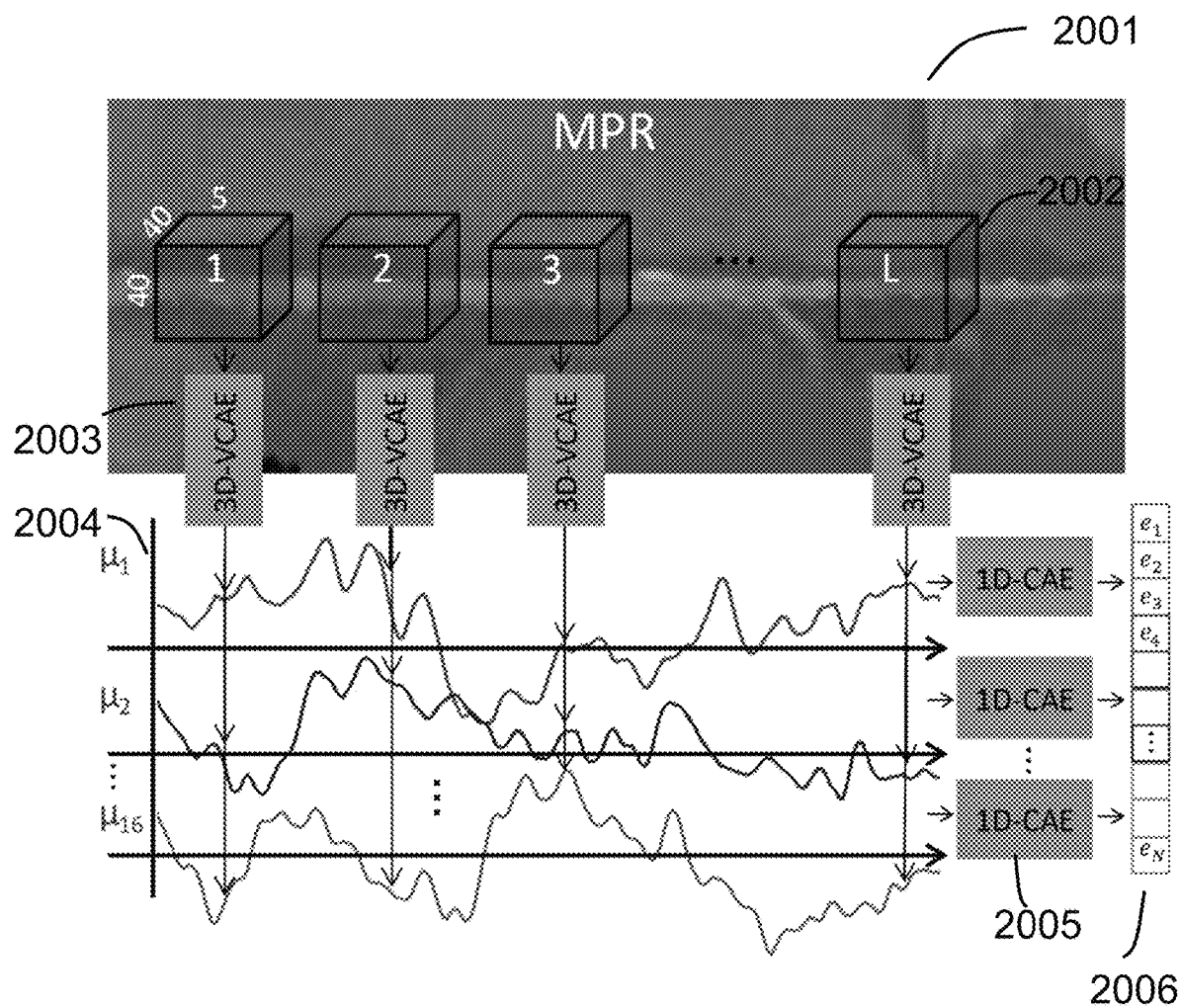
FIG. 20 shows an example of the architecture of a 3D variational convolutional autoencoder combined with a 1D auto encoder as used during learning FFR classification model, as used during the prediction phase.

FIG. 20 illustrates the encoding flow. First, represented by step 1808, a 3D variational convolutional autoencoder (3D-VCAE) is applied (2003) on local sub-volume (cuboid 2002) extracted from the MPR image 2001 along the artery centerline (as in FIG. 18, 1807). The 3D-VCAE encodes each sub-volume into a set of encodings. When applied to all sequential sub-volumes (within a step size of 1) along the extracted coronary centerline (1804 of FIG. 18), the result is a 2D features map of the same length as the artery. This 2D features map is then represented as a set of 1D sequences of encodings, running along the artery (2004). In a preferred embodiment, the features characterizing the pressure drop within a coronary artery of interest are characterized by the features in an unsupervised manner, extracted by a 3D-VCAE applied on the local sub-volumes (cuboids). Alternative, any other engineered characteristic that describes the pressure drop along a coronary artery by the sequence of cuboids can be employed (e.g. Gaussian filters, Haralick texture features) and/or morphology (e.g. coronary lumen, coronary volume, lumen intensity) can be used as features. An example of such alternative engineered feature method designed to quantify the perceived texture within the cuboids is by computing Haralick texture features, which captures numerical features of a texture using spatial relations of similar gray tones (Robert M. Haralick et al., "Textural Features for Image Classification", IEEE Transactions on Systems, Man, and Cybernetics, 1973, SMC-3 (6): 610-621). Any combination of these features can be selected.

Finally, represented by step 1809 of FIG. 18, the processors apply a 1D convolutional autoencoder (1D-CAE) to each sequence of encodings separately (2005 of FIG. 20). Hence, the 1D-CAE encodes the varying length sequences of encodings further into a fixed number of encodings that represent the complete artery, regardless of its length.

3D-VCAE

Figures 21A, 21B:
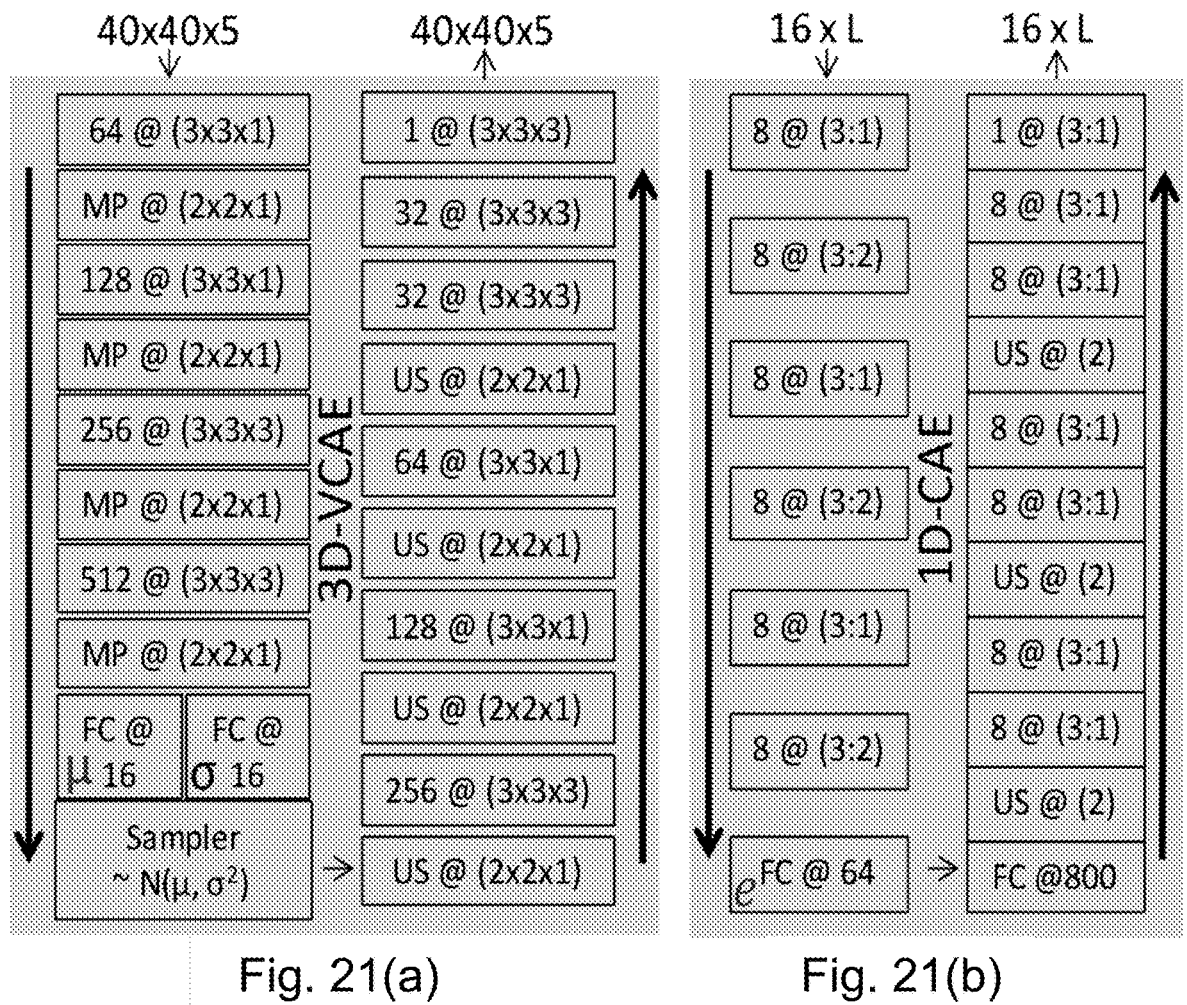
FIG. 21a shows an example of the detailed network architecture of the 3D-VCAE.
FIG. 21b shows an example of the detailed network architecture of the 1D-CAE.

Variational autoencoder (VAE) are generative models, which approximate data generating distributions as described by Kingma et al, "Auto-encoding variational bayes", arXiv preprint arXiv:1312.6114, 2013. Through approximation and compression, the resulting models capture the underlying data manifold; a constrained, smooth, continuous, lower dimensional latent (feature) space where data is distributed (Kingma et al, "Semi-supervised learning with deep generative models", Advances in neural information processing systems, 2014, pp. 3581-3589). These advantageous properties of the latent space is used within current embodiment to employ a VCAE to compress and encode local volumes along the artery. To capture local volumetric characteristics of the artery, the input to the 3D-VCAE is set to a volume as described by step 1807. The output of the encoder in the 3D-VCAE is set to a predefined number of encodings (2004), for instance 16. To encode the complete artery, overlapping volumes with stride of 1 voxel are extracted and encoded with 3D-VCAE. This results, in case of 16 numbers of encodings per centerline points, in 16×L encodings, where L is the length of the extracted coronary centerline. The detailed 3D-VCAE architecture is shown in FIG. 21a. FIG. 21a shows the detailed network architecture of the 3D-VCAE. The input and outputs are volumes of for instance 40×40×5 voxels. Within FIG. 20a, the key: N @ (sizekernel) is a convolutional layer with N kernels of size sizekernel. MP @ (sizekernel) is a max-pooling layer with kernel size sizekernel. US @ (sizekernel) is an upsampling layer with kernel size sizekernel. FC @ (Nunits) is a fully connected layer with Nunits units. Once the 3D-VCAE is trained, the output of the µ layer is used to generate encodings for the input. Descending and ascending arrows represent the encoder and the decoder in each autoencoder, respectively. In the 3D-VCAE, batch normalization layers and rectified linear units (ReLUs) are used after all convolution layers except the encoder and decoder output layers. Other parameters can be used, for instance different kernel sizes, number of encoding layers as well as other CAE architectures and activation functions. Furthermore, the input size of the CAE can be different as well of the use of a 4D voxel patch for instance to support multiphase CCTA datasets. The input patch can be even a higher dimensional voxel patch, for instance n-dimensional to support multi-energy and/or multiphase CCTA dataset.

1D-CAE

When representing the coronary artery to predict FFR, characteristics along the artery, starting from the ostium to the most distal part of the extracted coronary centerline, are taken into account. Therefore, the local encodings from the 3D-VCAE are further compressed by the 1D-CAE 2005 while analyzing the complete artery at once. To accomplish this, the 2D features map, includes a set of the for example 16 encodings generated by 3D-VCAE at each coronary artery center point, is represented as a set of 1D sequences 2004. Each sequence includes 1×L encodings, where L represents the length of the artery, i.e. number of coronary artery center points. This representation leads each sequence to represent a specific encoding along the artery (2004), and consequently, allows to apply a simple 1D-CAE to each of the 16 sequences of encodings separately (2005). The weights of the 16 1D-CAEs are shared, where each 1D-CAE encodes one of the 16 sequences into for example 64 encodings. This results in n features (2006) that represent the complete coronary artery of interest. In our example n is 16×64, 1024 features. The detailed 1D-CAE architecture is shown in FIG. 21b. The input and outputs are for instance 16×L sequences of encodings. Within FIG. 21b, the key: N @ (sizekernel:sizestride) is a 1D convolutional layer with N kernels of size sizekernel and stride of sizestride. US @ (sizekernel) is a 1D upsampling layer with kernel size sizekernel. The 1D-CAE is applied separately, but with shared weights, on each one of the 16 1D-sequences. Once the 1D-CAE is trained, the output of the e layer (FIG. 21b) is used to generate encodings for each input sequence. Descending and ascending arrows represent the encoder and the decoder in each autoencoder, respectively. In the 1D-CAE, the exponential linear units (ELUs) are used after all convolutions layers except the encoder and decoder output layers. Other parameters can be used, for instance different kernel sizes, number of encoding layers as well as other CAE architectures and activation functions.

Figure 22:
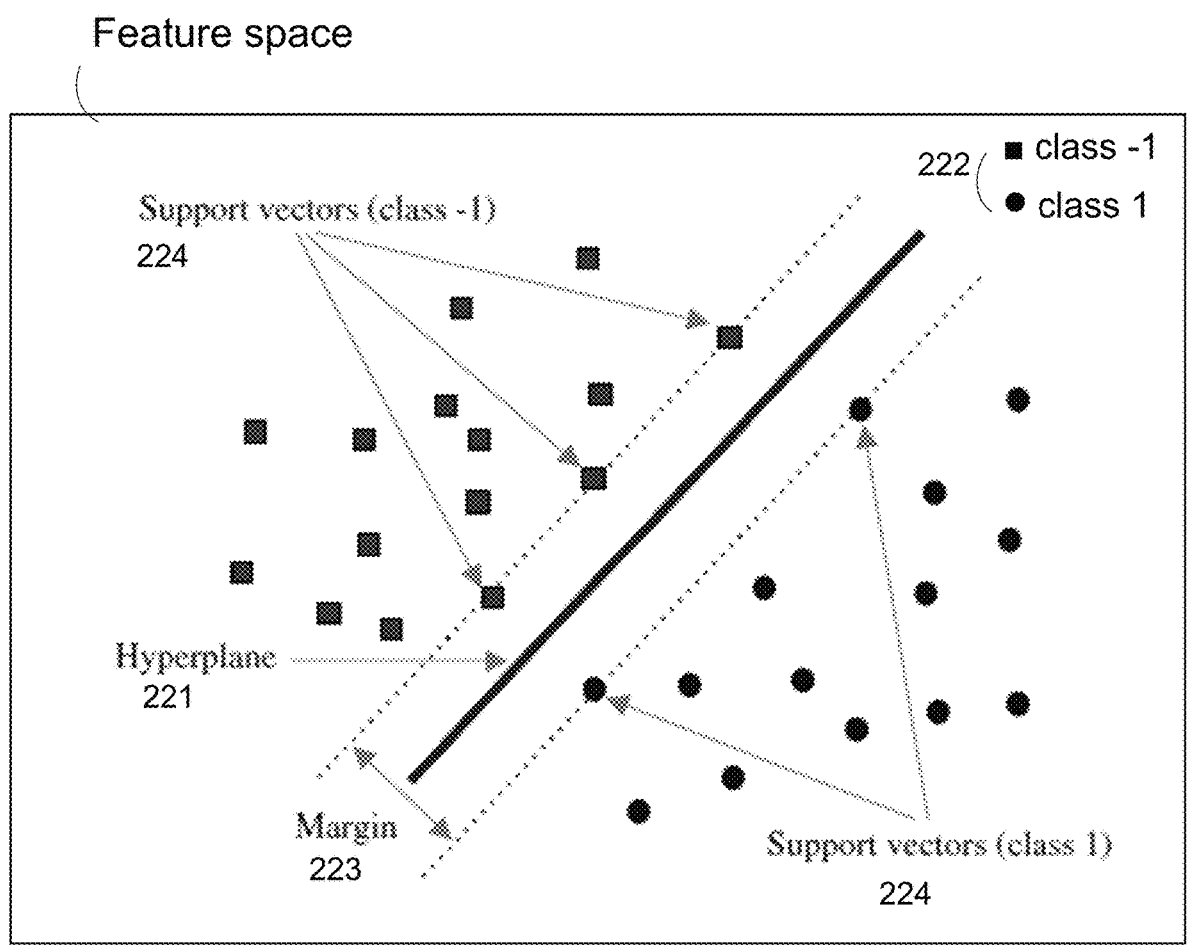
FIG. 22 shows an example of a feature space wherein the training data is represented as points, mapped so that the data of the separate categories are divided by a clear gap that is as wide as possible.

Within step 1810 of FIG. 18, the processors apply a supervised classifier to train an FFR classifier. Several supervised classifiers could be used, for instance, a support vector machine (SVM) classifier. An SVM is a supervised machine learning classifier that can be employed for both classification and regression purposes. SVMs are based on the idea of finding a hyperplane (221, FIG. 22) that best divides a dataset into predefined classes (222, FIG. 22). As a simple example, for a classification task with only two features is illustrated in FIG. 22. During training of the SVM, a hyperplane that best separates samples of two classes is found by maximizing the margin around the decision boundary while minimizing the number of training samples within the margin (FIG. 22). The margin (223, FIG. 22) is determined by the support vectors (224, FIG. 22) i.e. training samples that lie on the margin. Intuitively, a good separation is achieved by the hyperplane that has the largest distance to the nearest training-data point of any class. In other words, the distance between the hyperplane and the nearest support vector from either set is known as the margin. The goal of SVM is to find a hyperplane with the greatest possible margin between the hyperplane and any point (support vector) within the training set. Other kinds of classifiers may include neural networks, Bayesian classifiers, Tree Ensembles (e.g., random Forests) (Kotsiantis et al, "Supervised Machine Learning: A Review of Classification Techniques", Informatica 31, 2007, 249-268). To be able to use a supervised (SVM) classifier, reference data must be present that can be used as a reference standard. The reference standard is a database from multiple patients (step 1801). Each set within this database contains a) contrast enhanced CT datasets (step 1803) with belonging b) reference value (step 1802). In a preferred embodiment, the reference value indicative for functional significance coronary lesion (e.g. FFR) 1802, representing a fluid-dynamic parameter, is an (pullback) invasive fractional flow reserve (FFR) measurement as performed during X-ray angiography which belongs to the contrast enhanced CT dataset 1803. For example, FFR is measured with a coronary pressure guidewire at maximal hyperemia induced by intravenous adenosine. During X-ray angiography the FFR wire is placed as distally as possible in the target vessel and FFR is assessed by means of a manual or automatic pullback in the distal part of the target vessel. Finally, the FFR wire is retrieved at the level of the guiding catheter to achieve an FFR value of 1.00 in order to assess the quality of the measurement performed. When multiple FFR measurements are available due to repeated measurements or multiple stenosis, the minimal value is taken as the standard of reference. The FFR reference value 1802 can be any parameter which links the patient specific CCTA datasets to myocardial ischemia of that patient. For instance, the reference value (1802) can be the measured coronary flow reserve or the index of microcirculatory resistance which provides a measurement of the minimum achievable microcirculatory resistance in a target coronary artery territory, enabling a quantitative assessment of the microvascular integrity. Other examples of different parameters for the reference value (1802) are the occurrence of major adverse cardiac events (MACE) within a predefined amount of time after acquisition of the CCTA dataset, or if the patient underwent revascularization within a predefined amount of time after acquisition of the CCTA dataset, or the results of cardiac stress test, the results of myocardial magnetic resonance imaging (MRI) perfusion, SPECT, PET, CT perfusion, or ultrasound.

Using a database of FFR reference values 1802, which corresponds to the used CCTA dataset 1803, each reference value (1802) is marked as belonging to one of two classes, for instance "functionally significant stenosis present" (invasive FFR<for instance 0.8) or "no significant stenosis present" (invasive FFR>for instance 0.8) (the known labels), the SVM classifier learns to separate the different classes. First, each training sample (e.g. CCTA dataset) is represented as a point in an n-dimensional feature space, where n is the number of computed features (e.g. the number of features in the feature vector, the result of step 1809 of FIG. 18). For all reaming CCTA cases in the database 1803, such a feature vector is computed. All training samples (e.g. CCTA cases in the database) are used to train the chosen classifier. In the training phase, the SVM classifier finds the hyperplane that makes the best separation between the classes i.e. by finding a hyperplane separating two classes with the largest margin as illustrated in FIG. 22.

SVM is in nature a two-class classifier. Nevertheless, multi-class classification, i.e. classification in multiple classes, can be performed by e.g. performing multiple 2-class classifications (e.g. chosen class vs. all remaining classes or between every pair of classes—one vs one). Hence, the FFR classifier (1810, FIG. 18) can be trained to recognize multiple classes, for example "no functionally significant stenosis present", "mild functionally significant stenosis present" or "severe functionally significant stenosis present", or any categories chosen based on the reference value (step 1802 of FIG. 18). When the reference value (FIG. 18, 1802) is an invasive FFR measurement, above classification can be achieved using for instance the following invasive FFR threshold values:

i) Invasive FFR>0.9—"no functionally significant stenosis present"

ii) Invasive FFR between 0.7 and 0.8—"mild functionally significant stenosis present"

iii) Invasive FFR<0.7—"severe functionally significant stenosis present"

Figure 23:
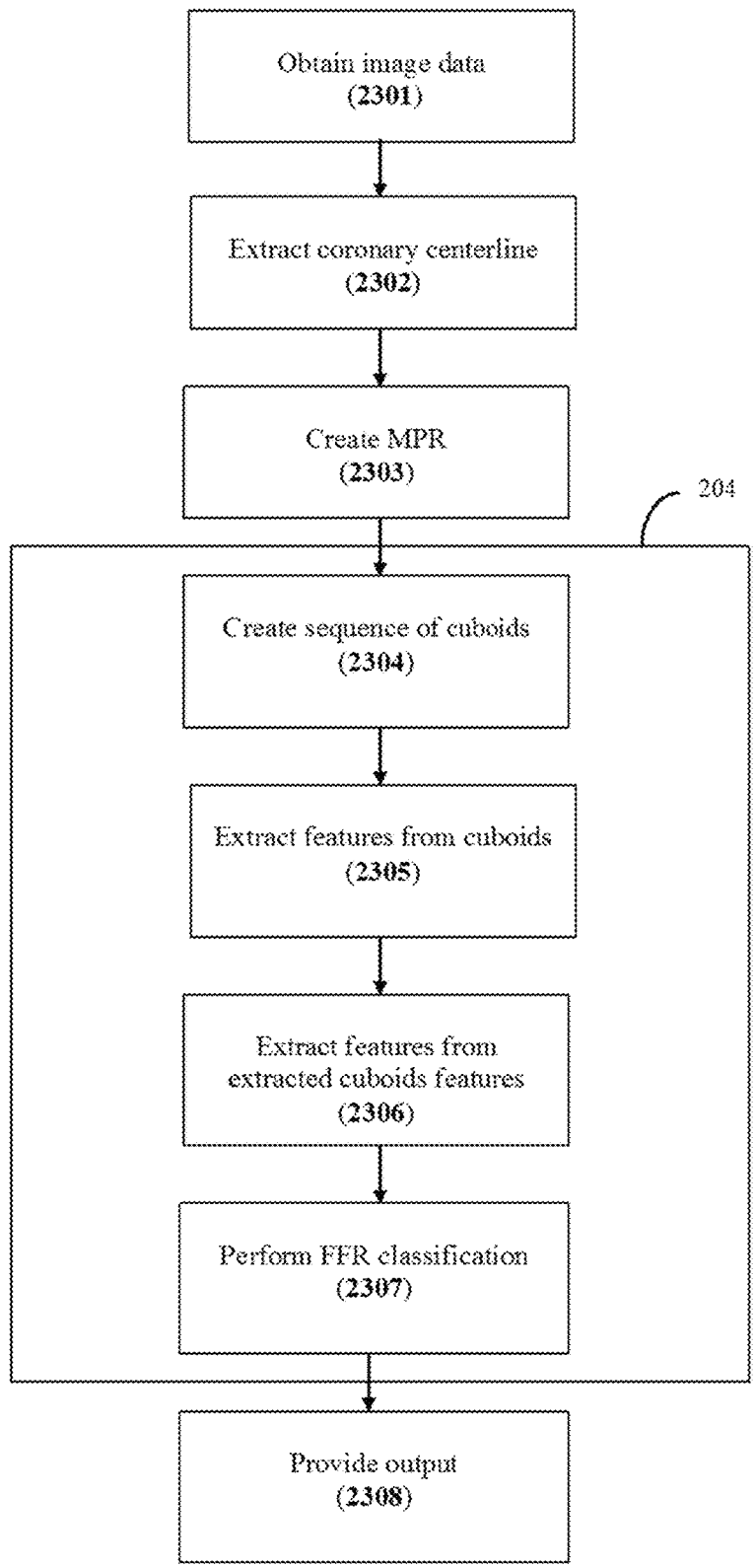
FIG. 23 shows an alternative flowchart of the prediction phase using the trained FFR classification model as performed by the training phase.

Once the system is trained, new unseen CCTA datasets are classified into the classes as defined during the training phase, which is further explained by the flowchart of FIG. 23. FIG. 23 illustrates a framework for implementing the prediction phase, to classify the severity of vessel obstruction(s), or detect the FFR value within unseen CCTA datasets; to determine the presents of functionally significant stenosis in one or more coronary arteries from a CCTA dataset. The unseen CCTA dataset is represented by step 2301 of FIG. 23.

Step 2302 of FIG. 23 the coronary centerline is extracted which represent the center of the coronary lumen along the coronary section of interest. This step is identical of step 202 of FIG. 2.

Step 2303 of FIG. 23 a multi-planer reformatted (MPR) image is created along the extracted coronary section from step 2302. Step 2303 of FIG. 23 is identical to step 203 of FIG. 2.

Step 2304 up to and including step 2307 of FIG. 23 represents block 204 of FIG. 2 during the prediction phase and classifies the functionally coronary lesion severity of unseen CCTA image dataset. Prediction of the functionally coronary lesion severity is performed on the complete coronary of interest represented within the MPR image. Within step 2304 of FIG. 23 the generation of the sequence of cuboids from the MPR image is performed and is identical to step 1607 of FIG. 16.

Within step 2305 and 2306 of FIG. 23 the computing of the features takes place and is identical as described previously for step 1808 and 1809 of FIG. 18.

Figure 24:
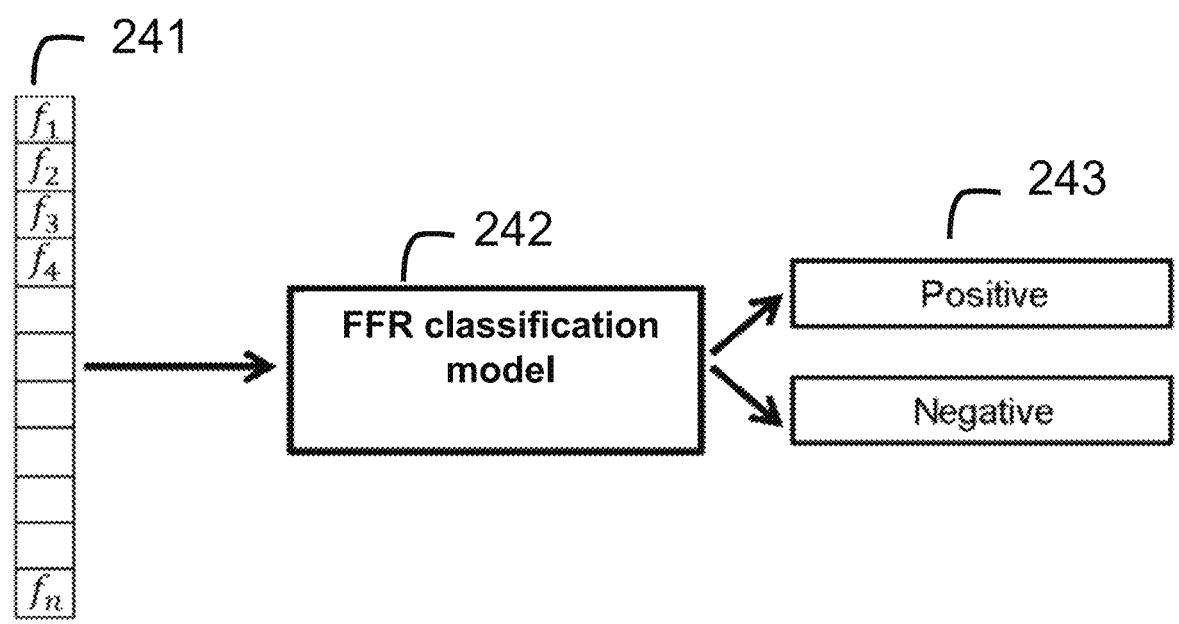
FIG. 24 shows an illustration of the classifier to classify unseen data. Within this visual representation, the input is the feature vector computed from the unseen image and the output two classes.

In step 2307 of FIG. 23, the FFR classifier assigns new unseen CCTA datasets into the categories as defined during the training phase. This classifier is the same classifier as used in block 1810 in FIG. 18. Within the prediction phase, unseen CCTA dataset are mapped by step 2307 of FIG. 23 in the n-dimensional feature space and its location in this feature space with respect to the hyperplane determines its class label. This classification results in an assessment of the severity that one or more coronary obstructions impedes oxygen delivery to the heart muscle and is represented by step 2308 of FIG. 23. FIG. 24 shows a visual representation of the classifier. The result of step 2306 of FIG. 23, representing the feature vector of the unseen image, is the input (241) of the classifier. Label 242 of FIG. 24 represents the FFR classification model, as learned during the learning phase as described by step 1810 of FIG. 18. Label 243 of FIG. 24 represent the output of the classifier (FIG. 23, 2308) incase two classes are learned; positive meaning one or more functionally significant coronary lesions present, and negative meaning no functionally significant coronary lesion present.

Finally step 2308 provides the output and present the results and is identical to step 206 of FIG. 2.

Figure 25:
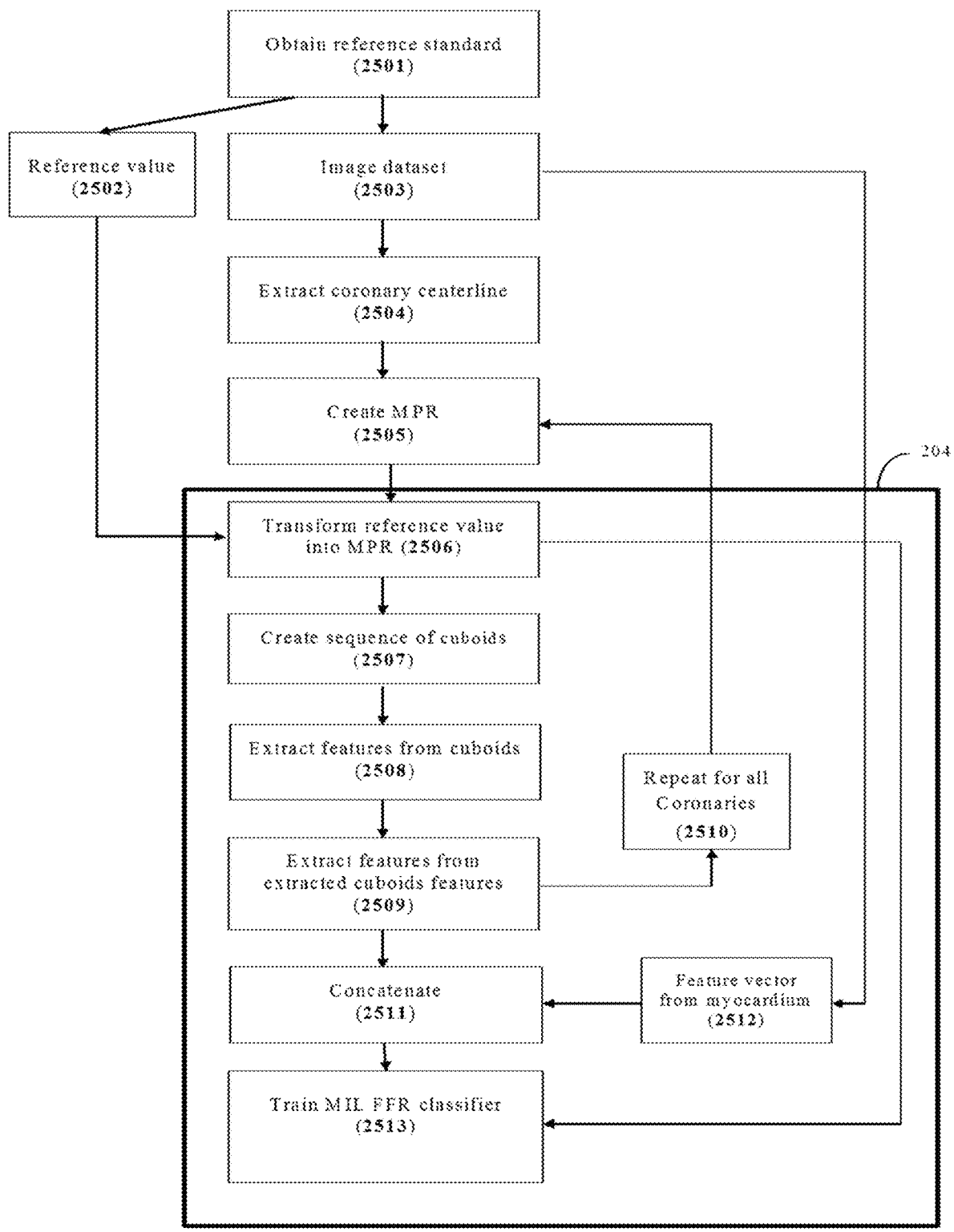
FIG. 25 shows an alternative flowchart of the generation of a multi-instance learning (MIL) FFR classification model as performed by the training phase.

Within an alternative embodiment, the machine learning algorithm represented by block 204 of FIG. 2 is deployed to assess the hemodynamic functional severity of one or more coronary vessel obstructions of a target organ, being the heart, based on contrast enhanced volumetric image dataset. FIG. 25 represent the flowchart of the training phase of the machine learning algorithm within this alternative embodiment and combines the method described by FIGS. 19a-19c with the teaching from Isgum et al. in U.S. Ser. No. 10/765,575B2 to assess the hemodynamic functional severity of one or more coronary vessel obstructions within a contrast enhanced volumetric image dataset. Features, of all extracted coronary arteries, with centerlines extracted like in (1804 FIG. 18), are extracted in an identical way as described by step 1801 up to and including step 1809 of FIG. 18. For instance, n coronary features (2006) are extracted (for instance 1024 features) per MPR image 2505 (per coronary artery) as described by FIG. 20. Then these features 2509 are combined with the feature vector (for instance a feature vector of 512 myocardium features) as obtained from the myocardium analysis (2512) as described by U.S. Ser. No. 10/765,575B2 by concatenation 2511. Input for the myocardium feature vector (2512) is a CCTA image dataset (2503). The concatenation steps is performed by appending the feature vector resulting from the coronary analysis (2509) to the feature vector 1412 resulting from the myocardium analysis. The results of the concatenation step are used to train a multi instance learning (MTh) FFR classifier 2513 as for instance described by Ilse et al in "Attention-based deep multiple instance learning", arXiv preprint arXiv:1802.04712. To be able to use such MTh classifier, each patient is represented as a bag of instances that includes all coronaries (with the extracted features) and a myocardium (with its extracted features). To build the bag of instances, the features of the coronaries are concatenated element wise with the features of the myocardium: features of each coronary i (2509) is concatenated (2511) with the myocardium features (2512), for i from 1 to N (total amount of coronaries represented by 2510). The result is a matrix with N rows and total number of features per row (e.g. 1536 features exciting of 512 for myocardium and 1024 for each coronary). The reference value 2502 belonging to an image dataset 2503 could be set, but not limited to, to the minimal invasively measured FFR in that patient (image dataset).

Figure 26:
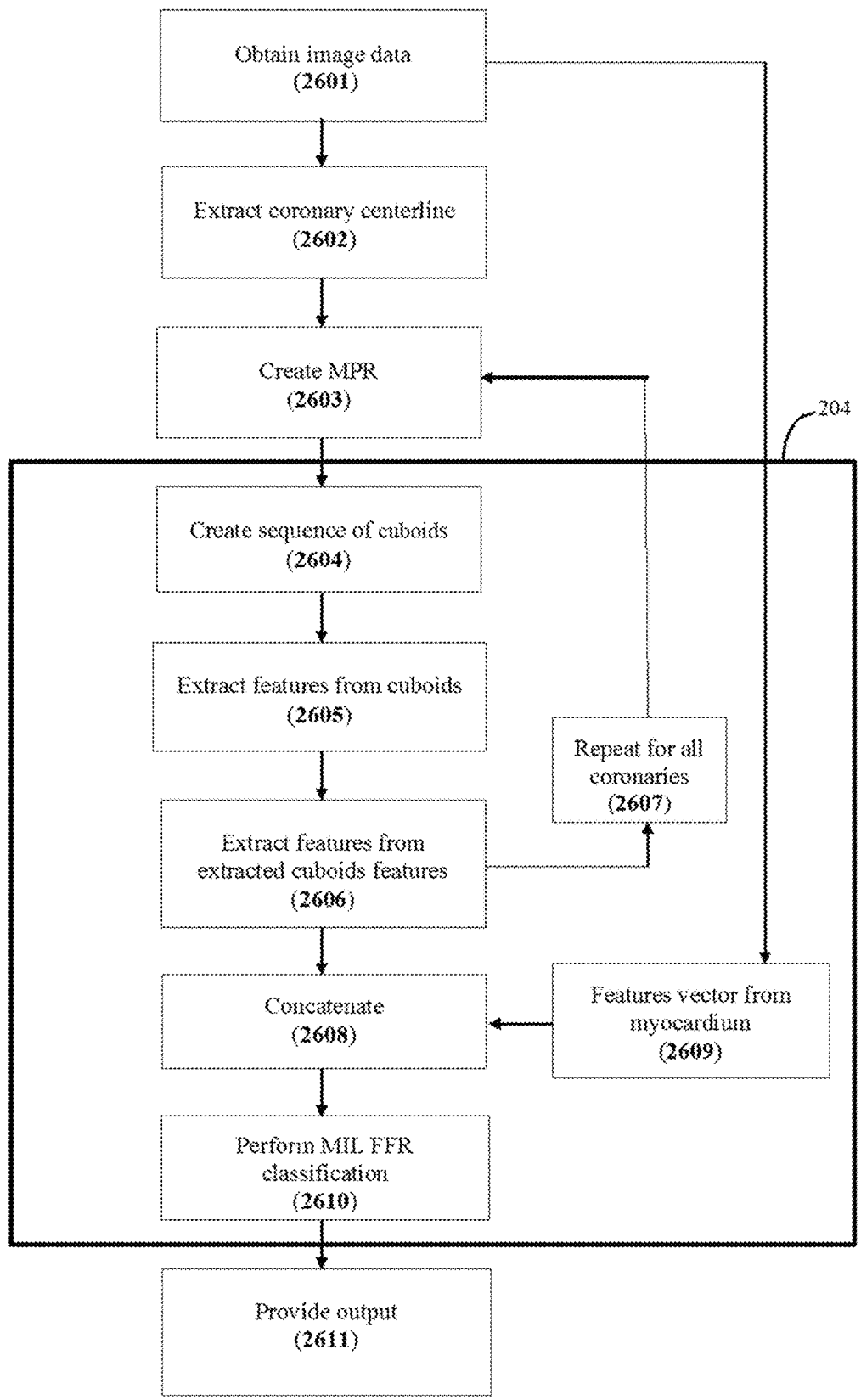
FIG. 26 shows an alternative flowchart of the prediction phase using the trained MIL FFR classification model as performed by the training phase.

FIG. 26 represent the flowchart during the prediction phase of the machine learning algorithm within this alternative embodiment in an assessment of the severity that one or more coronary obstructions impedes oxygen delivery to the heart muscle from a CCTA dataset. The unseen CCTA dataset is represented by step 2601 of FIG. 26.

Step 2602 of FIG. 26 the coronary centerline(s) are extracted which represent the center of the coronary lumen along each coronary section of interest. This step may be implemented in a manner substantially similar to step 202 of FIG. 2.

Step 2603 up to and including step 2606 of FIG. 26 are identical to step 2303 up to and including step 2306 of FIG. 23.

Step 2608 of FIG. 26 concatenate the feature vectors obtained from the unseen CCTA dataset based on coronary analysis 2606 and myocardium analysis 2609 in a similar way as described by block 2511 in FIG. 25 and including all available coronary centerlines (2607). The result of this concatenation step is fed into the MIL FFR classifier 2610 which has been trained as described by step 2513 of FIG. 25. Finally step 2611 provides the classification results from step 2610 to the user and may be implemented in a manner substantially similar to step 206 of FIG. 2.

With respect to step 203 of FIG. 2 which describes the creation of the MPR image, the current specification is mainly focus on the use of a straight MPR image. The description of step 203 includes the use of a curved MPR image, which allows curvature or tortuosity information of the extracted centerline can be taken into account within the described machine learning network architectures. Alternatively, this step can be skipped, and the generation of cubes as described by the relevant flowcharts can be performed directly on the image dataset using the extracted centerline as a result from step 202 of FIG. 2. In this way, curvature or tortuosity information is implicitly taken into account during training the machine learning based VAO models and also during the prediction phase.

With respect to prediction of the functionally significance of a coronary artery, either along the extracted coronary centerline or per extracted coronary centerline, it can be challenging to obtain a sufficient amount of invasively measured hemodynamic reference values. These invasively measured hemodynamic FFR reference values can be invasively measure FFR at the distal location of the coronary artery or invasively measure pullback FFR in case of prediction of the functionally significance of a coronary artery along the extracted coronary centerline.

As mentioned before, the reference standard (701, 1801, 2501) exist as part of a database which contains for each patent a) contrast enhanced CT datasets (703, 1803, 2503) and corresponding b) FFR reference values (702, 1802, 2502) such as for instance invasively measured fractional flow reserve. In most of the cases also x-ray angiographic image data is available of the patient. Within an alternative embodiment the FFR reference value (702 of FIG. 7 or 1802 of FIG. 18 or 2502 of FIG. 25) are obtained by calculation of the FFR pullback or calculation of the distal FFR value eliminating the need for invasively measure hemodynamic parameters such as for instance FFR. This can be performed by using the x-ray angiographic image data of the patient and compute the (pullback) FFR value by using for instance the vFFR (vessel-FFR) workflow within CAAS Workstation 8.0 (Pie Medical Imaging, the Netherlands). Due to the high spatial resolution of X-ray angiography and the method employed within CAAS Workstation vFFR workflow, the accuracy of the computed vFFR is considerably high, as presented at the EuroPCR 2018 by Masdjedi et al, "Validation of 3-Dimensional Quantitative Coronary Angiography based software to calculate vessel-FFR (the FAST study)".

Figure 27:
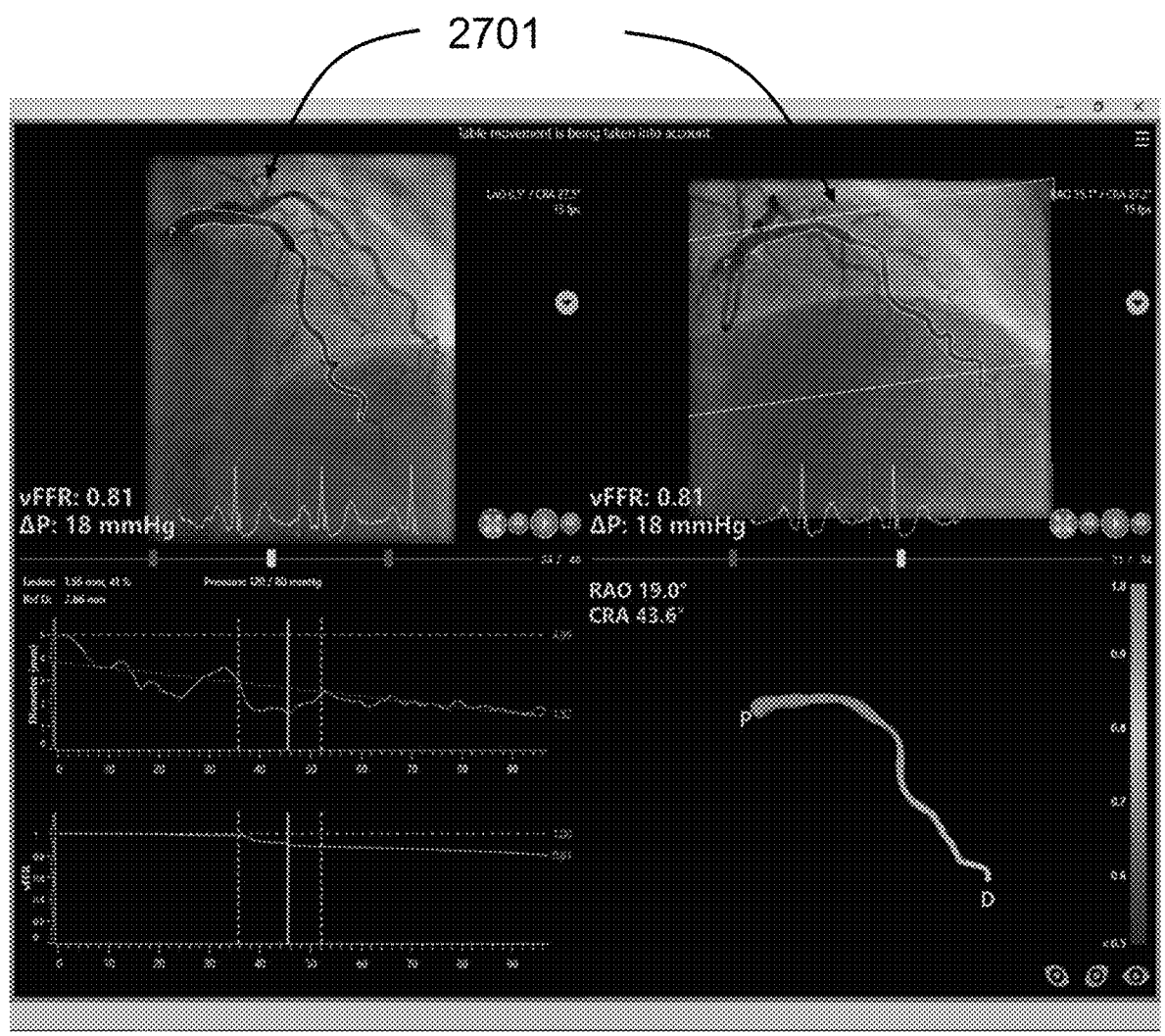
FIG. 27 shows an example of obtaining a computed FFR pullback of the coronary circumflex by using a CAAS Workstation.

The vFFR method of CAAS Workstation generates a 3D coronary reconstruction using 2 angiographic x-ray projections with at least 30 degrees apart. vFFR is calculated instantaneously by utilizing a proprietary algorithm which incorporates the morphology of the 3D coronary reconstruction and routinely measured patient specific aortic pressure. FIG. 27 shows an example of obtaining a computed FFR pullback of the coronary circumflex by using CAAS Workstation. 2701 shows the segmentation of the coronary circumflex in each 2D X-ray angiographic image, resulting in a 3D reconstruction of the coronary artery (2702). The graph 2703 shows the computed vFFR value along the length of the 3D reconstructed coronary artery. The same approach could also be performed on the CCTA dataset, eliminating the need to corresponding x-ray angiographic image data for each patient.

The present disclosure mainly describes the organ of interest as the myocardium and the vessels being the coronary arteries. The skilled person would appreciate that this teaching can be equally extended to other organs. For instance, the organ of interest can be the kidney, which is perfused by the renal arteries, or (parts) of the brain as perfused by the intracranial arteries. Furthermore, the present disclosure refers to CCTA datasets (in several forms).

The skilled person would appreciate that this teaching can be equally extended to other imaging modalities, for instance rotational angiography, MRI, SPECT, PET, Ultrasound, X-ray, or the like.

Figure 28:
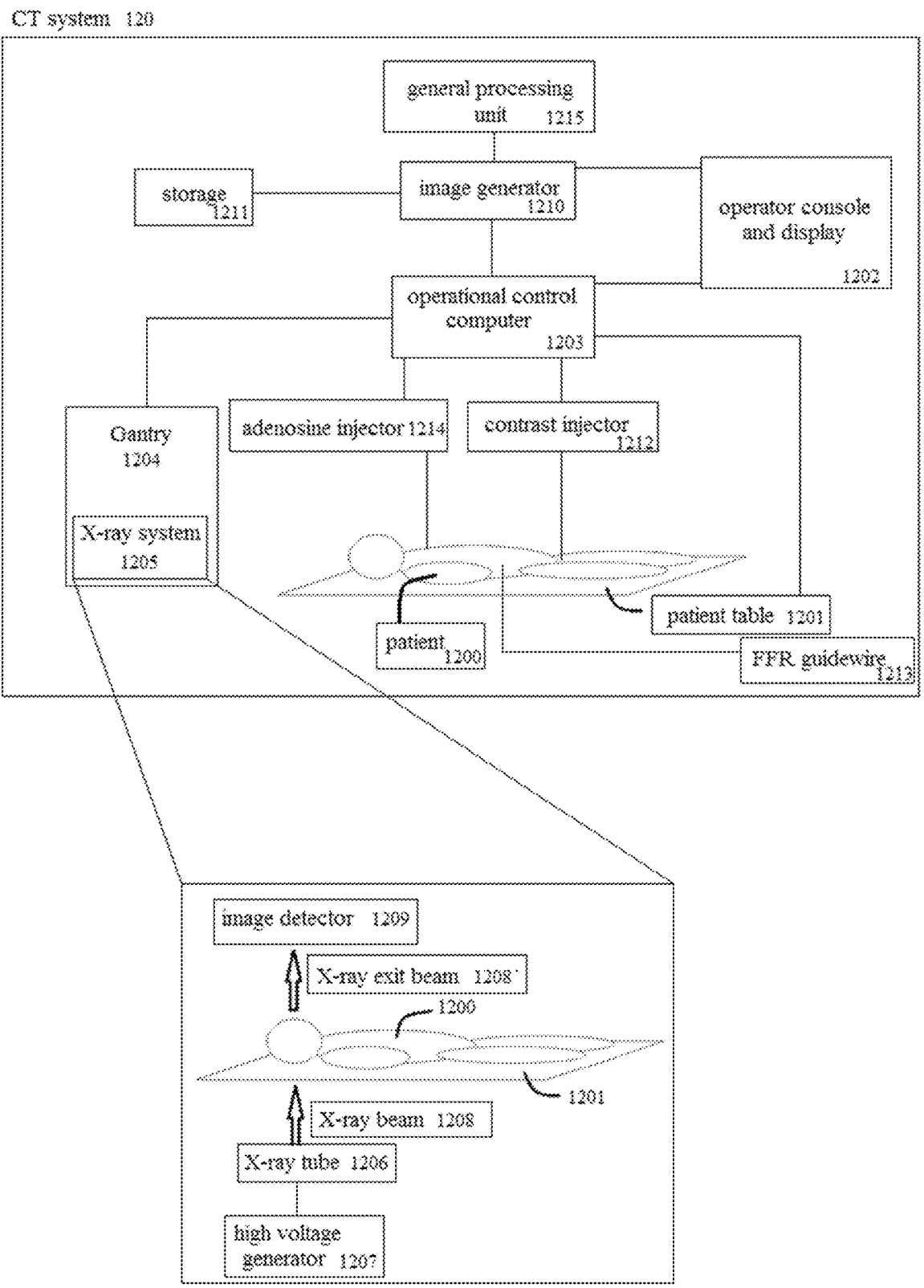
FIG. 28 shows a high level block diagram of an example of a CT system.

The embodiment of this disclosure can be used on a standalone system or included directly in, for instance, a computed tomography (CT) system. FIG. 28 illustrates an example of a high-level block diagram of a computed tomography (CT) system. In this block diagram the embodiment is included as an example how the present embodiment could integrate in such a system.

Portions of the system (as defined by various functional blocks) may be implemented with dedicated hardware, analog and/or digital circuitry, and/or one or more processors operating program instructions stored in memory.

The most common form of computed tomography is X-ray CT, but many other types of CT exist, such as dual-energy, spectral, multi-energy, or photon-counting CT. Also positron emission tomography (PET) and single-photon emission computed tomography (SPECT) or combined with any previous form of CT.

The CT system of FIG. 28 describes an X-ray CT system. In an X-ray CT system an X-ray system moves around a patient in a gantry and obtains images. Through use of digital processing a three-dimensional image is constructed from a large series of two-dimensional angiographic images taken around a single axis of rotation.

For a typical X-ray CT system 120 an operator positions a patient 1200 on the patient table 1201 and provides input for the scan using an operating console 1202. The operating console 1202 typically comprises of a computer, a keyboard/foot paddle/touchscreen and one or multiple monitors.

An operational control computer 1203 uses the operator console input to instruct the gantry 1204 to rotate but also sends instructions to the patient table 1201 and the X-ray system 1205 to perform a scan.

Using a selected scanning protocol selected in the operator console 1202, the operational control computer 1203 sends a series of commands to the gantry 1204, the patient table 1201 and the X-ray system 1205. The gantry 1204 then reaches and maintains a constant rotational speed during the entire scan. The patient table 1201 reaches the desired starting location and maintains a constant speed during the entire scan process.

The X-ray system 1205 includes an X-ray tube 1206 with a high voltage generator 1207 that generates an X-ray beam 1208.

The high voltage generator 1207 controls and delivers power to the X-ray tube 1206. The high voltage generator 1207 applies a high voltage across the vacuum gap between the cathode and the rotating anode of the X-ray tube 1206.

Due to the voltage applied to the X-ray tube 1206, electron transfer occurs from the cathode to the anode of the X-ray tube 1206 resulting in X-ray photon generating effect also called Bremsstrahlung. The generated photons form an X-ray beam 1208 directed to the image detector 1209.

An X-ray beam 1208 comprises of photons with a spectrum of energies that range up to a maximum determined by among others the voltage and current submitted to the X-ray tube 1206.

The X-ray beam 1208 then passes through the patient 1200 that lies on a moving table 1201. The X-ray photons of the X-ray beam 1208 penetrate the tissue of the patient to a varying degree. Different structures in the patient 1200 absorb different fractions of the radiation, modulating the beam intensity.

The modulated X-ray beam 1208' that exits from the patient 1200 is detected by the image detector 1209 that is located opposite of the X-ray tube.

This image detector 1209 can either be an indirect or a direct detection system.

In case of an indirect detection system, the image detector 1209 comprises of a vacuum tube (the X-ray image intensifier) that converts the X-ray exit beam 1208' into an amplified visible light image. This amplified visible light image is then transmitted to a visible light image receptor such as a digital video camera for image display and recording. This results in a digital image signal.

In case of a direct detection system, the image detector 1209 comprises of a flat panel detector. The flat panel detector directly converts the X-ray exit beam 1208' into a digital image signal.

The digital image signal resulting from the image detector 1209 is passed to the image generator 1210 for processing. Typically, the image generation system contains high-speed computers and digital signal processing chips. The acquired data are preprocessed and enhanced before they are sent to the display device 1202 for operator viewing and to the data storage device 1211 for archiving.

In the gantry the X-ray system is positioned in such a manner that the patient 1200 and the moving table 1201 lie between the X-ray tube 1206 and the image detector 1209.

In contrast enhanced CT scans, the injection of contrast agent must be synchronized with the scan. The contrast injector 1212 is controlled by the operational control computer 1203.

For FFR measurements an FFR guidewire 1213 is present, also adenosine is injected by an injector 1214 into the patient to induce a state of maximal hyperemia.

An embodiment of the present application is implemented by the X-ray CT system 120 of FIG. 18 as follows. A clinician or other user acquires a CT scan of a patient 1200 by selecting a scanning protocol using the operator console 1202. The patient 1200 lies on the adjustable table 1201 that moves at a continuous speed during the entire scan controlled by the operational control computer 1203. The gantry 1204 maintains a constant rotational speed during the entire scan Multiple two-dimensional X-ray images are then generated using the high voltage generator 1207, the X-ray tube 1206, the image detector 1209 and the digital image generator 1210 as described above. This image is then stored on the hard drive 1211. Using these X-ray images, a three-dimensional image is constructed by the image generator 1210.

The general processing unit 1215 uses the three-dimensional image to perform the classification as described above.

There have been described and illustrated herein several embodiments of a method and apparatus for automatically identify patients with functionally significant stenosis, based on the information extracted from a single CCTA image only.

Hereafter, a summary is provided of various aspects of embodiments herein that may be claimed alone or in any combination thereof.

Example 1

A method for assessing a vessel obstruction, the method comprising:

obtaining a volumetric image dataset for a target organ that includes a vessel of interest;

extracting an axial trajectory extending along of a vessel of interest (VOI) within the volumetric image dataset;

creating a three-dimensional (3D) multi-planer reformatted (MPR) image based on the volumetric image dataset and the axial trajectory of the VOI; and extracting a VOI parameter from the MPR image utilizing a machine learning-based vessel obstruction assessment (VOA) model.

Example 2

The method of one or more of the examples herein, further comprising implementing a prediction phase to at least one of i) detect plaque type; ii) classifying anatomical severity of vessel blockage; and/or iii) classifying a hemodynamic severity of vessel obstructions within an unseen portion of the volumetric image data set.

Example 3

The method of one or more of the examples herein, wherein the machine learning-based VOA model generates a sequence of cubes from the MPR image, each of the cubes including a group of voxel from the MPR image, the sequence of cubes created within sections of the VOI resulting in a sequence of cubes for corresponding sections.

Example 4

The method of one or more of the examples herein, wherein the machine learning-based VOA model extracts image features associated with cubes from the sequence of cubes independently.

Example 5

The method of one or more of the examples herein, wherein the machine learning analyzes the image features in sequential dependence.

Example 6

The method of one or more of the examples herein, wherein a size of the cube is defined to contain a whole lumen for the VOI and a portion of tissue outside of the lumen to facilitate extracting the VOI parameter in connection with positive remodeling, wherein positive remodeling refers to a direction of atherosclerotic plaque growth.

Example 7

The method of one or more of the examples herein, wherein the axial trajectory corresponds to a coronary centerline of the VOI, the coronary centerline representing a center of a coronary lumen along a coronary section of interest, the axial trajectory may correspond to a single coronary artery, a coronary bifurcation or a full coronary tree, wherein, when the coronary section of interest includes one or more bifurcation(s), the coronary centerline includes the one or more bifurcations.

Example 8

The method of one or more of the examples herein, wherein the machine learning-based VOA model is based on a recurrent convolutional neural network (RCNN) which is employed to analyze a vicinity along the axial trajectory of the VOI in the MPR image, the RCNN connects a convolutional neural network (CNN) with a recurrent neural network (RNN) connected in series to analyze the portion of the MPR along the axial trajectory as a sequential input.

Example 9

The method of one or more of the examples herein, wherein the machine learning-based VOA model applies at least one convolution layer followed by a max pooling layer to extract an image feature of interest from the MPR image and utilizes classifiers for at least one of detecting plaque type, characterizing plaque type, detecting stenosis or determining an anatomical significance of a stenosis.

Example 10

The method of one or more of the examples herein, wherein the machine learning-based VOA model includes a feature extraction for creating a feature vector based on the MPR image, the feature vector comprises a series of factors that are measured or extracted from a reference database of images, the series of factors describing or characterizing the nature of a corresponding wall region of the vessel of interest, the machine learning-based VOA model further including a classifier to classify the feature vector extracted from the MPR image.

Example 11

The method of one or more of the examples herein, wherein the VOI parameter includes at least one of coronary plaque type, anatomical coronary lesion severity or functionally significant coronary lesion severity, and wherein the machine learning-based VOA model assesses at least one of i) functionally significant coronary lesion severity, ii) plaque type or iii) anatomical coronary lesion severity.

Example 12

A method to train a vessel obstruction assessment (VOA) model, comprising:

obtaining a training database that includes volumetric imaging datasets for multiple patients and corresponding coronary artery disease (CAD) related reference values, the volumetric image data sets being for a target organ that includes a vessel of interest, the CAD related reference values corresponding to one or more points along a vessel of interest within the corresponding imaging data set; and for at least a portion of the volumetric image data sets and corresponding CAD related reference values, extracting an axial trajectory extending along of a vessel of interest (VOI) within the corresponding volumetric image dataset, creating a three-dimensional (3D) multi-planer reformatted (MPR) image based on the corresponding volumetric image dataset and the axial trajectory of the VOI, the MPR image extending along the axial trajectory of the VOI, and training a machine learning-based vessel obstruction assessment (VOA) model based on the MPR images, the training further comprising extracting, from the MPR images, features characterizing a CAD related parameter along the axial trajectory within the VOI.

Example 13

The method of one or more of the examples herein, further comprising aligning the CAD related reference values to spatial coordinates of the corresponding MPR images.

Example 14

The method of one or more of the examples herein, further comprising generating a sequence of cubes from the corresponding MPR images, each of the cubes including a group of voxel from the corresponding MPR image, the sequence of cubes created within sections of the VOI resulting in a sequence of cubes for corresponding sections.

Example 15

The method of one or more of the examples herein, wherein the training further comprises applying a convolutional neural network to a sequence of cubes alone the MPR image to build the machine learning-based VOA model.

Example 16

The method of one or more of the examples herein, wherein the applying further comprises generating a set of encodings at points along the axial trajectory to form a set of one-dimensional (1D) sequences, each of the 1D sequences representing a specific encoding along the VOI, the training further comprising applying a supervised classifier to learn a fractional flow reserve (FFR) classifier based on the 1D sequences.

Example 17

A system for assessing a vessel obstruction, comprising:
  memory configured to store a volumetric image dataset for a target organ that includes a vessel of interest; and
  one or more processors that, when executing program instructions stored in the memory, are configured to:
    extract an axial trajectory extending along of a vessel of interest (VOI) within the volumetric image dataset,
    create a three-dimensional (3D) multi-planer reformatted (MPR) image based on the volumetric image dataset and the axial trajectory of the VOI, and
    extract a VOI parameter from the MPR image utilizing a machine learning-based vessel obstruction assessment (VOA) model.

Example 18

The system of one or more of the examples herein, wherein the one or more processors are configured to implement a prediction phase to at least one of i) detect plaque type, ii) classify anatomical severity of vessel blockage, and/or iii) classify a hemodynamic severity of vessel obstructions within an unseen portion of the volumetric image data set.

Example 19

The system of one or more of the examples herein, wherein the machine learning-based VOA model generates a sequence of cubes from the MPR image, each of the cubes including a group of voxel from the MPR image, the sequence of cubes created within sections of the VOI resulting in a sequence of cubes for corresponding sections.

Example 20

The system of one or more of the examples herein, wherein the machine learning-based VOA model extracts image features associated with cubes from the sequence of cubes independently.

Example 21

The system of one or more of the examples herein, wherein the machine learning analyzes the image features in sequential dependence.

Example 22

The system of one or more of the examples herein, wherein a size of the cube is defined to contain a whole lumen for the VOI and a portion of tissue outside of the lumen to facilitate extracting the VOI parameter in connection with positive remodeling, wherein positive remodeling refers to a direction of atherosclerotic plaque growth.

Example 23

The system of one or more of the examples herein, wherein the axial trajectory corresponds to a coronary centerline of the VOI, the coronary centerline representing a center of a coronary lumen along a coronary section of interest, the axial trajectory may correspond to a single coronary artery, a coronary bifurcation or a full coronary tree, wherein, when the coronary section of interest includes one or more bifurcation(s), the coronary centerline includes the one or more bifurcations.

Example 24

The system of one or more of the examples herein, wherein the machine learning-based VOA model is based on a recurrent convolutional neural network (RCNN) which is employed to analyze a vicinity along the axial trajectory of the VOI in the MPR image, the RCNN connects a convolutional neural network (CNN) with a recurrent neural network (RNN) connected in series to analyze the portion of the MPR along the axial trajectory as a sequential input.

Example 25

The system of one or more of the examples herein, wherein the machine learning-based VOA model applies at least one convolution layer followed by a max pooling layer to extract an image feature of interest from the MPR image and utilizes classifiers for at least one of detecting plaque type, characterizing plaque type, detecting stenosis or determining an anatomical significance of a stenosis.

Example 26

The system of one or more of the examples herein, wherein the machine learning-based VOA model includes a feature extraction for creating a feature vector based on the MPR image, the feature vector comprises a series of factors that are measured or extracted from a reference database of images, the series of factors describing or characterizing the nature of a corresponding wall region of the vessel of interest, the machine learning-based VOA model further including a classifier to classify the feature vector extracted from the MPR image.

Example 27

The system of one or more of the examples herein, wherein the VOI parameter includes at least one of coronary plaque type, anatomical coronary lesion severity or functionally significant coronary lesion severity, and wherein the machine learning-based VOA model assesses at least one of i) functionally significant coronary lesion severity, ii) plaque type or iii) anatomical coronary lesion severity.

Example 28

A system to train a vessel obstruction assessment (VOA) model, comprising:
memory configured to store a training database that includes volumetric imaging datasets for multiple patients and corresponding coronary artery disease (CAD) related reference values, the volumetric image data sets being for a target organ that includes a vessel of interest, the CAD related reference values corresponding to one or more points along a vessel of interest within the corresponding imaging data set; and
one or more processors that, when executing program instructions stored in the memory, are configured to:
for at least a portion of the volumetric image data sets and corresponding CAD related reference values,
extract an axial trajectory extending along of a vessel of interest (VOI) within the corresponding volumetric image dataset,
create a three-dimensional (3D) multi-planer reformatted (MPR) image based on the corresponding volumetric image dataset and the axial trajectory of the VOI, the MPR image extending along the axial trajectory of the VOI, and
train a machine learning-based vessel obstruction assessment (VOA) model based on the MPR images, which involves extracting, from the MPR images, features characterizing a CAD related parameter along the axial trajectory within the VOI.

Example 29

The system of one or more of the examples herein, wherein the one or more processors are further configured to align the CAD related reference values to spatial coordinates of the corresponding MPR images.

Example 30

The system of one or more of the examples herein, wherein the one or more processors are further configured to generate a sequence of cubes from the corresponding MPR images, each of the cubes including a group of voxel from the corresponding MPR image, the sequence of cubes created within sections of the VOI resulting in a sequence of cubes for corresponding sections.

Example 31

The system of one or more of the examples herein, wherein the one or more processors are further configured to apply a convolutional neural network to a sequence of cubes alone the MPR image to build the machine learning-based VOA model.

Example 32

The system of one or more of the examples herein, wherein the one or more processors are further configured to generate a set of encodings at points along the axial trajectory to form a set of one-dimensional (1D) sequences, each of the 1D sequences representing a specific encoding along the VOI, and to perform the training by applying a supervised classifier to learn a fractional flow reserve (FFR) classifier based on the 1D sequences.

While particular embodiments of the present application have been described, it is not intended that the present application be limited thereto, as it is intended that the present application be as broad in scope as the art will allow and that the specification be read likewise.

For example, multi-phase CCTA datasets can be used, functional assessment of renal arties in relation to the perfused kidney can be assess based on the methodology disclosed, the data processing operations can be performed offline on images stored in digital storage, such as a PACS or VNA in DICOM (Digital Imaging and Communications in Medicine) format commonly used in the medical imaging arts. It will therefore be appreciated by those skilled in the art that yet other modifications could be made to the provided application without deviating from its spirit and scope as claimed.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art.

Similarly, any necessary files for performing the functions attributed to the computers, servers or other network devices may be stored locally and/or remotely, as appropriate.

Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above.

The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services, or other elements located within at least one working memory device, including an operating system and application programs, such as a client application or web browser.

It should be appreciated that alternate embodiments may have numerous variations from that described above. For example, customized hardware might also be used and/or particular elements might be implemented in hardware, software (including portable software, such as applets) or both.

Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the present application as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the present application to the specific form or forms disclosed, but on the contrary, the intention is to cover all modifications, alternative constructions and equivalents falling within the spirit and scope of the present application, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open ended terms (i.e., meaning "including, but not limited to,") unless otherwise noted. The term "connected," when unmodified and referring to physical connections, is to be construed as partly or wholly contained within, attached to or joined together, even if there is something intervening.

Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members.

Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the present application. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein.

Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. A method for assessing a vessel obstruction, comprising:
   a) obtaining a volumetric image dataset of a myocardium and at least one coronary vessel, wherein the myocardium comprises muscular tissue of the heart;
   b) creating a three-dimensional (3D) image corresponding to a coronary vessel of interest based on the volumetric image dataset of a) and axial trajectory of the coronary vessel of interest that is extracted from the volumetric image dataset of a);
   c) generating feature data that represents features of both the myocardium and the coronary vessel of interest, wherein the feature data is determined by i) sampling image data of the 3D image of b) that lies along the axial trajectory of the coronary vessel of interest, ii) using the sampled image data as input to a first machine learning-based model configured to automatically generate at least first feature data representing features of the coronary vessel of interest, iii) generating second feature data from additional myocardium analysis of the volumetric image dataset of a), wherein the second feature data represents features of the myocardium, and iv) combining the first feature data and the second feature data to generate the feature data of c); and d) employing a second machine learning-based model to determine at least one parameter based on the feature data of c), wherein the at least one parameter represents functionally significant coronary lesion severity of the coronary vessel of interest.

2. The method of claim 1, wherein:
the at least one parameter that represents functionally significant coronary lesion severity is selected from the group consisting of: a fractional flow reserve (FFR) value, coronary flow reserve value, instantaneous wave-free ratio, hyperemic myocardium perfusion value, index of microcirculatory resistance, pressure drop along a coronary artery, FFR along a coronary artery, and combinations thereof.

3. The method of claim 1, wherein:
the second feature data is determined using at least one of: a convolutional auto-encoder, Gaussian filters, transmural perfusion ratio, Haralick features, myocardium thickness, and heart shape.

4. The method of claim 1, wherein:
the second feature data is determined using an unsupervised machine learning which employs a convolution auto-encoder.

5. The method of claim 1, further comprising:
repeating the operations of c) and d) using image data corresponding to the axial trajectory of the coronary vessel of interest to determine values of the at least one parameter representing functionally significant coronary lesion severity along the length of the coronary vessel of interest.

6. The method of claim 5, wherein:
the image data corresponding to the axial trajectory of the coronary vessel includes cubes or cuboids that are sampled from the 3D image and extend along the axial trajectory of the coronary vessel of interest.

7. The method of claim 1, wherein:
the axial trajectory of the coronary vessel of interest corresponds to a centerline of the coronary vessel of interest.

8. The method of claim 1, wherein:
the 3D image comprises a multi-planer reformatted (MPR) image that is constructed from samples of the volumetric image dataset along an axial trajectory of the coronary vessel of interest.

9. The method of claim 1, wherein:
multiple 3D images are created based on the volumetric dataset, wherein the multiple 3D images correspond to a plurality of coronary vessels of interest and are based on extraction of axial trajectories for the plurality of coronary vessels of interest.

10. The method of claim 9, wherein:
the axial trajectories for the plurality of coronary vessels of interest corresponds to centerlines for plurality of coronary vessels of interest.

11. The method of claim 9, further comprising:
using sampled image data from the multiple 3D images that lies along the axial trajectories for the plurality of coronary vessels of interest as input to the first machine learning-based model to generate data representing features of the plurality of coronary vessels of interest, wherein such data is included in the feature data of c).

12. The method of claim 1, wherein:
the first machine learning-based model comprises a recurrent convolutional neural network or at least one convolutional autoencoder.

13. The method of claim 1, wherein:
the second machine learning-based model comprises a supervised machine learning classifier.

14. The method of claim 13, wherein:
the second machine learning-based model comprises a neural network, at least one SoftMax classifier, or a support vector machine.

15. The method of claim 1, wherein:
the second machine learning-based model is trained using reference values derived from invasive measurements involving pullback of a guidewire located in a target coronary vessel, measured coronary flow reserve, index of microcirculatory resistance, major adverse cardiac events or revascularization after acquisition of the volume image data set, results of cardiac stress test, and results of myocardial imaging by magnetic resonance imaging (MRI), SPECT, PET, CT perfusion, or ultrasound.

16. The method of claim 15, wherein:
the training of the second machine learning-based model involves aligning the reference values to spatial coordinates of a 3D image corresponding to the target coronary vessel.

17. A system for assessing a vessel obstruction, comprising:
memory configured to store program instructions and to store a volumetric image dataset of a myocardium and at least one coronary vessel, wherein the myocardium comprises muscular tissue of the heart;
at least one processor that, when executing the program instructions stored in the memory, is configured to:
a) obtain a volumetric image dataset of a myocardium and at least one coronary vessel;
b) create a three-dimensional (3D) image corresponding to a coronary vessel of interest based on the volumetric image dataset of a) and axial trajectory of the coronary vessel of interest that is extracted from the volumetric image dataset of a);
c) generate feature data that represents features of both the myocardium and the coronary vessel of interest, wherein the feature data is determined by i) sampling image data of the 3D image of b) that lies along the axial trajectory of the coronary vessel of interest, ii) using the sampled image data as input to a first machine learning-based model configured to automatically generate at least first feature data representing features of the coronary vessel of interest, iii) generating second feature data from additional myocardium analysis of the volumetric image dataset of a), wherein the second feature data represents features of the myocardium, and iv) combining the first feature data and the second feature data to generate the feature data of c); and
d) employ a second machine learning-based model to determine at least one parameter based on the feature data of c), wherein the at least one parameter represents functionally significant coronary lesion severity of the coronary vessel of interest.

18. The system of claim 17, wherein:
the at least one parameter that represents functionally significant coronary lesion severity is selected from the group consisting of: a fractional flow reserve (FFR) value, coronary flow reserve value, instantaneous wave-free ratio, hyperemic myocardium perfusion value, index of microcirculatory resistance, pressure drop along a coronary artery, FFR along a coronary artery, and combinations thereof.

19. The system of claim 17, wherein:
the 3D image comprises a multi-planer reformatted (MPR) image that is constructed from samples of the volumetric image dataset along the axial trajectory of the coronary vessel of interest.

20. The system of claim 17, wherein:
the axial trajectory of the coronary vessel of interest corresponds to a centerline of the coronary vessel of interest.

21. The system of claim 17, wherein:
the at least one processor is configured to repeat the operations of c) and d) using image data corresponding to the axial trajectory of the coronary vessel of interest to determine values of the at least one parameter representing functionally significant coronary lesion severity along the length of the coronary vessel of interest.

22. The system of claim 17, wherein:
the first machine-learning based model is configured to automatically extract image features associated with cubes or cuboids that are sampled from the 3D image and extend along the axial trajectory of the coronary vessel of interest.

23. The system of claim 17, wherein:
the at least one processor is configured to create multiple 3D images based on the volumetric dataset, wherein the multiple 3D images correspond to a plurality of coronary vessels of interest and are based on extraction of axial trajectories for the plurality of coronary vessels of interest.

24. The system of claim 23, wherein:
the axial trajectories for the plurality of coronary vessels of interest corresponds to centerlines for plurality of coronary vessels of interest.

25. The system of claim 23, wherein:
the at least one processor is configured to use sampled image data from the multiple 3D images along the axial trajectories for the plurality of coronary vessels of interest as input to the first machine learning-based model to generate data representing features of the plurality of coronary vessels of interest, wherein such data is included in the feature data of c).

26. The system of claim 17, wherein:
the first machine learning-based model comprises a recurrent convolutional neural network or at least one convolutional autoencoder.

27. The system of claim 17, wherein:
the second machine learning-based model comprises a supervised machine learning classifier.

28. The system of claim 27, wherein:
the second machine learning-based model comprises a neural network, at least one SoftMax classifier, or a support vector machine.

29. The system of claim 17, wherein:
the second machine learning-based model is trained using reference values derived from invasive measurements involving pullback of a guidewire located in a target coronary vessel.

30. The system of claim 29, wherein:
the second machine learning-based model is trained by aligning the reference values to spatial coordinates of a 3D image corresponding to the target coronary vessel.

31. The system of claim 17, wherein:
the second feature data is determined using at least one of: a convolutional auto-encoder, Gaussian filters, transmural perfusion ratio, Haralick features, myocardium thickness, and heart shape.

32. The system of claim 17, wherein:
the second feature data is determined using an unsupervised machine learning which employs a convolution auto-encoder.

* * * * *